US008465724B2

(12) United States Patent
Vlahov et al.

(10) Patent No.: US 8,465,724 B2
(45) Date of Patent: Jun. 18, 2013

(54) MULTI-DRUG LIGAND CONJUGATES

(75) Inventors: Iontcho Radoslavov Vlahov, West Lafayette, IN (US); Christopher Paul Leamon, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 942 days.

(21) Appl. No.: 12/064,191

(22) PCT Filed: Aug. 18, 2006

(86) PCT No.: PCT/US2006/032561
§ 371 (c)(1),
(2), (4) Date: Feb. 19, 2008

(87) PCT Pub. No.: WO2007/022494
PCT Pub. Date: Feb. 22, 2007

(65) Prior Publication Data
US 2008/0248052 A1    Oct. 9, 2008

Related U.S. Application Data

(60) Provisional application No. 60/709,950, filed on Aug. 19, 2005, provisional application No. 60/787,558, filed on Mar. 30, 2006.

(51) Int. Cl.
*A61K 51/00*  (2006.01)
*A61M 36/14*  (2006.01)

(52) U.S. Cl.
USPC ........................................ 424/1.53; 424/178.1

(58) Field of Classification Search
None
See application file for complete search history.

(56) References Cited

U.S. PATENT DOCUMENTS

| | | |
|---|---|---|
| 2,515,483 A | 7/1950 | Wolf et al. |
| 2,816,110 A | 12/1957 | Sletzinger et al. |
| 3,387,001 A | 6/1968 | Hargrove et al. |
| 3,392,173 A | 7/1968 | Hargrove et al. |
| 4,166,810 A | 9/1979 | Cullinan et al. |
| 4,203,898 A | 5/1980 | Cullinan et al. |
| 4,316,885 A | 2/1982 | Rakhit |
| 4,337,339 A | 6/1982 | Farina et al. |
| 4,639,456 A | 1/1987 | Trouet et al. |
| 4,650,803 A | 3/1987 | Stella et al. |
| 4,691,024 A | 9/1987 | Shirahata |
| 4,713,249 A | 12/1987 | Schroder |
| 4,770,994 A * | 9/1988 | Rittenhouse ............. 435/7.23 |
| 4,801,688 A | 1/1989 | Laguzza et al. |
| 4,866,180 A | 9/1989 | Vyas et al. |
| 4,870,162 A | 9/1989 | Trouet et al. |
| 5,006,652 A | 4/1991 | Cullinan et al. |
| 5,094,849 A | 3/1992 | Cullinan et al. |
| 5,100,883 A | 3/1992 | Schiehser |
| 5,108,921 A | 4/1992 | Low et al. |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,138,051 A | 8/1992 | Hughes et al. |
| 5,140,104 A | 8/1992 | Coughlin et al. |
| 5,151,413 A | 9/1992 | Caufield et al. |
| 5,169,851 A | 12/1992 | Hughes et al. |
| 5,194,447 A | 3/1993 | Kao |
| 5,221,670 A | 6/1993 | Caufield |
| 5,233,036 A | 8/1993 | Hughes |
| 5,258,389 A | 11/1993 | Goulet et al. |
| 5,260,300 A | 11/1993 | Hu |
| 5,266,333 A | 11/1993 | Cady et al. |
| 5,302,584 A | 4/1994 | Kao et al. |
| 5,362,718 A | 11/1994 | Skotnicki et al. |
| 5,378,696 A | 1/1995 | Caufield |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,416,016 A | 5/1995 | Low et al. |
| 5,417,982 A | 5/1995 | Modi |
| 5,463,048 A | 10/1995 | Skotnicki et al. |
| 5,491,231 A | 2/1996 | Nelson et al. |
| 5,547,668 A | 8/1996 | Kranz et al. |
| 5,552,545 A | 9/1996 | Pearce et al. |
| 5,627,165 A | 5/1997 | Glazier |

(Continued)

FOREIGN PATENT DOCUMENTS

| | | |
|---|---|---|
| CA | 2372841 | 11/2000 |
| CA | 2376175 | 12/2000 |
| EP | 0 116 208 A1 | 8/1984 |
| EP | 0 163 550 A2 | 12/1985 |
| EP | 0247792 A2 | 12/1987 |
| EP | 0 280 741 A1 | 9/1988 |
| EP | 0 354 728 | 2/1990 |
| JP | 59-175493 | 10/1984 |
| JP | 60-255789 | 12/1985 |
| WO | WO 85/05554 | 12/1985 |

(Continued)

OTHER PUBLICATIONS

International Search Report for PCT/US2006/032561 dated Jul. 11, 2007.
Barrett, Charles J., et al., "Structure-Activity Relationships of Dimeric Catharanthus Alkaloids. 1. Deacetylvinblastine Amide (Vindesine) Sulfate", 1978, *Journal of Medicinal Chemistry*, vol. 21, No. 1, pp. 88-96.
Eichman, Jonathan D., et al., "The Use of Pamam Dendrimers in the Efficient Transfer of Genetic Material Into Cells", Jul. 2000, PSTT, vol. 3, No. 7, pp. 232-245.

(Continued)

*Primary Examiner* — Michael G Hartley
*Assistant Examiner* — Sean R Donohue
(74) *Attorney, Agent, or Firm* — Barnes & Thornburg LLP

(57) ABSTRACT

Described herein are compounds, pharmaceutical compositions and methods for treating pathogenic cell populations in a patient. The compounds described herein include conjugates of a plurality of cytotoxic drugs and vitamin receptor binding ligands. The plurality of drugs may be the same or different. Similarly, the vitamin receptor binding ligands may be the same or different. The conjugates also include a linker that is formed from one or more spacer linkers, heteroatom linkers, and releasable linkers.

9 Claims, 9 Drawing Sheets

U.S. PATENT DOCUMENTS

| | | | |
|---|---|---|---|
| 5,635,382 | A | 6/1997 | Low et al. |
| 5,672,486 | A | 9/1997 | Soulillou |
| 5,688,488 | A | 11/1997 | Low et al. |
| 5,998,603 | A | 12/1999 | Cook |
| 6,004,555 | A | 12/1999 | Thorpe et al. |
| 6,030,941 | A | 2/2000 | Summerton et al. |
| 6,056,973 | A | 5/2000 | Allen |
| 6,077,499 | A | 6/2000 | Griffiths |
| 6,093,382 | A | 7/2000 | Wedeking et al. |
| 6,171,614 | B1 | 1/2001 | Chaikof et al. |
| 6,171,859 | B1 | 1/2001 | Herrnstadt et al. |
| 6,177,404 | B1 | 1/2001 | DeFeo-Jones et al. |
| 6,184,042 | B1 | 2/2001 | Neumann et al. |
| 6,207,157 | B1 | 3/2001 | Gu et al. |
| 6,290,929 | B1 | 9/2001 | Camden et al. |
| 6,291,673 | B1 | 9/2001 | Fuchs et al. |
| 6,291,684 | B1 | 9/2001 | Borzilleri et al. |
| 6,315,978 | B1 * | 11/2001 | Grissom et al. ............ 424/1.53 |
| 6,335,434 | B1 | 1/2002 | Guzaev et al. |
| 6,340,701 | B1 | 1/2002 | Chari et al. |
| 6,365,179 | B1 | 4/2002 | Zalipsky et al. |
| 6,399,625 | B1 | 6/2002 | Zhu |
| 6,399,626 | B1 | 6/2002 | Zhu et al. |
| 6,399,638 | B1 | 6/2002 | Vite et al. |
| 6,432,973 | B1 | 8/2002 | Zhu et al. |
| 6,440,991 | B1 | 8/2002 | Zhu et al. |
| 6,511,986 | B2 | 1/2003 | Zhang et al. |
| 6,541,612 | B2 | 4/2003 | Molnar-Kimber et al. |
| 6,596,757 | B1 | 7/2003 | Chari et al. |
| 6,617,333 | B2 | 9/2003 | Rabindran et al. |
| 6,670,355 | B2 | 12/2003 | Azrulan et al. |
| 6,677,357 | B2 | 1/2004 | Zhu et al. |
| 6,680,330 | B2 | 1/2004 | Zhu et al. |
| 6,713,607 | B2 | 3/2004 | Caggiano et al. |
| 6,800,653 | B2 | 10/2004 | Regueiro-Ren et al. |
| 6,821,731 | B2 | 11/2004 | Gillis et al. |
| 6,915,855 | B2 | 7/2005 | Steele et al. |
| 6,958,153 | B1 | 10/2005 | Ormerod et al. |
| 7,019,014 | B2 | 3/2006 | Bernan et al. |
| 7,029,674 | B2 | 4/2006 | Carreno et al. |
| 7,033,594 | B2 | 4/2006 | Low et al. |
| 7,060,709 | B2 | 6/2006 | Cooperstone et al. |
| 7,060,797 | B2 | 6/2006 | O'Toole et al. |
| 7,067,111 | B1 | 6/2006 | Yang et al. |
| 7,074,804 | B2 | 7/2006 | Zhu et al. |
| 7,105,328 | B2 | 9/2006 | Wood et al. |
| 7,122,361 | B2 | 10/2006 | Liu et al. |
| 7,128,893 | B2 | 10/2006 | Leamon et al. |
| 7,153,957 | B2 | 12/2006 | Chew et al. |
| 7,601,332 | B2 | 10/2009 | Vlahov et al. |
| 2001/0031252 | A1 | 10/2001 | Low et al. |
| 2003/0086900 | A1 | 5/2003 | Low et al. |
| 2003/0162234 | A1 | 8/2003 | Jallad |
| 2004/0018203 | A1 | 1/2004 | Pastan et al. |
| 2004/0033195 | A1 | 2/2004 | Leamon et al. |
| 2004/0047917 | A1 * | 3/2004 | Wilson et al. ............ 424/649 |
| 2004/0242582 | A1 | 12/2004 | Green et al. |
| 2005/0002942 | A1 | 1/2005 | Vlahov et al. |
| 2005/0004010 | A1 | 1/2005 | Collins et al. |
| 2005/0026068 | A1 | 2/2005 | Gogolides et al. |
| 2005/0107325 | A1 | 5/2005 | Mancharan et al. |
| 2005/0165227 | A1 | 7/2005 | Vlahov et al. |
| 2005/0227985 | A9 | 10/2005 | Green et al. |
| 2005/0239713 | A1 | 10/2005 | Domling et al. |
| 2005/0239739 | A1 | 10/2005 | Matulic-Adamic et al. |
| 2006/0058266 | A1 | 3/2006 | Manoharan et al. |
| 2006/0105975 | A1 | 5/2006 | Pendergrast et al. |
| 2006/0128754 | A1 | 6/2006 | Hoefle et al. |
| 2007/0009434 | A1 | 1/2007 | Low et al. |
| 2007/0134332 | A1 | 6/2007 | Turnell et al. |
| 2007/0275904 | A1 | 11/2007 | Vite et al. |
| 2008/0207625 | A1 | 8/2008 | Xu et al. |
| 2008/0248052 | A1 | 10/2008 | Vlahov et al. |
| 2008/0280937 | A1 | 11/2008 | Leamon et al. |
| 2009/0203889 | A1 | 8/2009 | Vlahov et al. |
| 2010/0004276 | A1 | 1/2010 | Vlahov et al. |
| 2010/0048490 | A1 | 2/2010 | Vlahov et al. |
| 2010/0104626 | A1 | 4/2010 | Leamon et al. |
| 2011/0288152 | A1 | 11/2011 | Low et al. |
| 2012/0258905 | A1 | 10/2012 | Leamon et al. |
| 2012/0270791 | A1 | 10/2012 | Leamon et al. |

FOREIGN PATENT DOCUMENTS

| | | |
|---|---|---|
| WO | WO 88/01622 | 3/1988 |
| WO | WO 90/12096 | 10/1990 |
| WO | WO91/07418 | 5/1991 |
| WO | WO96/36367 | 11/1996 |
| WO | WO 98/10651 | 3/1998 |
| WO | WO 9808859 A1 * | 3/1998 |
| WO | WO 99/20626 | 4/1999 |
| WO | WO 99/61055 | 12/1999 |
| WO | WO 00/35422 | 6/2000 |
| WO | WO00/66091 | 11/2000 |
| WO | WO 00/74721 | 12/2000 |
| WO | WO 01/13957 | 3/2001 |
| WO | WO01/28592 | 4/2001 |
| WO | WO 01/74382 | 10/2001 |
| WO | WO 02/085908 | 10/2002 |
| WO | WO 02/87424 | 11/2002 |
| WO | WO 02/098868 | 12/2002 |
| WO | WO 03/097647 | 11/2003 |
| WO | WO 2004/005326 | 1/2004 |
| WO | WO 2004/005327 | 1/2004 |
| WO | WO 2004/012735 | 2/2004 |
| WO | WO 2004/022099 | 3/2004 |
| WO | WO 2004/037210 | 5/2004 |
| WO | WO 2004/046170 | 6/2004 |
| WO | WO 2004/054622 | 7/2004 |
| WO | WO2004/069159 | 8/2004 |
| WO | WO2004/100983 | 11/2004 |
| WO | WO 2005/074901 | 8/2005 |
| WO | WO 2005/112919 | 12/2005 |
| WO | WO2006/012527 | 2/2006 |
| WO | WO 2006/042146 | 4/2006 |
| WO | WO 2006/089007 | 8/2006 |
| WO | WO 2006/101845 | 9/2006 |
| WO | WO2006/105141 | 10/2006 |
| WO | WO 2007/022493 | 2/2007 |
| WO | WO 2007/022494 | 2/2007 |
| WO | WO 2008/057437 | 5/2008 |
| WO | WO 2008/101231 | 8/2008 |
| WO | WO 2008/112873 | 9/2008 |
| WO | WO 2009/002993 | 12/2008 |
| WO | WO 2009/055562 | 4/2009 |

OTHER PUBLICATIONS

Langone, John J., et al., "Radioimmunoassays for the Vinca Alkaloids, Vinblastine and Vincristine", 1979, *Analytical Biochemistry*, No. 95, pp. 214-221.

Melby, Elisabeth L., et al., "Entry of Protein Toxins in Polarized Epithelial Cells", Apr. 15, 1993, *Cancer Research*, No. 53, pp. 1755-1760.

Neuss, Norbert, et al., "Vinca Alkaloids. XXX (1). Chemistry of the Deoxyvinblastines (Deoxy-VLB), Leurosine (VLR), and Pleurosine, Dimeric Alkaloids From Vinca", Tetrahedron Letters, No. 7, pp. 783-787.

Olsnes, Sjur, et al., "Immunotoxins-Entry Into Cell and Mechanisms of Action", 1989, *Immunology Today*, vol. 10, No. 9, pp. 292-295.

Agoston E.S. et al., "Vitamin D Analogs as Anti-Carcinogenic Agents," *Anti-Cancer Agents in Medicinal Chemistry*, 2006; 6(1): 53-71.

Anderson et al., "Potocytosis: Sequestration and transport of small molecules by caveolae," *Science*, 1992; 255: 410-411.

Antony A.C., "Folate receptors," *Annu Rev Nutr*, 1996; 16: 501-21.

Antony A.C., "The biological chemistry of folate receptors," *Blood*, 1992; 79(11):2807-2820.

Antony A.C. et al., "Studies of the Role of a Particulate Folate-binding Protein in the Uptake of 5-Methyltetrahydrofolate by Cultured Human KB Cells," *J. Biological Chem.*, 1985; 260(28):14911-7.

Archer M.C. et al., "Separation of Folic Acid Derivatives and Pterins by High-Performance Liquid Chromatography," *Methods in Enzymology*, 1980; 66: pp. 452-459.

Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.

Ayers W.A., "Effect of Vitamin B12 and Analogs on the Respiration of a Marine Bacterium," *Archives of Biochemistry and Biophysics*, 1962, vol. 96, pp. 210-215.

Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.

Bavetsias, V., et al., "The design and synthesis of water-soluble analogues of CB30865, a quinazolin-4-one-based antitumor agent," J Med Chem, 2002; 45(17): 3692-3702.

Birinberg E. M. et al., "Synthesis and antimetabolic activity of pyrimidine analogs of folic and pteroic acids," *Pharmaceutical Chemistry Journal*, 1969; 3(6): pp. 331-333.

Bock et al., "Sulfonamide structure-activity relationships in a cell-free system. 2. Proof for the formation of a sulfonamide-containing folate analog," *Journal of Medical Chemistry*, 17: 23-28 (1974).

Boger, D.L. et al., "An improved synthesis of 1,2,9,9a-tetrahydrocyclopropa[c]benz[e]indol-4-one (CBI): a simplified analog of the CC-1065 alkylation subunit," *J. Org. Chem.*, 1992; 57: 2873-2876.

Campbell et al., "Folate-binding protein is a marker for ovarian cancer," *Cancer Res.*, 1991; 51: 5329-5338.

Cho et al., "Single-chain Fv/folate conjugates mediate efficient lysis of folate-receptor-positive tumor cells," *Bioconjug. Chem*. 8(3): 338-346 (1997).

Christensen et al., "Membrane receptors for endocytosis in the renal proximal tubule," *Int. Rev. Cytol.*, 1998; 180: 237-284.

Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.

Citro G. et al., "Inhibition of leukemia cell proliferation by folic acid—polylysine-mediated introduction of c-*myb* antisense oligodeoxynucelotides into HL-60 cells," *Br. J. Cancer*, 1994; 69: 463-467.

Cope A.C. et al., "Thermal Rearrangement of Allyl-type Sulfoxides, Sulfones and Sulfinates," *J. Am. Chem. Soc.*, 1950; 72; 59-67.

Cosulich D.B. et al., "Analogs of Pteroylglutamic Acid. I. N10-Alkylpteroic Acid and Derivatives," *JACS*, 1948, 70 (5), pp. 1922-1926.

DeVita, Jr., Vincent et al (eds); *Biologic Therapy of Cancer*; 2nd ed., J.B. Lippincott Company; 1995.

Domling A. et al., "Myxobacterial Epothilones and Tubulysins as Promising Anticancer Agents," *Molecular Diversity*, 2005; 9: 141-147.

Douglas J.T. et al., "Targeted Gene Delivery by Tropism-Modified Adenoviral Vectors," *Nat. Biotechnol.*, 1996, vol. 14, pp. 1574-1578.

Foong, L.Y. et al., "Development of a Novel Thiol Reagent for Probing Ion Channel Structure: Studies in a Model System," *Biochemistry*, 1997, vol. 36, pp. 1343-1348.

Frankel AE., "Immunotoxin therapy of cancer," *Oncology*, 1993; 7(5): 69-78.

Shealy Y.F., "Synthesis and Evaluation of Some New Retinoids for Cancer Chemoprevention," *Preventive Medicine*, 1989, vol. 18, pp. 624-645.

Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.

Garin-Chesa et al., "Trophoblast and ovarian cancer antigen LK26. Sensitivity and specificity in immunopathology and molecular identification as a folate-binding protein," *Am. J. Pathol*. 142(2): 557-562 (1993).

GE Healthcare, Instructions 71-7104-00 AD.

Gibbs, DD et al., "BGC 945, a novel tumor-selective thymidylate synthase inhibitor targeted to alpha-folate receptor-overexpressing tumors," Cancer Res, 2005; 65(24): 11721-11728.

Gottschalk S. et al., "Folate receptor mediated DNA delivery into tumor cells: potosomal disruption results in enhanced gene expression," *Gene Therapy*, 1994; 1(3): 185-191.

Greene T.E. et al., "Protective Groups in Organic Synthesis," 2d edition, John Wiley & Sons, Inc. New York (1991).

U.S. Appl. No. 60/946,092, filed Jun. 25, 2007, Vlahov et al.

U.S. Appl. No. 60/982,595, filed Oct. 25, 2007, Vlahov et al.

U.S. Appl. No. 61/036,176, filed Mar. 13, 2008, Vlahov et al.

U.S. Appl. No. 61/036,186, filed Mar. 13, 2008, Vlahov et al.

U.S. Appl. No. 12/739,579, filed Apr. 23, 2010, Vlahov et al.

Hanck A.B. et al., "Dexpanthenol (Ro 01-4709) in the treatment of constipation," *Acta Vitaminol Enzymol*, 1982; vol. 4 (1-2), pp. 87-97 (abstract only).

Harvison, P.J. et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.

Henderson, E.A. et al., Targeting the alpha-folate receptor with cyclopenta[g]quinazoline-based inhibitors of thymidylate synthase, Bioorg Med Chem, 2006; 14(14): 5020-5042.

Ho R. I. et al., "A simple radioassay for dihydrofolate synthetase activity in *Escherichia coli* and its application to an inhibition study of new pteroate analogs," *Anal. Biochem.*, 1976, 73(2), pp. 493-500.

Hofland et al., "Folate-targeted gene transfer in vivo," *Mol Ther* 5(6): 739-744 (2002).

Hofle, G. et al., "Semisynthesis and Degradation of the Tubulin Inhibitors Epothilone and Tubulysin", 2003, *Pure Appl. Chem.*, vol. 75, Nos. 2-3, pp. 167-178.

Holladay et al., "Riboflavin-mediated delivery of a macromolecule into cultured human cells," *Biochim Biophys Acta*, 1426(1): 195-204 (1999).

Holm, J. et al., "Folate receptors in malignant and benign tissues of human female genital tract," *BioSci. Rep.*, 17(4): 415-427 (1997).

U.S. Appl. No. 12/775,824, filed May 7, 2010, Green et al.

Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).

Hosomi A. et al., "Affinity for a-tocopherol transfer protein as a determinant of the biological activities of vitamin E analogs," *Federation of European Biochemical Societies Letters*, 1997, vol. 409, pp. 105-108.

Houlihan, C. M. et al., "Preparation and Purification of Pteroic Acid from Folic Acid," *Analytical Biochemistry*, 1972, vol. 46, pp. 1-6.

Hynes et al., "Quinazolines as inhibitors of dihydrofolate reductase. 4. Classical analogues of folic and isofolic acids", *Journal of Medical Chemistry*, 1977; 20: 588-591.

Jackman, A. L. et al., "Antifolates targeted specifically to the folate receptor," Adv Drug Deliv Rev, 2004; 56(8): 1111-1125.

Jones T.R. et al., "A potent antitumour quinazoline inhibitor of thymidylate synthetase: synthesis, biological properties and therapeutic results in mice," *Eur J Cancer*, 1981; 17(1):11-9.

Jones T.R. et al., "Quinazoline antifolates inhibiting thymidylate synthase: variation of the amino acid," *J Med Chem*, 1986; 29(6):1114-8.

Jung K.H. et al., "Intramolecular o-glycoside bond formation," *Chem. Rev*., 2000, 100, 4423-42.

Kagechika H et al., "Synthetic Retinoids: Recent Developments Concerning Structure and Clinical Utility," *Journal of Medicinal Chemistry*, 2005; vol. 48, No. 19, pp. 5875-5883.

Kamen et al., "Delivery of folates to the cytoplasm fo MA104 cells is mediated by a surface receptor that recycles," *J. Biol. Chem.*, 263: 13602-13609 (1988).

Kamen et al., "The folate receptor works in tandem with a probenecid-sensitive carrier in MA104 cells in vitro," *J. Clin. Invest.*, 87(4): 1442-1449 (1991).

Kamen, B. A. et al., "Receptor-mediated folate accumulation is regulated by the cellular folate content," *Proc. Natl. Acad. Sci. USA*, 83: 5983-5987 (1986).

Kandiko C.T. et al., "Inhibition of Rat Brain Pyruvate Dehydrogenase by Thiamine Analogs," *Biochemical Pharmacology*, 1988; vol. 37, No. 22, pp. 4375-4380.

Kane et al., "The influence of extracellular folate concentration on methotrexate uptake by human KB cells. Partial characterization of a membrane-associated methotrexate binding protein," *J. Biol. Chem.*, 261: 44-49 (1986).

Kim et al., "Synthesis and biological activity of 10-thia-10-deaza analogs of folic acid, pteroic acid, and related compounds", *Journal of Medical Chemistry*, 18: 776-780 (1975).

Kranz et al., "Conjugates of folate and anti-T-cell-receptor antibodies specifically target folate-receptor-positive tumor cells for lysis," *Proc. Natl. Acad. Sci. USA*, 1995; 92(20), pp. 9057-9061.

Kumar H.P. et al., "Folate transport in *Lactobacillus salivarius*. Characterization of the transport mechanism and purification and properties of the binding component," *J. Biol. Chem.*. 1987; 262(15):7171-7179.

Ladino et al., "Folate-maytansinoids: target-selective drugs of low molecular weight," *Int. J. Cancer*, 73(6): 859 864 (1997).

Lambooy J. P., "Riboflavin Analogs Utilized for Metabolism by a *Lactobacillus casei* Mutant," *Int. J. Biochem.*, vol. 16, No. 2, 1984, pp. 231-234.

Landuer W. et al., "The Interaction in Teratogenic Activity of the Two Niacin Analogs 3-acetylpyridine and 6-aminonicotinamide," *J Exp Zool*, 151(3):253-258 (1962).

Larock R.C., "Comprehensive Organic Transformations, a guide to functional group preparations," VCH Publishers, Inc. New York (1989).

Leamon CP et al, "Cytotoxicity of folate-*Pseudomonas* exotoxin conjugates toward tumor cells. Contribution of translocation domain," *J. Biol. Chem.* 268(33): 24847-24854 (1993).

Leamon CP et al., "Comparative Preclinical Activity of the Folate-targeted Vinca Alkaloid Conjugates EC140 and EC145," *Int J Cancer*, 2007; 121(7):1585-92.

Leamon CP et al., "Cytotoxicity of momordin-folate conjugates in cultured human cells," *J. Biol. Chem.*, 1992; 267(35): 24966-24971.

U.S. Appl. No. 60/590,580, filed Jul. 23, 2004, Vlahov et al.

U.S. Appl. No. 12/666,712, filed Dec. 24, 2009, Leamon et al.

Leamon CP et al., "Delivery of macromolecules into living cells: a method that exploits folate receptor endocytosis," *Proc. Natl. Acad. Sci. USA* 88(13): 5572-5573 (1991).

Leamon CP et al., "Folate-mediated targeting: from diagnostics to drug and gene delivery," *Drug Discovery Today* 6: 36-43 (2001).

Leamon CP et al., "Folate-targeted chemotherapy," *Adv Drug Deliv Rev*, 2004;56(8): 1127-41.

Leamon CP et al., "Membrane folate-binding proteins are responsible for folate-protein conjugate endocytosis into cultured cells," *Biochem. J.* 291: 855-860 (1993).

Leamon CP et al., "Selective targeting of malignant cells with cytotoxin-folate conjugates," *J. Drug Target.* 2(2): 101-112 (1994).

Leamon CP et al., "Synthesis and biological evaluation of EC140: A novel folate-targeted vinca alkaloid conjugate," *Bioconjug Chem*, 2006;17(5):1226-32.

Leamon CP et al., "Synthesis and Biological Evaluation of EC20: A New Folate-Derived, (99m)Tc-Based Radiopharmaceutical," *Bioconjug. Chem.* 13(6): 1200-1210 (2002).

Leamon CP et al., "Synthesis and biological evaluation of EC72: a new folate-targeted chemotherapeutic," *Bioconjug Chem.*, 2005; 16(4):803-11.

Leamon et al., "Folate-mediated drug delivery: effect of alternative conjugation chemistry," *J. Drug Target* 7(3): 157-169 (1999).

Lee et al, "Measurement of Endosome pH Following Folate Receptor-Mediated Endocytosis," *Biochim. Biophys. Acta* 1312(3): 237-242 (1996).

Lee W.W. et al., "Folic acid antagonists. Methotrexate analogs containing spurious amino acids. Dichlorohomofolic acid," *Journal of Medical Chemistry*, 17: 326-330 (1974).

Lee et al., "Synthesis and evaluation of taxol-folic acid conjugates as targeted antineoplastics," *Bioorg Med Chem.* 10(7): 2397-2414, (2002).

Lee, Francis Y. F., et al., "BMS-247550: A Novel Epothilone Analog With a Mode of Action Similar to Paclitaxel But Possessing Superior Antitumor Efficacy," *Clin Cancer Res*, 2001, No. 7, pp. 1429-1437.

Lee, R. J. and Huang, L., "Folate-Targeted, Anionic Liposome-Entrapped Polylysine-Condensed Dna for Tumor Cell-Specific Gene Transfer," *J. Biol. Chem.* 271(14): 8481-8487 (1996).

Lee, R. J. and Low, P. S, "Delivery of liposomes into cultured KB cells via folate receptor-mediated endocytosis," *J. Biol. Chem.* 269(5): 3198-3204 (1994).

Lee, R. J. and Low, P. S., "Folate-mediated tumor cell targeting of liposome-entrapped doxorubicin in vitro," *Biochim. Biophys. Acta* 1233: 134-144 (1995).

Lemon, Julia, et al., "Conversion of Pterolyglutamic Acid to Pteroic Acid by Bacterial Degradation," *Archives of Biochemistry*, 1948; vol. 19, pp. 311-316.

Levy, Carl C., et al. "The Enzymatic Hydrolysis of Methotrexate and Folic Acid", 1967, *The Journal of Biological Chemistry*, vol. 242, No. 12, pp. 2933-2938.

Lewis et al., "Receptor-mediated folate uptake is positively regulated by disruption of actin cytoskeleton," *Cancer Res.* 58(14): 2952-2956 (1998).

Li et al, "Targeted delivery of antisense oligodeoxynucleotides by LPDII," *J. Liposome Res.* 7(1): 63 (1997).

Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," *J. Org. Chem.* 66: 5655-5663 (2001).

Lonsdale D, "A Review of the Biochemistry, Metabolism and Clinical Benefits of Thiamin(e) and Its Derivatives," publication, Advance Access Publication, vol. 3, Feb. 2006, pp. 49-59.

Lopes et al., "Acyloxymethyl as a drug protecting group. Part 5.1 Kinetics and mechanism of the hydrolysis of tertiary N-acyloxymethylsulfonamides," *J. Chem. Soc.*, Perkin Trans. 2, pp. 431-439 (1999).

Low P.S. et al., "Folate Receptor-Targeted Drugs for Cancer and Inflammatory Diseases," *Adv Drug Deliv Rev*, 2004;56(8):1055-238.

Lu et al., "Folate-targeted enzyme prodrug cancer therapy utilizing penicillin-V amidase and a doxorubicin prodrug," *J. Drug Target*, 7(1): 43-53 (1999).

Lu, J. Y. and Low, P. S., "Folate targeting of haptens to cancer cell surfaces mediates immunotherapy of syngeneic murine tumors," *Cancer Immunol Immunother*, 51: 153-162 (2002).

Lu, J. Y. and Low, P. S., "Folate-mediated delivery of macromolecular anticancer therapeutic agents," *Adv. Drug Del Rev*, 2002; 54(5): 675-693.

Luo et al., "Efficient syntheses of pyrofolic acid and pteroyl azide, reagents for the production of carboxyl-differentiated derivatives of folic acid," *J. Am. Chem. Soc.*, 119: 10004-10013 (1997).

Mack D.O. et al., "The Carboxylation Activity of Vitamin K Analogs with Substitutions at Position 2, 3, or 5," *Journal of Biological Chemistry*, 1979; vol. 254, pp. 2656-2664.

Mancuso A.J. et al., "Activated Dimethyl Sulfoxide: Useful Reagents for Synthesis," *Synthesis*, 1981, pp. 165-184.

March Advanced Organic Chemistry, 1992, John Wiley & Sons, 4th Ed., pp. 362-363, 816, 885, 896.

Mathais et al., "Receptor-mediated targeting of 67Ga-deferoxamine-folate to folate-receptor-positive human KB tumor xenografts," *Nucl Med Biol*, 26(1): 23-25 (1999).

Mathais et al., "Synthesis of [(99m)Tc]DTPA-folate and its evaluation as a folate-receptor-targeted radiopharmaceutical," *Bioconjug Chem*, 11(2): 253-257 (2000).

Mathias et al., "Indium- 111-DTPA-Folate as a potential folate-receptor-targeted radiopharmaceutical," *J. Nucl. Med.*, 39(9): 1579-1585 (1998).

Mathias et al., "Tumor-Selective Radiopharmaceutical Targeting Via Receptor-Mediated Endocytosis of Gallium-67-Deferoxamine-Folate," *J. Nucl. Med*, 37(6): 1003-1008 (1996).

Mathias, C. J., "A kit formulation for preparation of [(111)In]In-DTPA-folate, a folate-receptor-targeted radiopharmaceutical," *Nucl. Med. Biol.*, 25(6): 585-587 (1998).

Matsui et al., "Studies on mitomycins. III. The synthesis and properties of mitomycin derivatives," *J Antibiot*, 21: 189-198 (1968).

Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.

McAlinden TP et al., "Synthesis and Biological Evaluation of a Fluorescent Analogue of Folic Acid," *Biochemistry*, 1991; 30: 5674-81.

McHugh M et al., "Demonstration of a High Affinity Folate Binder in Human Cell Membranes and Its Characterization in Cultured Human KB Cells," *J Biol Chem*, 1979; 254(22):11312-8.

Melani et al., "Targeting of interleukin 2 to human ovarian carcinoma by fusion with a single-chain Fv of antifolate receptor antibody," *Cancer Res*. 58(18): 4146-4154 (1998).

Mislick et al., "Transfection of folate-polylysine DNA complexes: evidence for lysosomal delivery," *Bioconjug. Chem*., 6(5): 512-515 (1995).

Mock D.M. et al., "Urinary Biotin Analogs Increase in Humans During Chronic Supplementation: the Analogs are Biotin Metabolites," *Am J Physiol Endocrinol Metab*, 1997; 272: E83-E85.

Morshed et al., "Folate transport proteins mediate the bidirectional transport of 5-methyltetrahydrofolate in cultured human proximal tubule cells," *J. Nutr*., 127(6): 1137-1147 (1997).

Nair et al., "Folate analogs altered in the C9-N10 bridge region. 14. 11-Oxahomofolic acid, a potential antitumor agent", *Journal of Medical Chemistry*, 23: 59-65 (1980).

Nair et al., "Folate analogs altered in the C9-N10 bridge region. 18. Synthesis and antitumor evaluation of 11-oxahomoaminopterin and related compounds," *Journal of Medical Chemistry*, 24: 1068-1073 (1981).

Nair et al., "Folate analogs altered in the C9-N10 bridge region: N10-tosylisohomofolic acid and N10-tosylisohomoaminopterin," *Journal of Medical Chemistry*, 21: 673-677 (1978).

Nair et al., "Folate analogs altered in the C9-N10 bridge region: 11-thiohomofolic acid," *Journal of Medical Chemistry*, 22: 850-855 (1979).

Nair et al., "Folate analogs. 20. Synthesis and antifolate activity of 1',2',3',4',5',6'-hexahydrohomofolic acid," *Journal of Medical Chemistry*, 26: 135-140 (1983).

Nair et al., "Folate analogs. 21. Synthesis and antifolate and antitumor activities of N10-(cyanomethyl)-5,8-dideazafolic acid," *Journal of Medical Chemistry*, 26: 605-607 (1983).

Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).

Nair et al., "Folate analogues altered in the C9-N10 bridge region. 10-Oxafolic acid and 10-oxaaminopterin," *Journal of Medical Chemistry*, 19: 825-829 (1976).

Neuzil J et al., "Vitamin E Analogs: A New Class of Multiple Action Agents with Anti-Neoplastic and Anti-Atherogenic Activity," *Apoptosis*, 2002; vol. 7, pp. 179-187.

Nielsen P. et al., "Phosphates of Riboflavin and Riboflavin Analogs: A Reinvestigation by High-Performance Liquid Chromatography," *Analytical Biochemistry*, vol. 130, 1983, pp. 359-368.

Nimmo-Smirth R.H. et al., "Some Effects of 2-deaminopteroylglutamic Acid upon Bacterial Growth," *J. Gen. Microbial*., 1953; 9: 536-544.

Nishikawa, Yuji et al., "Growth Inhibition of Hepatoma Cells Induced by Vitamin K and Its Analogs," *Journal of Biological Chemistry*, 1995; vol. 270, No. 47, pp. 28304-28310.

Nomura, Makoto et al., "Development of an Efficient Intermediate α-[2-(Trimethylsilyl)ethoxy]-2-N[2-(trimethylsily1)ethoxycarbonyl1]folic Acid, for the Synthesis of Folate (γ)-Conjugates, and Its Application to the Synthesis of Folate-Nucleoside Congugates," *Journal of Organic Chemistry*, 2000, vol. 65, pp. 5016-5021.

Nosaka K.et al., "Separate Determination of Anticoccidial Thiamine Analogs by High-performance Liquid Chromatography," *ActaA Vitaminol. Et Enzymol*, 1984, vol. 6 (2), pp. 137-142.

Oatis et al., "Synthesis of quinazoline analogues of folic acid modified at position 10," *Journal of Medical Chemistry*, 20: 1393-1396 (1977).

Patrick et al., "Folate Receptors As Potential Therapeutic Targets in Choroid Plexus Tumors of Sv40 Transgenic Mice," *J. Neurooncol*,. 32(2): 111-123 (1997).

Patrick et al., "Intracerebral bispecific ligand-antibody conjugate increases survival of animals bearing endogenously arising brain tumors," *Int. J. Cancer*, 78(4): 470-79 (1998).

Peltier, Hillary M., et al., "The Total Synthesis of Tubulysin D," 2006, *J. Am. Chem. Soc.*, No. 128, pp. 16018-16019.

Pizzorno G., et al., "Intracellular metabolism of 5,10-dideazatetrahydrofolic acid in human leukemia cell lines," *Molecular Pharmacology*, 1991, 39 (1), pp. 85-89.

Plante et al., "Polyglutamyl and polylysyl derivatives of the lysine analogues of folic acid and homofolic acid," *Journal of Medical Chemistry*, 19: 1295-1299 (1976).

Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.

Prabhu V. et al., "*Arabidopsis* dihydropteroate synthase: general properties and inhibition by reaction product and sulfonamides," *Phytochem*., 1997; 45(1): 23-27.

Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.

Pratt, A.G. et al. "The Hydrolysis of Mono-, Di, and Triglutamate Derivatives of Folic Acid With Bacterial Enzymes," *The Journal of Biological Chemistry*, 1968, vol. 243, No. 24, pp: 6367-6372.

Punj, V. et al., "Effect of Vitamin D Analog (1α Hydroxy D5) Immunoconjugated to Her-2 Antibody on Breast Cancer," *Int. J. Cancer*, 2004; 108: 922-929.

Raghavan B et al., "Cytotoxic Simplified Tubulysin Analogues," *J. Med. Chem.*, 2008; 51(6), pp. 1530-1533.

Ranasinghe, M. G. et al.; "A Facile Synthesis of Unsymmetrical Thiolsulfonates via Sulfonylation of Mercaptans," *Synthetic Communications*, 1988; 18(3), pp. 227-232.

Reddy et al., "Optimization of folate-conjugated liposomal vectors for folate receptor-mediated gene therapy," *J. Pharm. Sci*, 88(11): 1112-1118 (1999).

Reddy et al., "Preclinical evaluation of EC145, a folate-vinca alkaloid conjugate," *Cancer Res.*, 2007; 67:4434-42.

Reddy et al., "Retargeting of viral vectors to the folate receptor endocytic pathway," *J Control Release*, 74(1-3): 77-82 (2001).

Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.

Remington: The Science & Practice of Pharmacy, 21th Edition (Lippincott Williams & Wilkins, 2005).

Renz P. et al., "Synthesis of 4-Aza-5, 6-diethylbenzimidazole and Biosynthetic Preparation of 4- and 7-Aza5, 6-dimethylbenzimidazolylcobamide," *Z. Natinforsch*, 1997, vol. 52c, pp. 287-291.

Rijnboutt et al., "Endocytosis of GPI-linked membrane folate receptor-alpha," *J. Cell Biol.*, 132(1-2): 35-47 (1996).

Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).

Roberts et al., "Folic acid analogs. Modifications in the benzene-ring region. 2. Thiazole analogs," *Journal of Medical Chemistry*, 15: 1310-1312 (1972).

Roberts et al., "Folic acid analogs. Modifications in the benzene-ring region. 1. 2'-and 3'-Azafolic acids," *Journal of Medical Chemistry*, 14: 125-130 (1971).

Roberts et al., "Folic acid analogs. Modifications in the benzene-ring region. 4. 3'-Ethyl- and 3'- isopropylfolic acids," *Journal of Medical Chemistry*, 17: 219-222 (1974).

Rose W.C., "Taxol-Based Combination Chemotherapy and Other In Vivo Preclinical Antitumor Studies," *J Natl Cancer Inst Monogr*, 1993, No. 15, pp. 47-53.

Ross et al., "Differential regulation of folate receptor isoforms in normal and malignant tissues in vivo and in established cell lines. Physiologic and clinical implications," *Cancer*, 73(9): 2432-2443, (1994).

Rothberg et al, "Cholesterol controls the clustering of the glycophospholipid-anchored membrane receptor for 5-methyltetrahydrofolate," *J. Cell Biol.*, 111(6): 2931-2938 (1990).

Rothberg et al., "The glycophospholipid-linked folate receptor internalizes folate without entering the clathrin-coated pit endocytic pathway," *J. Cell Biol.*, 110(3): 637-649 (1990).

Roy et al., "targeting T cells against brain tumors with a bispecific ligand-antibody conjugate," *Int. J. Cancer* 76(5): 761-66 (1998).

Sadasivan et al., "The complete amino acid sequence of a human folate binding protein from KB cells determined from the cDNA," J. Biol. Chem., 1989; 264: 5806-5811.

Sargent D.R. et al., "Antimetabolites of Pantothenic Acid, Ureido— and Carbamoyl-Derivatives," *Texas Reports on Biology and Medicine*, 1975, vol. 33, No. 3, pp. 433-443.

Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.

Scott J.M, "Preparation and Purification of Pteroic Acid from Pteroylglutamic Acid (Folic Acid)," *Methods In Enzymology*, 1980, vol. 66, pp: 657-660.

Search Report for Taiwan Patent Application No. 093101735, dated Jul. 14, 2007, 1 page.

Semb J. et al., "Pteroic Acid Derivatives. V. Pteroyl-α-glutamyl-α-glutamylglutamic Acid, Pteroyl-γ- glutamyl-α-glutamylglutamic Acid, Pteroyl-α-glutamyl-γ-glutamylglutamic Acid," *JACS*, 1949; 71 (7): 2310-2315.

Senter et al., "Development of a Drug-Release Strategy Based on the Reductive Fragmentation of Benzyl Carbamate Disulfides," *J. Org. Chem.*, 55: 2975-2978 (1990).

Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.

Shimizu, Kazui, et al., "Novel vitamin D3 antipsoriatic antedrugs: 16-En-22-oxa-1a,25-(OH)2D3 analogs," *Bioorganic & Medicinal Chemistry*, 2006;14: 1838-1850.

Shoup T.M. et al., "Synthesis of Fluorine-18-Labeled Biotin Derivatives: Biodistribution and Infection Localization," *J. Nucl. Med.*, 1994; 35: 1685-1690.

Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.

Smart et al., "Clustered folate receptors deliver 5-methyltetrahydrofolate to cytoplasm of MA104 cells," *J. Cell Biol.*, 134(5): 1169-1177 (1996).

Smart et al., "Protein kinase C activators inhibit receptor-mediated potocytosis by preventing internalization of caveolae," *J. Cell Biol.*, 124(3): 307-313 (1994).

Spry C. et al., "A Class of Pantothenic Acid Analogs Inhibits *Plasmodium falciparum* Pantothenate Kinase and Represses the Proliferation of Malaria Parasites," *Antimicrobial Agents and Chemotherapy*, 2005; 49(11): 4649-4657.

Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).

Steinmetz, H. et al., "Isolation, Crystal and Solution Structure Determination, and Biosynthesis of Tubulysins-Powerful Inhibitors of Tubulin Polymerization from Microbacteria", *Angew. Chem. Int. Ed.*, 2004, No. 43, pp. 4888-4892.

Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.

Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.

Takeda, K. et al., "A Synthesis of a New Type of Alkoxycarbonylating Reagents from 1,1-Bis [6-(trifluoromethyl)benzotriazolyl] Carbonate (BTBC) and Their Reactions," *Sythesis*, 1987; 6: 557-560.

Temple et al., "Synthesis of pseudo cofactor analogs as potential inhibitors of the folate enzymes," *Journal of Medical Chemistry*, 25: 161-166 (1982).

Theti, D. S. et al., "Selective delivery of CB300638, a cyclopenta[g]quinazoline-based thymidylate synthase inhibitor into human tumor cell lines overexpressing the alpha-isoform of the folate receptor," Cancer Res, 2003; 63(13): 3612-3618.

Toffoli et al., "Overexpression of folate binding protein in ovarian cancers," *Int. J. Cancer* 74(2): 193-198 (1997).

Toraya T. et al., "Immobilized Derivatives of Vitamin B12 Coenzyme and Its Analogs," *Methods in Enzymology*, vol. 67, pp. 57-66.

Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.

Trachewsky D., "Antihypertensive Effect of Riboflavin Analogs in Rats with Mineralocorticoid-Induced Hypertension," *Hypertension*, 1981; vol. 3, No. 1, pp. 75-80.

Truneh A. et al., "Temperature-sensitive differential affinity of TRAIL for its receptors. DR5 is the highest affinity receptor," *J Biol Chem*, 2000; 275(30):23319-25.

Turek et al., "Endocytosis of folate-protein conjugates: ultrastructural localization in KB cells," *J. Cell Sci.* 106: 423-430 (1993).

Turk et al., "Characterization of a novel pH-sensitive peptide that enhances drug release from folate-targeted liposomes at endosomal pHs," *Biochim Biophys Acta*, 1559(1): 56-68 (2002).

Ueda M. et al., "Effect of Vitamin B12 Derivatives on Urinary Excretion of Methylmalonic Acid in Liver Diseases," *Acta Med. Okayama*, 1970; vol. 24, pp. 365-372.

Varma, R. et al., "GPI-anchored proteins are organized in submicron domains at the surface," *Nature*, 394(6695): 798-801 (1998).

Verwey, J., "Mitomycin C-Induced Renal Toxicity, a Dose-Dependent Side Effect?," *Eur J Cancer Clin Onco*, 1987; vol. 23, No. 2, pp. 195-199.

Vesely D.L. et al., "Biotin Analogs Activate Guanylate Cyclase," *Molecular and Cellular Biochemistry*, 1984; vol. 60, pp. 109-114.

Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.

Vogel et al., "Peptide-Mediated Release of Folate-Targeted Liposome Contents From Endosomal Compartments," *J. Am. Chem. Soc.*, 1996; 118(7): 1581-1586.

Vyas D. et al., "A practical synthesis of mitomycin A and its analogs," *J Org Chem*, 1986; 31:4307-4309.

Wang et al., "Delivery of antisense oligodeoxyribonucleotides against the human epidermal growth factor receptor into cultured KB cells with liposomes conjugated to folate via polyethylene glycol," *Proc. Natl. Acad. Sci. USA*, 92(8): 3318-3322 (1995).

Wang et al., "Design and synthesis of [111In]DTPA-folate for use as a tumor-targeted radiopharmaceutical," *Bioconjug Chem.*, 8(5): 673-679 (1997).

Wang et al., "Synthesis, purification, and tumor cell uptake of 67Ga-deferoxamine—folate, a potential radiopharmaceutical for tumor imaging," *Bioconj. Chem.*, 1996; 7(1): 56-62.

Wang S. et al., "Folate-mediated targeting of antineoplastic drugs, imaging agents, and nucleic acids to cancer cells," *J. Control Rel*, 1998; 53(1-3): 39-48.

Wang, Xiu-Fang et al., "Vitamin E Analogs Trigger Apoptosis in HER2/erbB2—Overexpressing Breast Cancer Cells by Signaling Via the Mitochondrial Pathway," *Biochemical and Biophysical Research Communication*, 2005; vol. 326, pp. 282-289.

Weinstock et al., "Folic acid analogs. II. p-{[(2,6-Diaminio-8-purinyl)methyl]amino}-benzoyl-L-glutamic acid and related compounds," *Journal of Medical Chemistry*, 13: 995-997 (1970).

Weitman et al., "Cellular localization of the folate receptor: potential role in drug toxicity and folate homeostasis," *Cancer Res.*, 1992; 52(23): 6708-6711.

Weitman et al., "Distribution of the folate receptor GP38 in normal and malignant cell lines and tissues," *Cancer Res.*, 1992; 52(12): 3396-3401.

Westerhof G.R. et al., "Carrier- and Receptor-Mediated Transport of Folate Antagonists Targeting Folate-Dependent Enzymes: Correlates of Molecular-Structure and Biological Activity," *Molecular Pharmacology*, 1995, 48, pp. 459-471.

Westerhof GR et al., "A photoaffinity analogue of folic acid as a probe for the identification and function of a membrane folate binding protein (mFBP) in human CCRF-CEM leukemia cells," *Proccedings of the American Association for Cancer Research*, 1991; 32:328.

Wiener et al., "Targeting dendrimer-chelates to tumors and tumor cells expressing the high-affinity folate receptor," Invest. Radiol. 32(12): 748-54 (1997).

Wu M. et al., "Clustering of GPI-anchored folate receptor independent of both cross-linking and association with caveolin," J. Membr. Biol. 159(2): 137-147 (1997).

Zimmer H. et al., "Potential anticancer agents V., Synthesis of folic acid and pteroic acid analogs derived of caffeine and theophylline,"Arzneimittelforschung, 1966, 16(4), pp. 541-545.

Zimmerman, J., "Folic acid transport in organ-cultured mucosa of human intestine. Evidence for distinct carriers," Gastroenterol. 99(4): 964-972 (1990).

Angier, R. B., et al., "Pteroic Acid Analogs Containing Arsenic," J. American Chem. Soc., vol. 76, 1954, pp. 902-904.

Boothe, J. H., et al., "Pteroic Acid Derivatives. II. Pteroyl-γ-glutamylglutamic Acid and Pteroyl-γ-glutamyl-γ-glutamylglutamic Acid," J. American Chem. Soc., vol. 70, 1948, pp. 1099-1102.

Bartels R. et al., "Determination of pteroic acid by high-performance thin-layer chromatography: Contribution to the investigation of 7,8-dihydropteroate synthase," Journal of Chromatography A, 1994; vol. 659(1): 185-189 (abstract only).

Wikipedia, Derivative (Chemistry), http://en.wikipedia.org/wiki/Derivative_(chemistry), downloaded Dec. 16, 2009.

Wikipedia, Analog (Chemistry), http://en.wikipedia.org/wiki/Analog_(chemistry), downloaded Dec. 16, 2009.

Wikipedia, List of Purification Methods in Chemistry, http://en.wikipedia.org/wiki/List_of_purification_methods_in_chemistry, downloaded Dec. 16, 2009.

Wikipedia, Solution, http://en.wikipedia.org/wiki/Solution, downloaded Dec. 17, 2009.

Principles of Ion Exchange Chromatography, http://www.separations.us.tosohbioscience.com/ServiceSupport/TechSupport/ResourceCenter/PrinciplesofChmatography/IonExchange, downloaded Dec. 23, 2009.

Wikipedia, Conjugate, http://en.wikipedia.org/wiki/Conjugate, downloaded Dec. 17, 2009.

Wikipedia, Complex (Chemistry), http://en.wikipedia.org/wiki/Complex_(chemistry), downloaded Dec. 23, 2009.

Leamon Christopher P., "Aspects of Folate-Mediated Drug Delivery . . . Beyond Purdue" PowerPoint Presentation presented at Purdue University on May 4, 1999, (22 pages).

Achilefu et al. "A New Method for the Synthesis of Tri-tert-butyl Diethylenetriaminepentaacetic Acid Its Derivatives" J. Org. Chem. 2000;65:1562-1565.

Carl et al. "A novel connector linkage applicable in prodrug design" J. Med. Chem. 1981;24(5):479-480.

Coney et al. "Cloning of a tumor-associated antigent: MOv18 and MOv19 antibodies recognize a folate-binding protein" Cancer Res. 1991;51(22):6125-32.

Crapatureanu et al. "Molecular necklaces. Cross-linking hemoglobin with reagents containing covalently attached ligands" Bioconjugate Chemistry, 1999;10(6):1058-67.

Darnell, Ed. Molecular Cell Biology W. H. Freeman, San Francisco 1990;326-333.

DeNardo, Gerald. "When is Too Much Too Much and Yet Not Enough? Alas, a Plethora of Opportunities but Where's the Beef?" J. of Nuclear Medicine 2000; 41(3):470-3.

Dorwald, F. Z., "Side Reactions in Organic Synthesis: A Guide to Successful Synthesis Design," Wiley-VCH, Weinheim, 2005, p. ix of preface.

Forgac. "Structure and function of vacuolar class of ATP-driven pumps" Physiological Rev. 1989; 69(3):765-795.

Garrett et al. "Synthesis and characterisation of polyamine-poly(ethylene glycol) constructs for DNA binding and gene delivery" Bioorganic & Medicinal Chemistry, 2000; 8(7):1779-1797.

Henderson et al. "Mediated uptake of folate by a high-affinity binding protein in sublines of L1210 cells adapted to nanomolar concentrations of folate" J. Membrane Biol., 1988;101:247-258.

Huang et al. "Design, syntheses and sequence selective DNA cleavage of functional models of bleomycin-II. 1,2 -trans-di substituted cyclopropane units as novel linkers" Bioorganic & Medicinal Chemistry, 1995;3(6):647-57.

Jansen et al., "Identification of a Membrane-Associated Folate-Binding Protein in Human Leukemic CCRF-CEM Cells with Transport-Related Methotrexate Resistance"in Cancer Res., 1989, 49, 2455-2459.

Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.

Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.

Kamen et al., 1986, "Receptor-mediated folate accumulation is regulated by cellular folate content" Proc. Natl. Acad. Sci., U.S.A. 83, 5983-5987.

Ke et al. "Targeting the Tumor-Associated Folate Receptor with a 111-IN-DTPA Conjugate of Pteroic Acid" Abstract No. 427. 48'h Annual Meeting of the Society of Nuclear Medicine Toronto, Canada, Jun. 26, 2001, available May 4, 2001; 1 pg.

Kemp et al. "New Protective Groups for Peptide Synthesis-I The Bic Group Base and Solvent Lability of the 5 -B enzi soxazolymethyl eneoxycarbonyl amino function" 'Tet. Lett. 1975;52:4625-4628.

Kutsky RJ. Handbook of Vitamins, Minerals, and Hormones, 2nd Edition. New York: Van Nostrand Reinhold: 1981;263-277.

Lee et al. "Prolonged circulating lives of single-chain Fv proteins conjugated with polyethylene glycol: a comparison of conjugation chemistries and compounds" Bioconjugate Chemistry, 1999;10(6):973-81.

Li et al. "Local concentration of folate binding protein GP38 in sections of human ovarian carcinoma by concentration of in vitro quantitative autoradiography." J. Nucl. Med. 1996; 37:665-672.

Linder et al., In vitro & in vivo studies with a-and y-isomers of 99'Tc-oxa folate show uptake of both isomers in folate receipt (+) KB Cell Lines J. Nuclear Med. 2000;41(5):470 Suppl.

Mehvar R "Dextrans for targeted and sustained delivery of therapeutic and imaging agents" [Review] Journal of Controlled Release, 2000;69(1):1-25.

Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.

Miotti et al., "Characterization of Human Ovarian Carcinoma—Associated Antigens Defined by Novel Monoclonal Antibodies with Tumor—Restricted Specificity" Int. J. Cancer, 1987;39:297-303.

Pastan et al, eds. "The Pathways of Endocytosis" Endocytosis, Plenum Press, New York 1985;1-40.

Peterson et al. "Enzymatic cleavage of peptide-linked radiolabels from immunoconjugates" Bioconjugate Chemistry, 1999;10(4):553-7.

Pizzorno et al. "5,10-Dideazatetrahydrofolic acid (DDATHF) transport in CCRFCEM and MA104 cell lines." J. Biol, Chem., 1993; 268(2):247-258.

Rothenberg et al. "Further observations on the folate-binding factor in some leukemic cells" J. Clin. invest. 1971; 50(3):719-726.

Selhub et al. "The folate binding protein of rat kidney. Purification, properties, and cellular distribution" J. Biol. Chem. 1984;259(10):6601-6606.

Selhub et al. "Renal folate adsorption and the kidney folate binding protein I. Urinary Clearance studies" Am. J Physiol. 252:F750-F756.

Selhub et al. "Renal folate adsorption and the kidney folate binding protein II. Microinfusion studies" Am. J. Physiol. 252:F757-F760.

Sirotnak. "Obligate genetic expression in tumor cells of a fetal membrane property mediating "Folate" transport: biological significance and implications for improved therapy of human cancer" Cancer Res., 1985;45(9):3992-4000.

Stein et al. "Normal tissue reactivity of four anti-tumor monoclonal antibodies of clinical interest" Int. J. Cancer 1991;47(2):163-169.

Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3),922-9.

Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94.

Toffoli et al. "Expression of folate binding protein as a prognostic factor for response to platinum-containing chemotherapy and survival in human ovarian cancer" Int. J. Cancer (Pred. Oncol) 1998; 79:121-126.

Westerhof et al. "Membrane transport of natural folates and antifolate compounds in murine L1210 Leukemia cells: role of carrier-and receptor mediated transport systems" Cancer Res. 1991;51:5507-5513.

Williams et al. "Renal tubular transport of folic acid and methotrexate in the monkey" Am. J. Physiol 1982; 242(5):F484-490.

Weygand, et al., Chemishe. Berichte (1950) 83, 460-467.

Beevers, Christopher S., et al., "Curcumin Inhibits the Mammalian Target of Rapamycin-Mediated Signaling Pathways in Cancer Cells", 2006; Int. Journal Cancer; Vo. 119; pp. 757-764.

Brown, Nicole E., et al., "Delayed Cystogenesis and Increased Ciliogenesis Associated with th Re-Expression of Polaris in Tg737 Mutant Mice", 2003, Kidney International, vol. 63, pp. 1220-1229.

Bukanov Nikolay, O. et al., "Long-Lasting Arrest of Murine Polycystic Kidney Disease With CDK Inhibitor Roscovitine", Dec. 14, 2006; Nature; vol. 444; pp. 949-952.

Hay, Nissim, et al., "Upstream and Downstream of mTOR", 2004, Genes & Development, vol. 18, No. 16, pp. 1926-1945.

Kennedy, Michael D., et al., "Evaluation of Folate Conjugate Uptake and Transport by the Choroid Plexus of Mice", (May 2003), vol. 20, No. 5, pp: 714-719.

Leamon, Christopher P., et al., "Folate-Liposome-Mediated Antisense Oligodeoxynucleotide Targeting to Cancer Cells: Evaluation in Vitro and in Vivo", 2003, Bioconjugate Chemistry, vol. 14, No. 4, pp. 738-747.

Nauta, Jeroen, et al., "Renal and Biliary Abnormalities in a New Murine Model of Autosomal Recessive Polycystic Kidney Disease", 1993, Pediatr. Nephrol. No. 7, pp. 163-172.

Piontek, Klaus B., et al. "A Functional Floxed Allele of $Pkd1$ that Can Be Conditionally Inactivated In Vivo", J. Am. Soc. Nephrol. vol. 15, pp. 3035-3043.

Shillingford, Jonathan M., et al., "The mTOR Pathway is Regulated by Polycystin-1, and its Inhibition Reverses Renal Cystogenesis in Polycyctic Kidney Disease", Apr. 4, 2006, PNAS. vol. 103, No. 14, pp. 5466-5471.

Ke CY et al., "Folate-Receptor-Targeting of In-111 Using Pteroic Acid Conjugates of Benzyl-DTPA and Benzyl-DOTA," J. Nucl. Med., 2004; 45(5):457P.

Regueiro-Ren et al., "Synthesis and Biological Activity of Novel Epothilone Aziridines," Organic Letters, 2001; vol. 3, No. 17: 2693-96.

Kamen et al., "A review of folate receptor alpha cycling and 5-methyltetrahydrofolate accumulation with an emphasis on cell models in vitro," Advanced Drug Delivery Reviews, 2004; vol. 56:1085-97.

Elnakat et al., "Distribution, functionality and gene regulation of folate receptor isoforms: implications in targeted therapy," Advanced Drug Delivery Reviews, 2004; vol. 56:1067-84.

Sabharanjak et al., "Folate receptor endocytosis and trafficking," Advanced Drug Delivery Reviews, 2004; vol. 56: 1099-1109.

Paulos et al., "Folate receptor-mediated targeting of therapeutic and imaging agents to activated macrophages in rheumatoid arthritis," Advanced Drug Delivery Reviews, 2004; vol. 56: 1205-17.

Antony, "Folate receptors: reflections on a personal odyssey and a perspective on unfolding truth," Advanced Drug Delivery Reviews, 2004; vol. 56: 1059-66.

Lu et al., "Folate receptor-targeted immunotherapy of cancer: mechanism and therapeutic potential," Advanced Drug Delivery Reviews, 2004; vol. 56: 1161-76.

Roy et al., "Folate-mediated targeting of T cells to tumors," Advanced Drug Delivery Reviews, 2004; vol. 56: 1219-31.

Ke et al., "Folate-receptor-targeted radionuclide imaging agents," Advanced Drug Delivery Reviews, 2004; vol. 56: 1143-60.

Gabizon et al., "Tumor cell targeting of liposome-entrapped drugs with phospholipid-anchored folic acid—PEG Conjugates," Advanced Drug Delivery Reviews, 2004; vol. 56: 1177-92.

Zhao et al., "Tumor-selective targeted delivery of genes and antisense oligodeoxyribonucleotides via the folate receptor," Advanced Drug Delivery Reviews, 2004; vol. 56: 1193-1204.

Paulos CM et al., "Ligand Binding and Kinetics of Folate Receptor Recycling in Vivo: Impact on Receptor-Mediated Drug Delivery," Molecular Pharmacology, 2004; 66:1406-1414.

Griesser UJ, "The Importance of Solvents," in Polymorphism in the Pharmaceutical Industry, Hilfiker ed., 2006; p. 211-230.

Wikipedia, Structural analog, http://en.wikipedia.org/wiki/Structural_analog, downloaded Apr. 7, 2009.

Wikipedia, Functional analog, http://en.wikipedia.org/wild/Functional_analog, downloaded Apr. 7, 2009.

Wikipedia, Folic acid, http://en.wikipedia.org/wiki/Folic_acid, downloaded Apr. 7, 2009.

Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.

Atkinson SF et al., "Conjugation of folate via gelonin carbohydrate residues retains ribosomal-inactivating properties of the toxin and permits targeting to folate receptor positive cells," Journal of Biological Chemistry, 2001; 276(30):27930-27935.

Matulic-Adamic J et al., "An efficient synthesis of the ribozyme-folate conjugate," Tetrahedron Letters, 2002; 43(25):4439-4441.

Harrison JG et al., "A convenient synthetic route to oligonucleotide conjugates," Bioorganic & Medicinal Chemistry Letters, 1997; 7(8): 1041-1046.

Dyson G., May P. "The Chemistry of Synthetic Pharmaceutical Substances", translation from English M.:-"The World", 1964, pp. 12-19.

Mashkovskiy M.D. Drugs, Moscow, New wave, 2001, vol. I, p. 11.

Robert Laplanche, et al.,"Physiologically Based Pharmacokinetic (PBPK) Modeling of Everolimus (RAD001) in Rats Involving Non-Linear Tissue Uptake,"Journal of Pharmacokinetics and Pharmacodynamics, 2007, vol. 34, No. 3, 373-400.

Pathalk et al., Enzymic protecting group techniques in organic synthesis, Stereosel. Biocatal. 775-797 (2000).

Dube D et al., "Preparation and Tumor Cell Uptake of Poly(N-isopropylacrylamide) Folate Conjugates"; Bioconjugate Chem, 2002; 13: 685-692.

Evans et al., "Synthessis of biotin conjugates of the antifungal compound cymoxanil," Pest Manag Sci, 2002; 58: 392-396.

Rao et al., Journal of Medicinal Chemistry, 1985, 28:1079-1088.

Conrad et al, Journal of Medicinal Chemistry, 1979, 22(4): 391-400.

Golub, T.R., et al., "Molecular Classification of Cancer: Class Discovery and Class Prediction by Gene Expression Monitoring," Science, 1999, vol. 286, 531-537 (Oct. 15, 1999).

Speckamp, et al.; "New Developments in the Chemistry of N-Acyliminium Ions and Related Intermediates" Tetrahedron 2000 vol. 56(24) 3817-3856.

Angier et al., Science, 1946, 103: 667-669.

Wolf et al., Journal of the American Chemical Society, 1947, 69: 2753-2759.

Parker et al., "Folate receptor expression in carcinomas and normal tissues determined by a quantitative radioligand binding assay," Analytical Biochemistry, 2005; 335:284-293.

U.S. Appl. No. 13/609,995, filed Sep. 11, 2012, Vlahov et al.

U.S. Appl. No. 13/507,076, filed Jun. 1, 2012, Leamon et al.

* cited by examiner

MULTI-DRUG LIGAND CONJUGATES

CROSS-REFERENCE TO RELATED APPLICATIONS

This application is a U.S. national application under 37 C.F.R. §371(b) of International Application Serial No. PCT/US2006/032561 filed Aug. 18, 2006, which claims the benefit under 35 U.S.C. §119(e) of U.S. provisional patent application Ser. No. 60/709,950, filed Aug. 19, 2005, and U.S. provisional patent application Ser. No. 60/787,558, filed Mar. 30, 2006, the entirety of the disclosures of which are incorporated herein by reference.

TECHNICAL FIELD

The present invention relates to compositions and methods for use in targeted drug delivery. In particular, the invention relates to ligand conjugates including two or more drugs, and analogs and derivatives thereof, such as conjugates of vitamin receptor binding compounds and two or more drugs.

BACKGROUND

The mammalian immune system provides a means for the recognition and elimination of tumor cells, other pathogenic cells, and invading foreign pathogens. While the immune system normally provides a strong line of defense, there are many instances where cancer cells, other pathogenic cells, or infectious agents evade a host immune response and proliferate or persist with concomitant host pathogenicity. Chemotherapeutic agents and radiation therapies have been developed to eliminate, for example, replicating neoplasms. However, many of the currently available chemotherapeutic agents and radiation therapy regimens have adverse side effects because they work not only to destroy pathogenic cells, but they also affect normal host cells, such as cells of the hematopoietic system. The adverse side effects of these anti-cancer drugs highlight the need for the development of new therapies selective for pathogenic cell populations and with reduced host toxicity.

Researchers have developed therapeutic protocols for destroying pathogenic cells by targeting cytotoxic compounds to such cells. Many of these protocols utilize toxins conjugated to antibodies that bind to antigens unique to or overexpressed by the pathogenic cells in an attempt to minimize delivery of the toxin to normal cells. Using this approach, certain immunotoxins have been developed consisting of antibodies directed to specific antigens on pathogenic cells, the antibodies being linked to toxins such as ricin, Pseudomonas exotoxin, Diptheria toxin, and tumor necrosis factor. These immunotoxins target pathogenic cells, such as tumor cells, bearing the specific antigens recognized by the antibody (Olsnes, S., *Immunol. Today*, 10, pp. 291-295, 1989; Melby, E. L., *Cancer Res.*, 53(8), pp. 1755-1760, 1993; Better, M. D., PCT International Publication no. WO 91/07418, published May 30, 1991).

Another approach for targeting populations of pathogenic cells, such as cancer cells or foreign pathogens, in a host is to enhance the host immune response against the pathogenic cells to avoid the need for administration of compounds that may also exhibit independent host toxicity. One reported strategy for immunotherapy is to bind antibodies, for example, genetically engineered multimeric antibodies, to the surface of tumor cells to display the constant region of the antibodies on the cell surface and thereby induce tumor cell killing by various immune-system mediated processes (De Vita, V. T., *Biologic Therapy of Cancer*, 2d ed. Philadelphia, Lippincott, 1995; Soulillou, J. P., U.S. Pat. No. 5,672,486). However, these approaches have been complicated by the difficulties in defining tumor-specific antigens.

SUMMARY OF THE INVENTION

Ligand conjugates of drugs, and analogs and derivatives thereof, are described herein. The conjugates include cell receptor binding ligands that are covalently attached to two or more drugs that may be targeted to cells. The conjugates described herein may also include a polyvalent linker for attaching the ligands to the drugs.

In one embodiment, a receptor binding drug delivery conjugate is described. The drug delivery conjugate comprises a ligand of a cell surface receptor, two or more drugs, or analogs or derivatives thereof, and optionally a polyvalent linker, which may be generally represented by the formula $$(B)-(L)-(D)_n$$

wherein (B) represents a receptor binding moiety; (D) represents a drug, or analog or derivative thereof, to be targeted to a cell by the receptor binding moiety; (L) represents a polyvalent linker, and n is an integer greater than 1. The polyvalent linker (L) can comprise multiple linkers covalently attached to each other. For example, the polyvalent linker (L) can comprise one or more spacer linkers ($l_s$), and/or releasable linkers ($l_r$), each connected to the other, and to the ligand and the drug, by one or more heteroatom linkers ($l_H$). These various linkers may be selected and placed in any order to construct the polyvalent linker (L). Illustratively, the polyvalent linker (L) may be constructed from one or more of the following bivalent linkers:

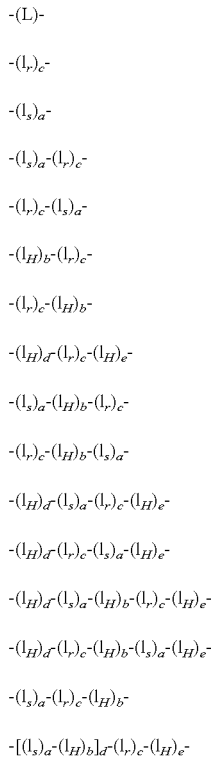

wherein a, b, c, d, and e are integers, such as integers in the range from 0 to about 4, and ($l_s$), ($l_H$), and ($l_r$) are the spacer linkers, releasable linkers, heteroatom linkers, respectively. Additional illustrative examples of bivalent linkers that may be used to construct the polyvalent linkers described herein are described in U.S. patent application Ser. No. 10/765,336 (also found as U.S. patent application publication no. US 2005/0002942 A1) and PCT international publication no. WO 2006/012527, the entirety of the disclosures of which are incorporated herein by reference.

It is to be understood that the polyvalent linkers may connect the receptor binding moiety to the two or more drugs in a variety of structural configurations, including but not limited to the following illustrative general formulae:

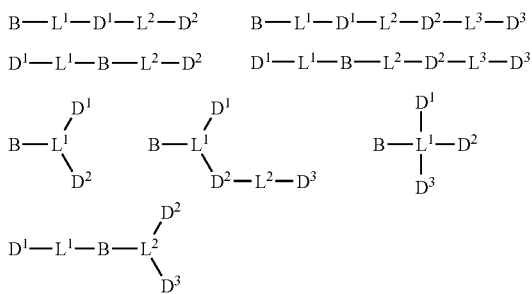

where B is the receptor binding ligand, each of ($L^1$), ($L^2$), and ($L^3$) is a polyvalent linker constructed from one or more spacer, releasable, and/or heteroatom linkers, and each of ($D^1$), $D^2$, and $D^3$ is a drug, or an analog or derivative thereof. Other variations, including additional drugs, or analogs or derivatives thereof, additional linkers, and additional configurations of the arrangement of each of (B), (L), and (D), are also contemplated herein.

In one variation, more than one receptor binding ligand is included in the drug delivery conjugates described herein, including but not limited to the following illustrative general formulae:

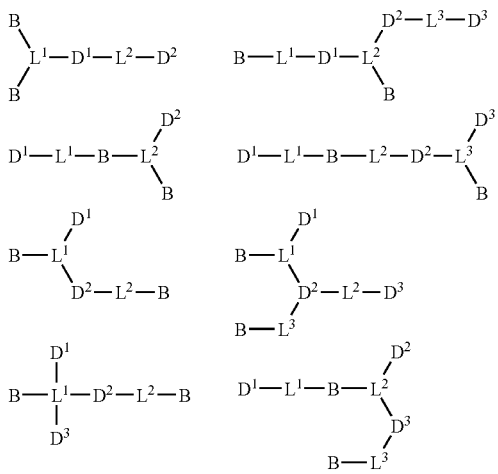

where each B is a receptor binding ligand, each of ($L^1$), ($L^2$), and ($L^3$) is a polyvalent linker constructed from one or more spacer, releasable, and/or heteroatom linkers, and each of ($D^1$), $D^2$, and $D^3$ is a drug, or an analog or derivative thereof. Other variations, including additional drugs, or analogs or derivatives thereof, additional linkers, and additional configurations of the arrangement of each of (B), (L), and (D), are also contemplated herein. In one variation, the receptor binding ligands are for the same receptor, and in another variation, the receptor binding ligands are for different receptors.

In one illustrative embodiment of the drug delivery conjugates described herein, the polyvalent linker includes at least one releasable linker ($l_r$). In another illustrative embodiment of the drug delivery conjugates described herein, the polyvalent linker includes at least two releasable linkers ($l_r$)$_2$. In another illustrative aspect, the polyvalent linker (L) includes at least one releasable linkers ($l_r$) that is not a disulfide releasable linker. In another illustrative aspect, the polyvalent linker (L) has at least two releasable linkers ($l_r$)$_2$ where one releasable linker is not a disulfide releasable linker. It is appreciated that when more than one releasable linker is included in the polyvalent linker, those releasable linkers may be adjacent. It is further appreciated that when two releasable linkers are adjacent in the polyvalent linker, the two releasable linkers may cooperate to cause release of the drug.

In another embodiment, the polyvalent linker includes at least one spacer linker that is a peptide formed from amino acids. In one aspect, the peptide includes naturally occurring amino acids, and stereoisomers thereof. In another aspect, the peptide is formed only from naturally occurring amino acids, and stereoisomers thereof.

The ligands described herein generally include ligands of cell surface receptors. Illustrative ligands useful in the conjugates described herein include, but are not limited to, vitamins, and other moieties that bind to a vitamin receptor, transporter, or other surface-presented protein that specifically binds vitamins, or analogs or derivatives thereof, peptide ligands identified from library screens, tumor cell-specific peptides, tumor cell-specific aptamers, tumor cell-specific carbohydrates, tumor cell-specific monoclonal or polyclonal antibodies, Fab or scfv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selectins, steroid hormones, Arg-Gly-Asp containing peptides, retinoids, various Galectins, δ-opioid receptor ligands, cholecystokinin A receptor ligands, ligands specific for angiotensin AT1 or AT2 receptors, peroxisome proliferator-activated receptor λ ligands, β-lactam antibiotics such as penicillin, small organic molecules including antimicrobial drugs, and other molecules that bind specifically to a receptor preferentially expressed on the surface of tumor cells or on an infectious organism, antimicrobial and other drugs designed to fit into the binding pocket of a particular receptor based on the crystal structure of the receptor or other cell surface protein, ligands of tumor antigens or other molecules preferentially expressed on the surface of tumor cells, or fragments of any of these molecules. Tumor-specific antigens that could function as a binding site for ligand-drug conjugates include extracellular epitopes of members of the Ephrin family of proteins, such as EphA2. EphA2 expression is restricted to cell-cell junctions in normal cells, but EphA2 is distributed over the entire cell surface in metastatic tumor cells. Thus, EphA2 on metastatic cells would be accessible for binding to, for example, an Fab fragment of an antibody conjugated to a drug, or analog or derivative thereof, whereas the protein would not be accessible for binding to the Fab fragment on normal cells, resulting in a ligand-drug conjugate specific for metastatic cancer cells.

The drugs, and various analogs and derivatives thereof, described herein are generally drugs for eliminating, killing, interfering with, and/or decreasing the growth of a population of pathogenic cells, including infectious agents, cancers, tumors, and the like. Further, the drugs, and the various analogs and derivatives thereof, useful in the conjugates described herein may have a wide variety of mechanisms of action, including but not limited to alkylating agents, microtubule inhibitors, including those that stabilize and/or destabilize microtubule formation, including beta-tubulin agents, cyclin dependent kinase (CDK) inhibitors such as CDKN1a. CDKN1b, and the like, topoisomerase inhibitors, protein synthesis inhibitors, protein kinase inhibitors, including Ras, Raf, PKC, PI3K, and like inhibitors, transcription inhibitors, antifolates, heat shock protein blockers, and the like.

In another embodiment, a pharmaceutical composition is described. The pharmaceutical composition comprises a drug delivery conjugate described herein in combination with a pharmaceutically acceptable carrier, excipient, and/or diluent therefor.

In another embodiment, a method for eliminating a population of pathogenic cells in a host animal harboring the population of pathogenic cells is described. In one illustrative aspect, the members of the pathogenic cell population have an accessible binding site for a receptor binding moiety, or the analog or derivative thereof, and that binding site is uniquely expressed, overexpressed, or preferentially expressed by the pathogenic cells. The method includes the step of administering to the host a drug delivery conjugate described herein, or a pharmaceutical composition thereof, as described herein.

DETAILED DESCRIPTION

Figure 1A:
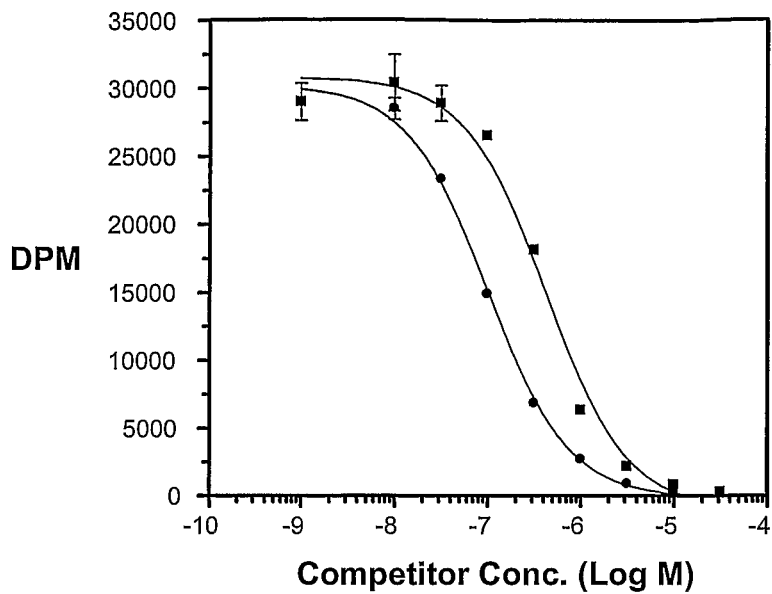
FIG. 1A shows the relative binding affinity of Example 9 (■, 0.24) versus folic acid (●, 1.0) at folic acid receptors.

Ligand conjugates of drugs, and analogs and derivatives thereof, are described herein. The conjugates include cell receptor binding ligands, including ligands of cell surface receptors, that are covalently attached to two or more drugs that may be targeted to cells, including pathogenic cells. The conjugates described herein may also include a polyvalent linker for attaching the ligands to the drugs.

Receptor binding drug delivery conjugates comprising a receptor binding moiety (B), a polyvalent linker (L), and two or more drugs, or drug analogs or drug derivatives, $(D)_n$ are described, where n is greater than or equal to 2. In the delivery conjugates described herein, the receptor binding moiety (B) and the two or more drugs $(D)_n$ are each bound to the polyvalent linker (L), through an independently selected heteroatom linker ($l_H$). The polyvalent linker (L) comprises one or more spacer linkers, heteroatom linkers, and releasable linkers, and combinations thereof, in any order.

In one embodiment, a receptor binding drug delivery conjugate is described. The drug delivery conjugate comprises a ligand, such as a ligand of a cell surface receptor, two or more drugs, or analogs or derivatives thereof, and optionally a polyvalent linker, which may be generally represented by the formula (B)-(L)-(D)$_n$ wherein (B) represents a receptor binding moiety; (D) represents a drug, or analog or derivative thereof, to be targeted to a cell by the receptor binding moiety; (L) represents a polyvalent linker, and n is an integer greater than 1. The polyvalent linker (L) can comprise multiple linkers covalently attached to each other. For example, the polyvalent linker (L) can comprise one or more spacer linkers ($l_s$), and/or releasable linkers ($l_r$), each connected to the other, and to the ligand and the drug, by one or more heteroatom linkers ($l_H$). These various linkers may be selected and placed in any order to construct the polyvalent linker (L).

Illustratively, the polyvalent linker (L) may be constructed from one or more of the following bivalent linkers:

-(L)- 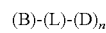

-($l_r$)$_c$- 

-(l_s)_a-

-(l_s)_a-(l_r)_c-

-(l_r)_c-(l_s)_a-

-(l_H)_b-(l_r)_c-

-(l_r)_c-(l_H)_b-

-(l_H)_d-(l_r)_c-(l_H)_e-

-(l_s)_a-(l_H)_b-(l_r)_c-

-(l_r)_c-(l_H)_b-(l_s)_a-

-(l_H)_d-(l_s)_a-(l_r)_c-(l_H)_e-

-(l_H)_d-(l_r)_c-(l_s)_a-(l_H)_e-

-(l_H)_d-(l_s)_a-(l_H)_b-(l_r)_c-(l_H)_e-

-(l_H)_d-(l_r)_c-(l_H)_b-(l_s)_a-(l_H)_e-

-(l_s)_a-(l_r)_c-(l_H)_b-

-[(l_s)_a-(l_H)_b]_d-(l_r)_c-(l_H)_e- wherein a, b, c, d, and e are integers, such as integers in the range from 0 to about 4, and ($l_s$), ($l_H$), and ($l_r$) are the spacer linkers, releasable linkers, heteroatom linkers, respectively. Additional illustrative examples of bivalent linkers that may be used to construct the polyvalent linkers described herein are described in U.S. patent application Ser. No. 10/765,336 (also found as U.S. patent application publication no. US 2005/0002942 A1) and PCT international publication no. WO2006/012527, the entirety of the disclosures of which are incorporated herein by reference.

It is to be understood that the polyvalent linkers may connect the receptor binding moiety to the two or more drugs in a variety of structural configurations, including but not limited to the following illustrative general formulae:

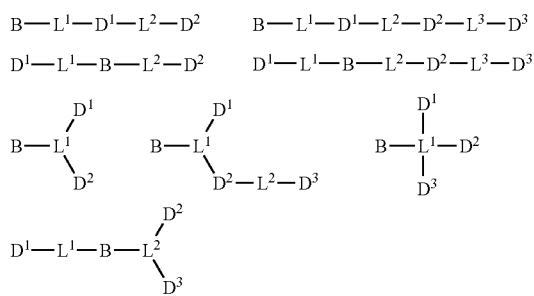

where B is the receptor binding ligand, each of ($L^1$), ($L^2$), and ($L^3$) is a polyvalent linker constructed from one or more spacer, releasable, and/or heteroatom linkers, and each of ($D^1$), $D^2$, and $D^3$ is a drug, or an analog or derivative thereof. Other variations, including additional drugs, or analogs or derivatives thereof, additional linkers, and additional configurations of the arrangement of each of (B), (L), and (D), are also contemplated herein.

In one variation, more than one receptor binding ligand is included in the drug delivery conjugates described herein, including but not limited to the following illustrative general formulae:

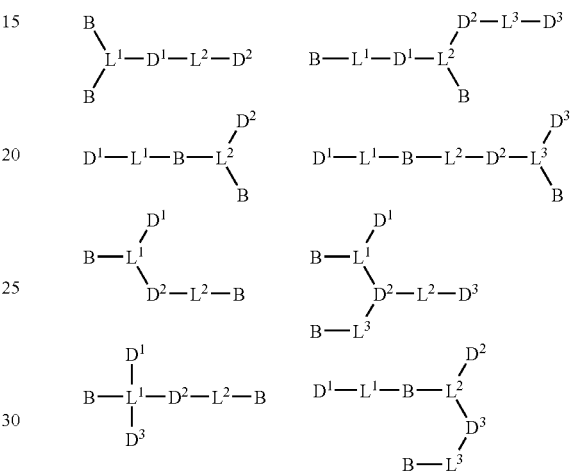

where each B is a receptor binding ligand, each of ($L^1$), ($L^2$), and ($L^3$) is a polyvalent linker constructed from one or more spacer, releasable, and/or heteroatom linkers, and each of ($D^1$), $D^2$, and $D^3$ is a drug, or an analog or derivative thereof. Other variations, including additional drugs, or analogs or derivatives thereof, additional linkers, and additional configurations of the arrangement of each of (B), (L), and (D), are also contemplated herein. In one variation, the receptor binding ligands are for the same receptor, and in another variation, the receptor binding ligands are for different receptors. It is appreciated, and as shown in the above formulae, that more than one polyvalent linker may be included in the drug delivery conjugates described herein. It is understood that in one aspect, the number of linkers are selected depending upon the configuration of the receptor binding ligands, and the drugs.

For example, in one illustrative embodiment of the manner in which linkers are covalently assembled to form the polyvalent linker, or part of the polyvalent linker, heteroatom linkers, spacer linkers, and releasable linkers are connected to form a polyvalent group of the formula:

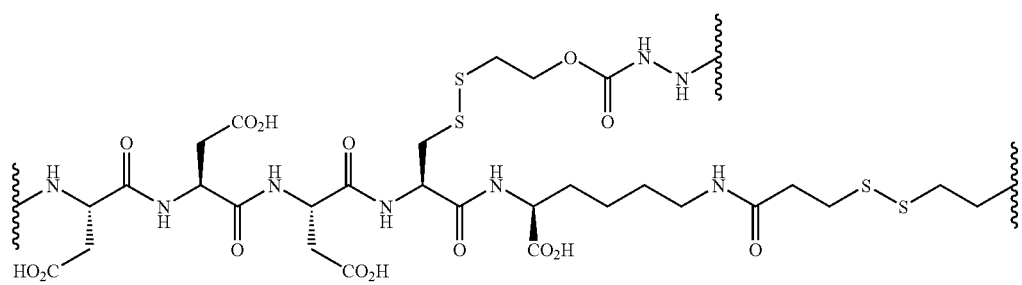 [SMILES: *CCSSCCC(=O)NCCCC[C@H](NC(=O)[C@H](CSSCCOC(=O)NN*)NC(=O)[C@H](CC(=O)O)NC(=O)[C@H](CC(=O)O)NC(=O)[C@H](CC(=O)O)N*)C(=O)O]

where the formula may also be represented as

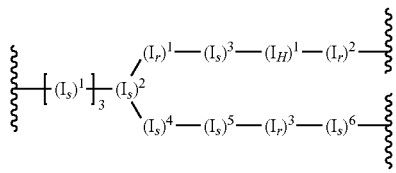

wherein $(l_s)^1$ is the tripeptide Asp-Asp-Asp, $(l_s)^2$ is Cys, $(l_r)^1$ is S—S, $(l_s)^3$ is $CH_2CH_2$, $(l_H)^1$ is O, $(l_r)^2$ is C(O)NHNH, $(l_s)^4$ is ω-Lys, $(l_s)^5$ is C(O)CH2CH2, $(l_r)^3$ is S—S, and $(l_s)^6$ is $CH_2CH_2$.

The ligands of cell surface receptors useful in the conjugates described herein include, but are not limited to, vitamins, and other moieties that bind to a vitamin receptor, transporter, or other surface-presented protein that specifically binds vitamins, or analog or derivative thereof, peptide ligands identified from library screens, tumor cell-specific peptides, tumor cell-specific aptamers, tumor cell-specific carbohydrates, tumor cell-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selectins, steroid hormones, Arg-Gly-Asp containing peptides, retinoids, various Galectins, δ-opioid receptor ligands, cholecystokinin A receptor ligands, ligands specific for angiotensin AT1 or AT2 receptors, peroxisome proliferator-activated receptor λ ligands, β-lactam antibiotics such as penicillin, small organic molecules including antimicrobial drugs, and other molecules that bind specifically to a receptor preferentially expressed on the surface of tumor cells or on an infectious organism, antimicrobial and other drugs designed to fit into the binding pocket of a particular receptor based on the crystal structure of the receptor or other cell surface protein, ligands of tumor antigens or other molecules preferentially expressed on the surface of tumor cells, or fragments of any of these molecules. An example of a tumor-specific antigen that could function as a binding site for ligand-drug, or analog or derivative thereof, conjugates include extracellular epitopes of a member of the Ephrin family of proteins, such as EphA2. EphA2 expression is restricted to cell-cell junctions in normal cells, but EphA2 is distributed over the entire cell surface in metastatic tumor cells. Thus, EphA2 on metastatic cells would be accessible for binding to, for example, an Fab fragment of an antibody conjugated to a drug, or analog or derivative thereof, whereas the protein would not be accessible for binding to the Fab fragment on normal cells, resulting in a ligand-drug conjugate specific for metastatic cancer cells.

In one embodiment, the receptor binding moiety is a vitamin, or a vitamin receptor binding analog or derivative thereof, such as vitamins and analogs and derivatives thereof that are capable of binding vitamin receptors.

The vitamins that can be used in accordance with the methods and compounds described herein include carnitine, inositol, lipoic acid, pyridoxal, ascorbic acid, niacin, pantothenic acid, folic acid, riboflavin, thiamine, biotin, vitamin $B_{12}$, vitamins A, D, E and K, other related vitamin molecules, analogs and derivatives thereof, and combinations thereof. These vitamins, and their receptor-binding analogs and derivatives, constitute illustrative targeting entities that can be coupled with the drug compounds, or their analogs or derivatives, by the polyvalent linkers (L) described herein to make drug delivery conjugates.

In one illustrative aspect, the vitamin can be folic acid, a folic acid analog, or another folate receptor-binding molecule. Exemplary of analogs of folate that can be used include folinic acid, pteroylpolyglutamic acid, pteroic acid and other amino acid derivatives thereof, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroyl-glutamic acid (dichloromethotrexate). Other suitable ligands capable of binding to folate receptors to initiate receptor mediated endocytotic transport of the drug delivery conjugate include antibodies to the folate receptor. Accordingly, in one illustrative aspect, a vinca compound in complex with an antibody to a folate receptor can be used to trigger transmembrane transport of the complex.

Illustrative embodiments of vitamin analogs and/or derivatives also include analogs and derivatives of biotin such as biocytin, biotin sulfoxide, oxybiotin and other biotin receptor-binding compounds, and the like. It is appreciated that analogs and derivatives of the other vitamins described herein are also contemplated herein.

Any shape of the described conjugates is contemplated herein, and is determined by the manner in which the drugs, receptor-binding moiety, and various polyvalent linkers are connected. In one aspect, the overall three-dimensional shape of the conjugates described herein are linear. In another aspect, the overall three-dimensional shape of the conjugates described herein are "Y" or "T" shaped. In another aspect, the overall three-dimensional shape of the conjugates described herein are "X" shaped or cross-shaped. In another In one illustrative embodiment of the drug delivery conjugates described herein, the polyvalent linker includes at least one releasable linker $(l_r)$. In another illustrative embodiment of the drug delivery conjugates described herein, the polyvalent linker includes at least two releasable linkers $(l_r)_2$. In another illustrative aspect, the polyvalent linker (L) includes at least one releasable linkers $(l_r)$ that is not a disulfide releasable linker. In another illustrative aspect, the polyvalent linker (L) has at least two releasable linkers $(l_r)_2$ where one releasable linker is not a disulfide releasable linker. It is appreciated that when more than one releasable linker is included in the polyvalent linker, those releasable linkers may be adjacent. It is further appreciated that when two releasable linkers are adjacent in the polyvalent linker, the two releasable linkers may cooperate to cause release of the drug.

The term "releasable linker" as used herein, and also known as cleavable linker, refers to a linker that includes at least one bond that can be broken under physiological conditions (e.g., a pH-labile, acid-labile, oxidatively-labile, or enzyme-labile bond). It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH.

It is understood that a cleavable bond can connect two adjacent atoms within the releasable linker and/or connect other linkers or (B) and/or (D), as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an heteroatom linker, a spacer linker, another releasable linker, the drug, or analog or derivative thereof, or the vitamin, or analog or derivative thereof, following breakage of the bond, the releasable linker is separated from the other moiety.

The liability of the cleavable bond can be adjusted by, for example, substitutional changes at or near the cleavable bond, such as including alpha branching adjacent to a cleavable disulfide bond, increasing the hydrophobicity of substituents on silicon in a moiety having a silicon-oxygen bond that may be hydrolyzed, homologating alkoxy groups that form part of a ketal or acetal that may be hydrolyzed, and the like.

Illustrative mechanisms for cleavage of the bivalant linkers described herein include the following 1,4 and 1,6 fragmentation mechanisms

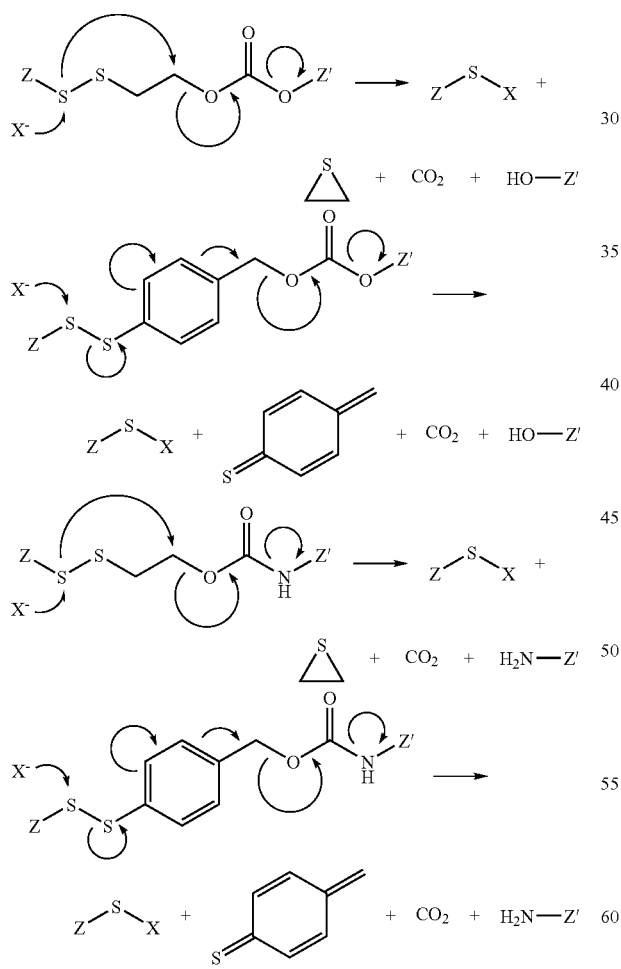

where X is an exogenous or endogenous nucleophile, glutathione, or bioreducing agent, and the like, and either of Z or Z' is the vitamin, or analog or derivative thereof, or the drug, or analog or derivative thereof, or a vitamin or drug moiety in conjunction with other portions of the polyvalent linker. It is to be understood that although the above fragmentation mechanisms are depicted as concerted mechanisms, any number of discrete steps may take place to effect the ultimate fragmentation of the polyvalent linker to the final products shown. For example, it is appreciated that the bond cleavage may also occur by acid-catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing polyvalent linkers, following an illustrative breaking of the disulfide bond, the resulting phenyl thiolate may further fragment to release a carbonic acid or carbamic acid moiety by forming a resonance stabilized intermediate. In any of these cases, the releasable nature of the illustrative polyvalent linkers described herein may be realized by whatever mechanism may be relevant to the chemical, metabolic, physiological, or biological conditions present.

Other illustrative mechanisms for bond cleavage of the releasable linker include oxonium-assisted cleavage as follows:

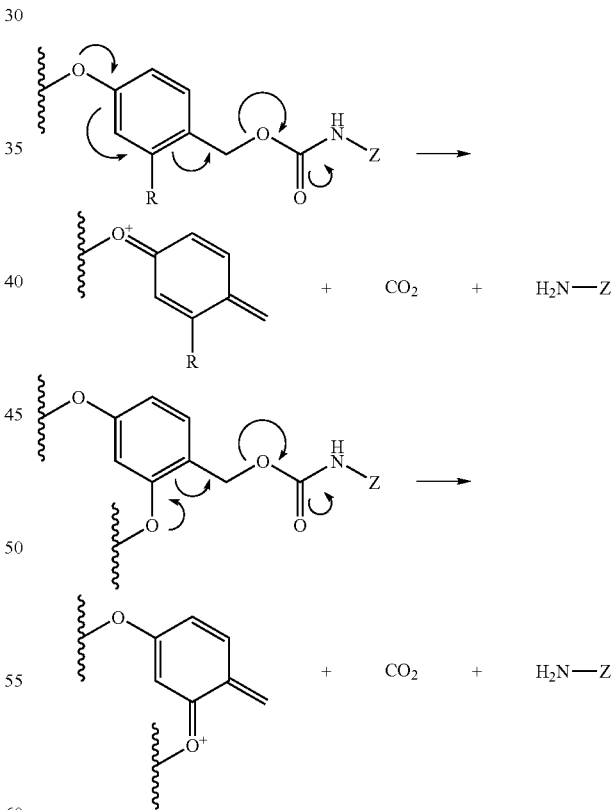

where Z is the vitamin, or analog or derivative thereof, or the drug, or analog or derivative thereof, or each is a vitamin or drug moiety in conjunction with other portions of the polyvalent linker, such as a drug or vitamin moiety including one or more spacer linkers, heteroatom linkers, and/or other releasable linkers. In this embodiment, acid-catalyzed elimination of the carbamate leads to the release of $CO_2$ and the nitrogen-containing moiety attached to Z, and the formation of a benzyl cation, which may be trapped by water, or any other Lewis base.

Another illustrative mechanism involves an arrangement of the releasable, spacer, and heteroatom linkers in such a way that subsequent to the cleavage of a bond in the polyvalent linker, released functional groups chemically assist the breakage or cleavage of additional bonds, also termed anchimeric assisted cleavage or breakage. An illustrative embodiment of such a polyvalent linker or portion thereof includes compounds having the formula:

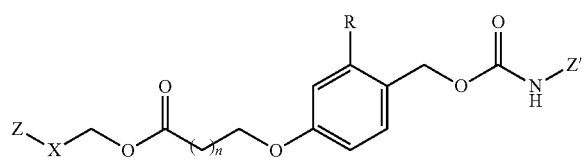

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and either of Z or Z' is the vitamin, or analog or derivative thereof, or the drug, or analog or derivative thereof, or a vitamin or drug moiety in conjunction with other portions of the polyvalent linker. It is appreciated that other substituents may be present on the aryl ring, the benzyl carbon, the carbamate nitrogen, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

In this embodiment, the hydroxyalkanoic acid, which may cyclize, facilitates cleavage of the methylene bridge, by for example an oxonium ion, and facilitates bond cleavage or subsequent fragmentation after bond cleavage of the releasable linker. Alternatively, acid catalyzed oxonium ion-assisted cleavage of the methylene bridge may begin a cascade of fragmentation of this illustrative polyvalent linker, or fragment thereof. Alternatively, acid-catalyzed hydrolysis of the carbamate may facilitate the beta elimination of the hydroxyalkanoic acid, which may cyclize, and facilitate cleavage of methylene bridge, by for example an oxonium ion. It is appreciated that other chemical mechanisms of bond breakage or cleavage under the metabolic, physiological, or cellular conditions described herein may initiate such a cascade of fragmentation. It is appreciated that other chemical mechanisms of bond breakage or cleavage under the metabolic, physiological, or cellular conditions described herein may initiate such a cascade of fragmentation.

In one embodiment, the polyvalent linkers described herein are compounds of the following formulae

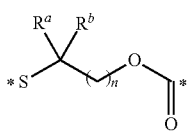 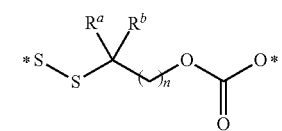

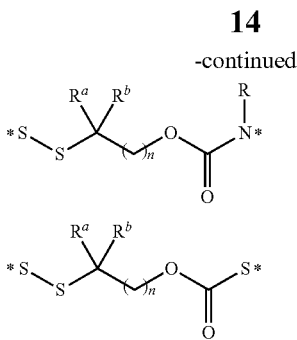

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the polyvalent linkers described herein include compounds of the following formulae

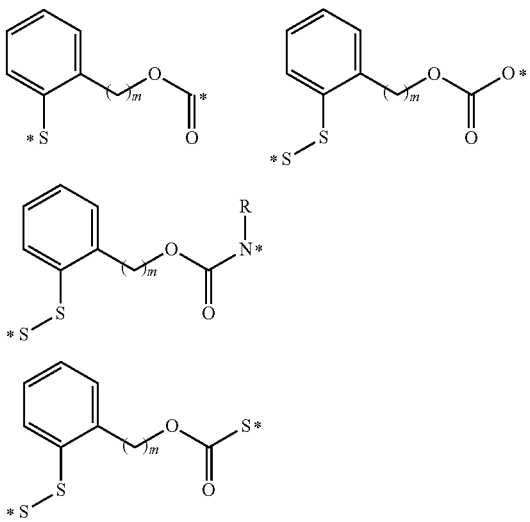

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the polyvalent linkers described herein include compounds of the following formulae

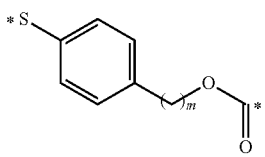

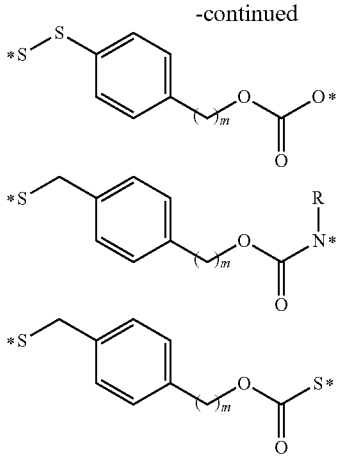

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the releasable, spacer, and heteroatom linkers may be arranged in such a way that subsequent to the cleavage of a bond in the polyvalent linker, released functional groups chemically assist the breakage or cleavage of additional bonds, also termed anchimeric assisted cleavage or breakage. An illustrative embodiment of such a polyvalent linker or portion thereof includes compounds having the formula:

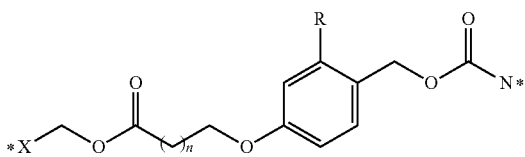

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and the symbol (*) indicates points of attachment for additional spacer, heteroatom, or releasable linkers forming the polyvalent linker, or alternatively for attachment of the drug, or analog or derivative thereof, or the vitamin, or analog or derivative thereof. It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

In another embodiment, the polyvalent linker includes heteroatom linkers, spacer linkers, and releasable linkers connected to form a polyvalent 3-thiosuccinimid-1-ylalkyloxymethyloxy group, illustrated by the following formula

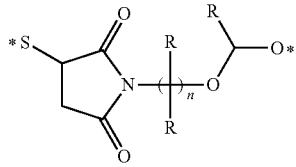

where n is an integer from 1 to 6, the alkyl group is optionally substituted, and the methyl is optionally substituted with an additional alkyl or optionally substituted aryl group, each of which is represented by an independently selected group R. The (*) symbols indicate points of attachment of the polyvalent linker fragment to other parts of the conjugates described herein.

In another embodiment, the polyvalent linker includes heteroatom linkers, spacer linkers, and releasable linkers connected to form a polyvalent 3-thiosuccinimid-1-ylalkylcarbonyl group, illustrated by the following formula

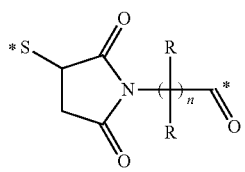

where n is an integer from 1 to 6, and the alkyl group is optionally substituted. The (*) symbols indicate points of attachment of the polyvalent linker fragment to other parts of the conjugates described herein. In another embodiment, the polyvalent linker includes heteroatom linkers, spacer linkers, and releasable linkers connected to form a polyvalent 3-thioalkylsulfonylalkyl(disubstituted silyl)oxy group, where the disubstituted silyl is substituted with alkyl and/or optionally substituted aryl groups.

In another embodiment, the polyvalent linker includes heteroatom linkers, spacer linkers, and releasable linkers connected to form a polyvalent dithioalkylcarbonylhydrazide group, or a polyvalent 3-thiosuccinimid-1-ylalkylcarbonylhydrazide, illustrated by the following formulae

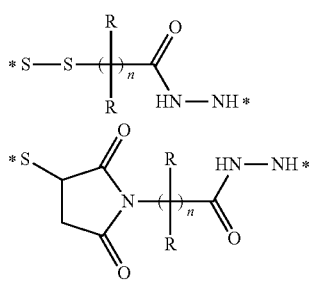

where n is an integer from 1 to 6, the alkyl group is optionally substituted, and the hydrazide forms an hydrazone with (13), (D), or another part of the polyvalent linker (L). The (*) symbols indicate points of attachment of the polyvalent linker fragment to other parts of the conjugates described herein.

In another embodiment, the polyvalent linker includes heteroatom linkers, spacer linkers, and releasable linkers connected to form a polyvalent 3-thiosuccinimid-1-ylalkyloxyalkyloxyalkylidene group, illustrated by the following formula

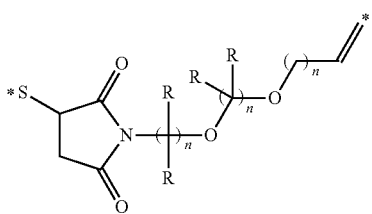

where each n is an independently selected integer from 1 to 6, each alkyl group independently selected and is optionally substituted, such as with alkyl or optionally substituted aryl, and where the alkylidene forms an hydrazone with (B), (D), or another part of the polyvalent linker (L). The (*) symbols indicate points of attachment of the polyvalent linker fragment to other parts of the conjugates described herein.

In another embodiment, the polyvalent linker includes heteroatom linkers, spacer linkers, and releasable linkers connected to form a polyvalent 3-thio or 3-dithioarylalkyloxycarbonyl group, 3-thio or 3-dithioarylalkylaminocarbonyl group, a polyvalent 3-thio or 3-dithioalkyloxycarbonyl, or a polyvalent 3-thio or 3-dithioalkylaminocarbonyl, where the alkyl carbonyl forms a carbonate, a carbamate, or urea with (B), (D), or another part of the polyvalent linker (L). Illustratively, the alkyl group is ethyl.

In another embodiment, the polyvalent linker includes heteroatom linkers, spacer linkers, and releasable linkers connected to form a polyvalent 3-dithioalkylamino group, where the amino forms a vinylogous amide with (B), (D), or another part of the polyvalent linker (L). Illustratively, the alkyl group is ethyl.

In another embodiment, the polyvalent linker includes heteroatom linkers, spacer linkers, and releasable linkers connected to form a polyvalent 1-alkoxycycloalkylenoxy group, a polyvalent alkyleneaminocarbonyl(dicarboxylarylene)carboxylate group, a polyvalent 3-dithioalkyloxycarbonyl group, a polyvalent 3-dithioalkyloxycarbonylhydrazide group, a polyvalent.

In another embodiment, the polyvalent linker includes at least one spacer linker that is a peptide formed from amino acids. In one aspect, the peptide includes naturally occurring amino acids, and stereoisomers thereof. In another aspect, the peptide is formed only from naturally occurring amino acids, and stereoisomers thereof.

Additional illustrative examples of spacer and releasable linkers are shown in Table 1 and 2, where the (*) indicates the point of attachment to another linker, to the vinca alkaloid, or analog or derivative thereof, or to the receptor binding moiety.

TABLE 1

Contemplated spacer and heteroatom linkers, and combinations thereof.

TABLE 1-continued
Contemplated spacer and heteroatom linkers, and combinations thereof.
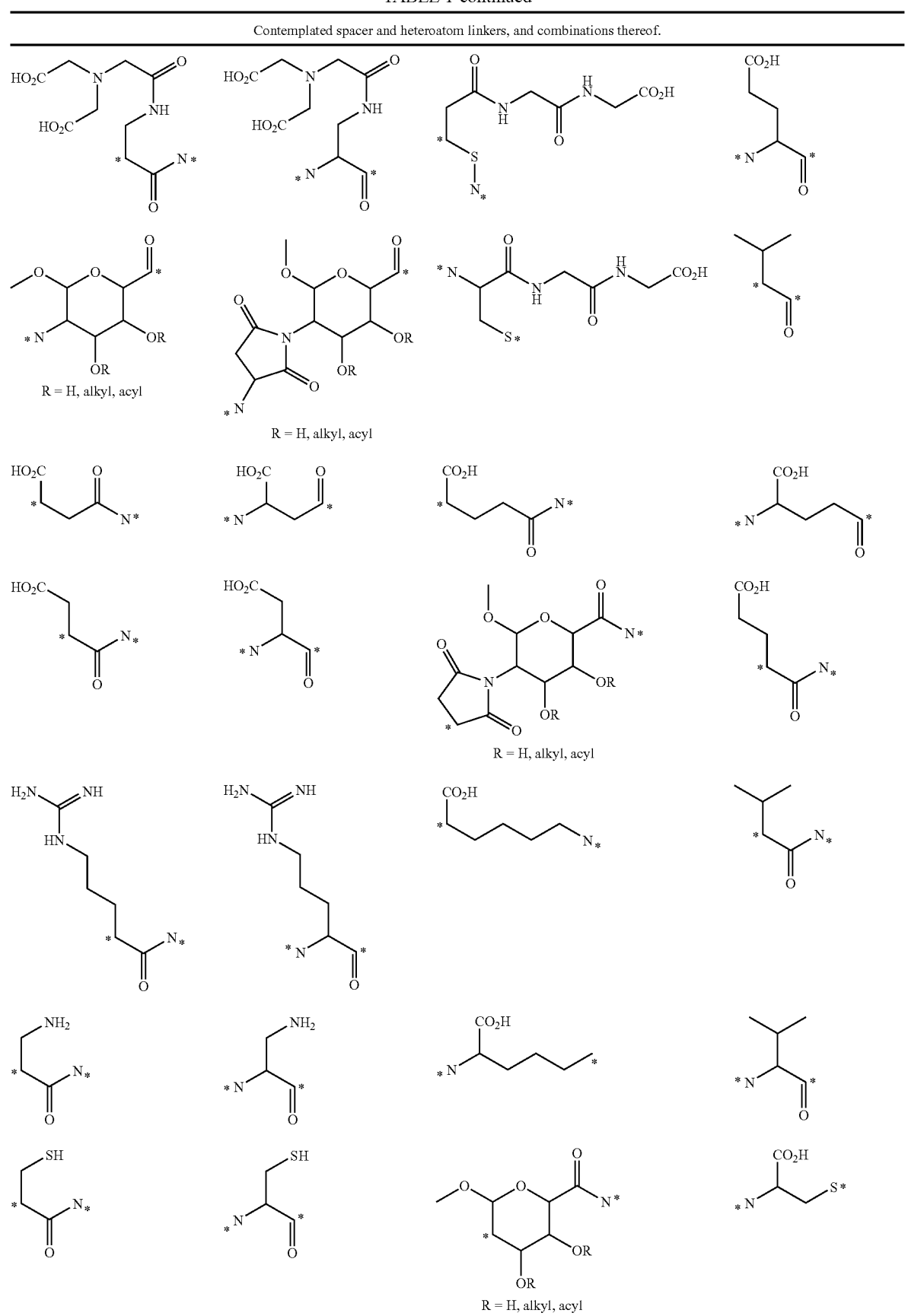

TABLE 1-continued
Contemplated spacer and heteroatom linkers, and combinations thereof.
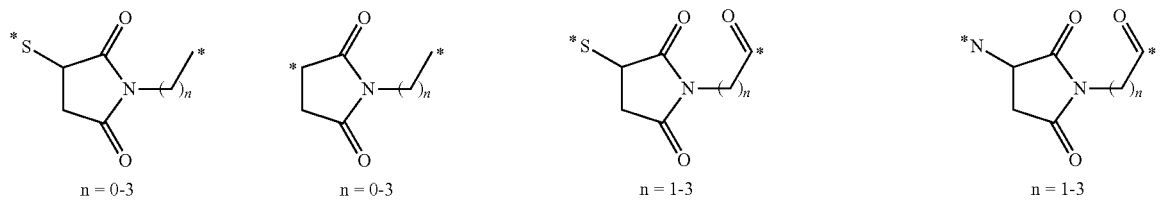
TABLE 2
Contemplated releasable and heteroatom linkers, and combinations thereof.
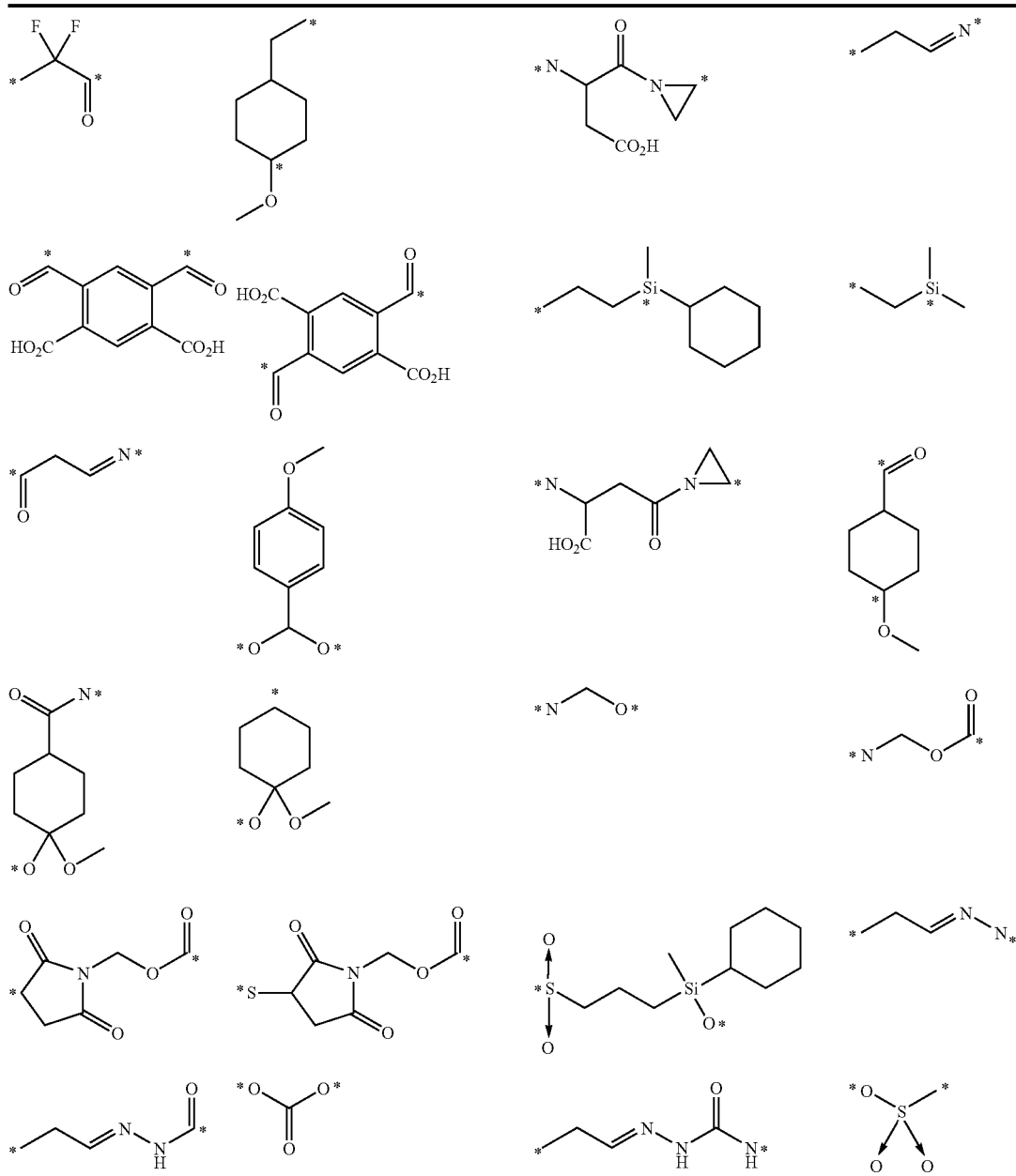

TABLE 2-continued

Contemplated releasable and heteroatom linkers, and combinations thereof.

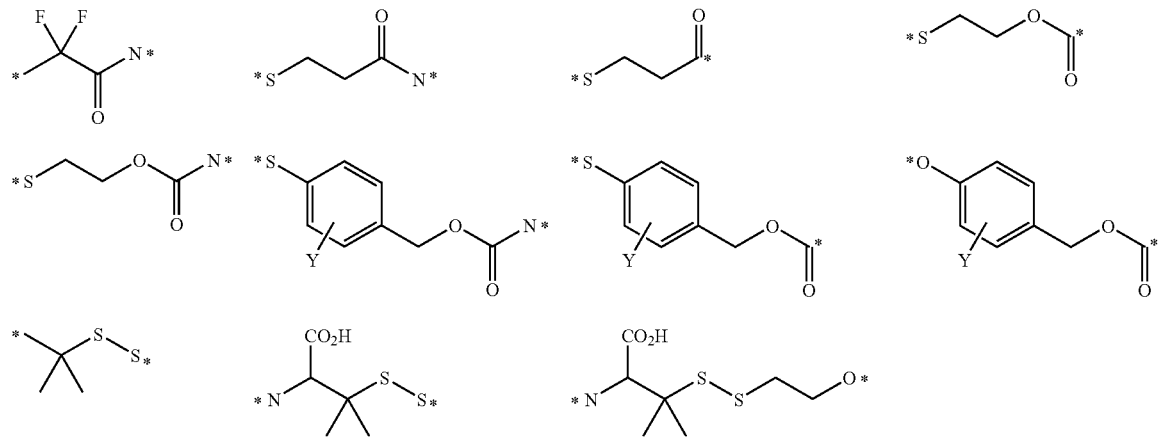

Any variety of drugs may be included in the drug delivery conjugates described herein. In one illustrative embodiment, the drugs are selected based on activity against one or more populations of pathogenic cells. In one aspect, those pathogenic cells are cancer cells, including solid tumors.

In another illustrative embodiment, the drugs are selected based on activity against one or more populations of pathogenic cells with a particular mechanism of action. Illustrative mechanisms of action include alkylating agents, microtubule inhibitors, including those that stabilize and/or destabilize microtubule formation, including beta-tubulin agents, cyclin dependent kinase (CDK) inhibitors, topoisomerase inhibitors, protein synthesis inhibitors, protein kinase inhibitors, including Ras, Raf, PKC, PI3K, and like inhibitors, transcription inhibitor, antifolates, heat shock protein blockers, and the like.

Illustrative alkylating agents include, but are not limited to, mitomycins CBI, and the like. Illustrative cyclin dependent kinase (CDK) inhibitors include, but are not limited to, CYC202, seliciclib, R-roscovitine, AGM-1470, and the like. Illustrative topoisomerase inhibitors include, but are not limited to, doxorubicin, other anthracyclines, and the like. Illustrative protein synthesis inhibitors include, but are not limited to, bruceantin, and the like. Illustrative protein kinase inhibitors, including Ras, Raf, PKC, PI3K, and like inhibitors, include but are not limited to L-779,450, R115777, and the like. Illustrative transcription inhibitors include, but are not limited to, α-amanatin, actinomycin, and the like. Illustrative antifolates include, but are not limited to, methotrexate, and the like. Illustrative heat shock protein blockers include, but are not limited to, geldanamycin, and the like.

Illustrative microtubule inhibitors, including those that stabilize and/or destabilize microtubule formation, including β-tubulin agents, microtubule poisons, and the like. Illustrative microtubule poisons that bind to selected receptors include, but are not limited to, inhibitors biding to the vinca binding site such as arenastatin, dolastatin, halichondrin B, maytansine, phomopsin A, rhizoxin, ustiloxin, vinblastine, vincristine, and the like, stabilizers binding to the taxol binding site such as discodermalide, epothilone, taxol, paclitaxol, and the like, inhibitors binding to the colchicine binding site such as, colchicine, combretastatin, curacin A, podophyllotoxin, steganacine, and the like, and others binding to undefined sites such as cryptophycin, tubulysins, and the like.

In one embodiment of the drug delivery conjugates described herein, at least one of the drugs is a microtubule inhibitor, or an analog or derivative thereof. In another embodiment, at least one of the drugs is a DNA alkylation agent. In another embodiment, at least one of the drugs is a DNA alkylation agent, and at least one other of the drugs is a microtubule inhibitor. alkaloids described herein include all members of the vinca indole-dihydroindole family of alkaloids, such as but not limited to vindesine, vinblastine, vincristine, catharanthine, vindoline, leurosine, vinorelbine, imidocarb, sibutramine, toltrazuril, vinblastinoic acid, and the like, and analogs and derivatives thereof.

In another embodiment of the drug delivery conjugates described herein, at least one of the drugs is a P-glycoprotein (PGP) inhibitor. In another embodiment, at least one of the drugs included on the drug delivery conjugates described herein is a PGP inhibitor, and at least one other of the drugs included on the drug delivery conjugates is a PGP substrate. Illustratively in this latter embodiment, the PGP substrate is a DNA alkylating agent. Referring to this embodiment, it is appreciated that pairing a PGP inhibitor with a PGP substrate, such as a DNA alkylating agent including, but not limited to, any of the mitomycins like mitomycin C, mitomycin A, and the like may improve the overall performance of the drug that is otherwise a PGP substrate. In the releasable conjugates described herein, the PGP inhibitor drug and the PGP substrate drug are both released in the cell after endocytosis. In that manner, the PGP inhibitor drug may improve the overall efficacy and/or potency of the PGP substrate drug. In addition, the PGP inhibitor may reduces PGP expression, which in turn will decrease efflux of one or more of the drugs included on the multidrug conjugates described herein from the pathogenic cell. It is appreciated that the mitomycins, or analogs or derivatives thereof, such as mitomycin C may operate as a PGP inhibitor, or down-regulator of PGP. It is further appreciated that the vinca alkaloid, or analog or derivative thereof, such as vinblastine analogs and derivatives, may be a PGP substrate that is protected from efflux from the pathogenic cell by the PGP inhibitor or down-regulator.

In another embodiment of the drug delivery conjugates described herein, at least one of the drugs is a vinca alkaloid, or an analog or derivative thereof. Vinca alkaloids described herein include all members of the vinca indole-dihydroindole family of alkaloids, such as but not limited to vindesine, vinblastine, vincristine, catharanthine, vindoline, leurosine, vinorelbine, imidocarb, sibutramine, toltrazuril, vinblastinoic acid, and the like, and analogs and derivatives thereof.

As referred to herein, the vinca drugs useable in the conjugates described herein include all members of the vinca indole-dihydroindole family of alkaloids, such as vindesine, vinblastine, vincristine, catharanthine, vindoline, leurosine, vinorelbine, imidocarb, sibutramine, toltrazuril, vinblastinoic acid, and the like, and analogs and derivatives thereof. Illustratively, such analogs and derivatives include the 3-carboxazides described in U.S. Pat. No. 4,203,898; the $N^2$-alkyl and other derivatives of 4-desacetylvinblastine-3-carboxhydrazide described in U.S. Pat. No. 4,166,810; leurosine hydrazide described in Neuss et al. Tetrahedron Lett. 783 (1968); the hydrazide derivatives described in Barnett et al. J. Med. Chem. 21:88 (1978); the C-4 ester derivatives described in U.S. Pat. Nos. 3,392,173 and 3,387,001; the dicarboxylic acid derivatives resulting from oxidation described in Langone et al. Anal. Biochem. 95:214 (1979); and the vinca hydrazides described in EP 0 247 792 A2. Each of the foregoing patents and publications is incorporated herein by reference for all that it discloses regarding synthetic routes, and reaction conditions for preparing vinca compounds.

In one illustrative embodiment, the vinca drugs are compounds of the formula

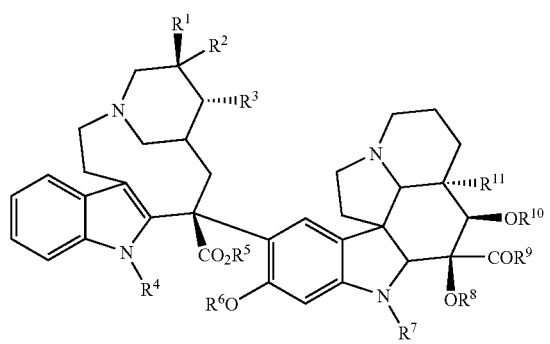

wherein:
one of $R^1$ and $R^2$ is H, and the other is ethyl, and $R^3$ is H, or $R^1$ is ethyl $R^2$, and $R^3$ are taken together to form —O—;
$R^4$, $R^7$, and $R^8$ are each independently selected from H, alkyl, and acyl
$R^5$ and $R^6$ are each independently selected alkyl;
$R^9$ is a group —NHNHR, where R is H, alkyl, or acyl;
$R^{10}$ is H or acyl; and
$R^{11}$ is ethyl.

In one aspect, the vinca drugs are compounds of the above formula wherein $R^4$ and $R^8$ are each H; and $R^5$, $R^6$, $R^9$, and $R^{10}$ are each methyl.

In another embodiment, a receptor binding drug delivery conjugate is described comprising a receptor binding moiety, a polyvalent linker (L), a vinca alkaloid drug, or analog or derivative thereof, and another drug, or analog or derivative thereof, wherein the receptor binding moiety, the vinca alkaloid, and the other drug are each bound to the polyvalent linker (L), through an heteroatom linker ($l_H$). The polyvalent linker (L) comprises one or more spacer linkers, heteroatom linkers, and releasable linkers, and combinations thereof, in any order.

In another embodiment, at least one of the drugs included on the drug delivery conjugates described herein is an aclamycin, or an analog or derivative thereof. It may be that the aclamycins and analogs and derivatives thereof are PGP efflux pump substrates. In one aspect, at least one other of the drugs included on the drug delivery conjugates described herein is an DNA alkylating agent, such as a mitomycin or an analog or derivative thereof.

In another embodiment, at least one of the drugs included on the drug delivery conjugates described herein is a DNA synthesis inhibitor, or an analog or derivative thereof. In another embodiment, at least one of the drugs included on the drug delivery conjugates described herein is a spindle formation inhibitor, or an analog or derivative thereof. In one aspect, at least one of the drugs included on the drug delivery conjugates described herein is a DNA synthesis inhibitor, or an analog or derivative thereof, and at least one other of the drugs included on the drug delivery conjugates described herein is a spindle formation inhibitor, or an analog or derivative thereof.

In another embodiment, at least one of the drugs included on the drug delivery conjugates described herein is a microtubule stabilizing agent, or an analog or derivative thereof. In another embodiment, at least one of the drugs included on the drug delivery conjugates described herein is a microtubule synthesis inhibitor, or an analog or derivative thereof. In another embodiment, at least one of the drugs included on the drug delivery conjugates described herein is a microtubule destabilizing agent, or an analog or derivative thereof.

In another embodiment, at least one of the drugs included on the drug delivery conjugates described herein is a apoptosis inducing agent, or an analog or derivative thereof. In another embodiment, at least one of the drugs included on the drug delivery conjugates described herein is a taxol, or an analog or derivative thereof. In another embodiment, at least one of the drugs included on the drug delivery conjugates described herein is an antifolate, or an analog or derivative thereof. In another embodiment, at least one of the drugs included on the drug delivery conjugates described herein is a methotrexate, or an analog or derivative thereof. In one aspect, at least one of the drugs included on the drug delivery conjugates described herein is an antifolate, or an analog or derivative thereof, such as methotrexate, and at least one other of the drugs included on the drug delivery conjugates described herein is a taxol, or an analog or derivative thereof.

In another embodiment, at least one of the drugs included on the drug delivery conjugates described herein is a folate, or an analog or derivative thereof. In another embodiment, at least one of the drugs included on the drug delivery conjugates described herein is a human epidermal growth factor receptor-2 (HER-2) inhibitor, or an analog or derivative thereof. In another embodiment, at least one of the drugs included on the drug delivery conjugates described herein is a radiolabeled chemotherapy agent, such as cisplatin, and the like. In one aspect, at least one of the drugs included on the drug delivery conjugates described herein is an antifolate, or an analog or derivative thereof, such as methotrexate, and at least one other of the drugs included on the drug delivery conjugates described herein is a folate, or an analog or derivative thereof. In another aspect, at least one of the drugs included on the drug delivery conjugates described herein is a taxol, or an analog or derivative thereof, and at least one other of the drugs included on the drug delivery conjugates described herein is a HER-2 inhibitor, or an analog or derivative thereof. In another aspect, at least one of the drugs included on the drug delivery conjugates described herein is a taxol, or an analog or derivative thereof, at least one other of the drugs included on the drug delivery conjugates described herein is a radiolabeled chemotherapy agent, such as cisplatin, and at least one other of the drugs included on the drug delivery conjugates described herein is a HER-2 inhibitor, or an analog or derivative thereof.

The drug delivery conjugates described herein can be prepared by conventional synthetic methods. The synthetic methods are chosen depending upon the selection of the heteroatom linkers, and the functional groups present on the spacer linkers and the releasable linkers. In general, the relevant bond forming reactions are described in Richard C. Larock, "Comprehensive Organic Transformations, a guide to functional group preparations," VCH Publishers, Inc. New York (1989), and in Theodora E. Greene & Peter G. M. Wuts, "Protective Groups ion Organic Synthesis," 2d edition, John Wiley & Sons, Inc. New York (1991), the disclosures of which in their entirety are incorporated herein by reference. Additional synthetic routes and reaction conditions are described in U.S. patent application publication no. US 2005/0002942 A1.

Illustratively, the drug delivery conjugates described herein may be prepared using both linear and convergent synthetic routes. Illustrative intermediates useable in such routes include intermediates comprising a polyvalent linker that includes a coupling group at each end suitable for covalent attachment to the receptor binding moiety, or analog or derivative thereof, and the vinca alkaloid, or analog or derivative thereof. Other illustrative intermediates useable in such routes include intermediates comprising a receptor binding moiety, or analog or derivative thereof, attached to a polyvalent linker, which includes a coupling group. Other illustrative intermediates useable in such routes include intermediates comprising a vinca alkaloid, or analog or derivative thereof, attached to a polyvalent linker, which includes a coupling group. In either case, the coupling group may be a nucleophile, an electrophile, or a precursor thereof.

In one illustrative embodiment synthetic intermediates, the coupling group is a Michael acceptor, and the polyvalent linker includes a releasable linker having the formula —C(O)NHN=, —NHC(O)NHN=, or —CH$_2$C(O)NHN=. In one illustrative aspect, the coupling group and the polyvalent linker are taken together to form a compound having the formula:

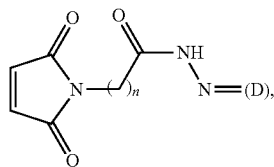

or a protected derivative thereof, where (D) is the vinca alkaloid, or an analog or a derivative thereof, capable of forming a hydrazone as illustrated herein; and n is an integer such as 1, 2, 3, or 4. In another illustrative aspect of the receptor binding drug delivery conjugate intermediate described herein, a second linker is covalently attached to the above formula through an alkylthiol nucleophile included on the second linker. In another illustrative aspect, the receptor binding moiety, or analog or derivative thereof, is covalently attached to the above formula through an alkylthiol nucleophile included on that moiety.

In another illustrative embodiment, the coupling group is a heteroatom, such as nitrogen, oxygen, or sulfur, and the polyvalent linker includes one or more heteroatom linkers and one or more spacer linkers covalently connecting the receptor binding moiety to the coupling group. In one illustrative aspect, the intermediate described herein includes a compound having the formula:

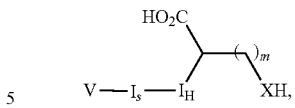

or a protected derivative thereof, where X is oxygen, nitrogen, or sulfur, and m is an integer such as 1, 2, or 3, and where (B), $1_s$, and $1_H$ are as defined herein. In one illustrative aspect, $1_H$ is —NH—, and m is 1. In another illustrative aspect, $1_H$ is —NH—, m is 1, and X is —S—.

In another illustrative embodiment, the intermediate described herein includes a compound having the formula:

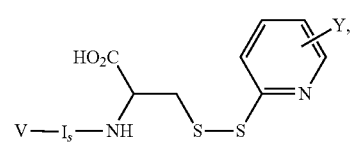

or a protected derivative thereof, where Y is H or a substituent, illustratively an electron withdrawing substituent, including but not limited to nitro, cyano, halo, alkylsulfonyl, a carboxylic acid derivative, and the like, and where (B) and $1_s$ are as defined herein.

In another illustrative embodiment of the intermediate described herein, the coupling group is a Michael acceptor, and the polyvalent linker includes one or more heteroatom linkers and one or more spacer linkers covalently connecting the receptor binding moiety to the coupling group. In one illustrative aspect, the coupling group and the polyvalent linker are taken together to form a compound having the formula:

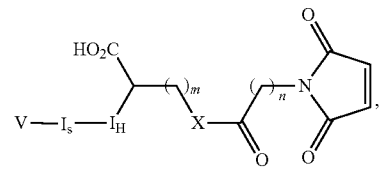

or a protected derivative thereof, where X is oxygen, nitrogen, or sulfur, and m and n are independently selected integers, such as 1, 2, or 3, and where (B), $1_s$, and $1_H$ are as defined herein. In another illustrative aspect, the vinca alkaloid, or analog or derivative thereof, is covalently attached to the above formula through an alkylthiol nucleophile included on the vinca alkaloid.

In another illustrative aspect, the intermediate includes compounds having the formulae:

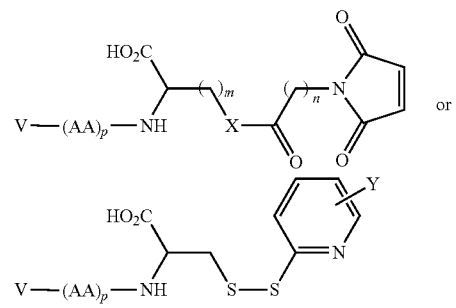

or protected derivatives thereof, where AA is one or more amino acids, illustratively selected from the naturally occurring amino acids, or stereoisomers thereof, X is nitrogen, oxygen, or sulfur, Y is hydrogen or a substituent, illustratively an electron withdrawing substituent, including but not limited to nitro, cyano, halo, alkylsulfonyl, a carboxylic acid derivative, and the like, n and m are independently selected integers, such as 1, 2, or 3, and p is an integer such as 1, 2, 3, 4, or 5.

AA can also be any other amino acid, such as any amino acid having the general formula:

where R is hydrogen, alkyl, acyl, or a suitable nitrogen protecting group, R' and R" are hydrogen or a substituent, each of which is independently selected in each occurrence, and t is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornithine, threonine, and the like. In another illustrative aspect of the vitamin receptor binding drug delivery conjugate intermediate described herein, the drug, or an analog or a derivative thereof, includes an alkylthiol nucleophile.

Each of the above intermediates may be prepared using conventional synthetic routes. Additional synthetic routes and reaction conditions are described in U.S. patent application publication no. US 2005/0002942 A1 and PCT international publication no. WO 2006/012527.

The foregoing illustrative embodiments are intended to be illustrative of the invention described herein, and should not be interpreted or construed as limiting in any way the invention as described herein. For example, compounds generally represented by the following illustrative vitamin-drug conjugate intermediate are to be included in the invention as described herein where $R^1$ and $R^2$ are each independently hydrogen or alkyl, such as methyl; and $l_H$ is a heteroatom, such as oxygen, sulfur, optionally substituted nitrogen, or optionally protected nitrogen, and the like. Two or more drugs, and optionally additional receptor-binding ligands, such as folates and analogs and derivatives thereof, may be covalently attached to this illustrative intermediate at ($l_H$), or at other functional groups present, such as the amide nitrogen or carbonyl, the acid carboxylate, or the guanidine amino group.

In another embodiment, a folate ligand intermediate is described having the following formula

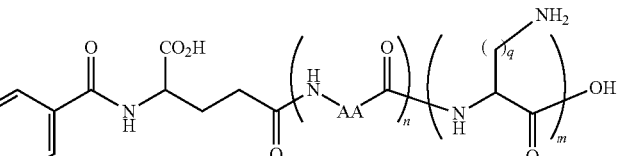
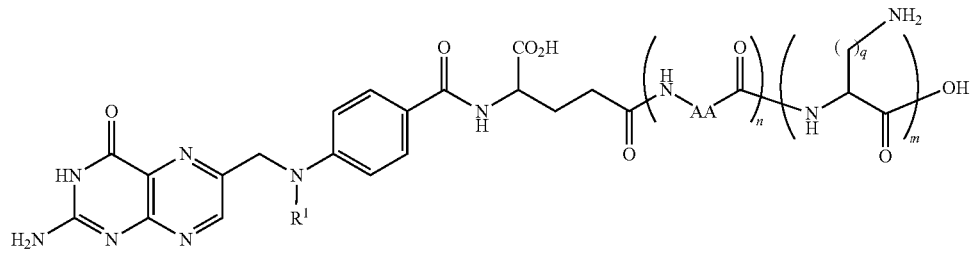

wherein m, n, and q are integers that are independently selected from the range of 0 to about 8; AA is an amino acid, $R^1$ is hydrogen, alkyl, or a nitrogen protecting group, and drugs are optionally attached at the (*) atoms. In one aspect, AA is a naturally occurring amino acid of either the natural or unnatural configuration. In another aspect, one or more of AA in the fragment (—NH-AA-C(O)—)$_n$ is a hydrophilic amino acid. In another aspect, one or more of AA in the fragment (—NH-AA-C(O)—)$_n$ is Asp and/or Arg. In another aspect, the integer o is 1 or greater. In another aspect, the integer m is 2 or greater. The drugs, or analogs or derivatives thereof, and optionally additional linkers and additional receptor-binding ligands may be connected to the above formula at the free NH side chains of the 2,ω-diaminoalkanoic acid fragments, or at the terminal carboxylate as indicated by the free valences therein.

In another embodiment, a folate ligand intermediate is described having the following formula

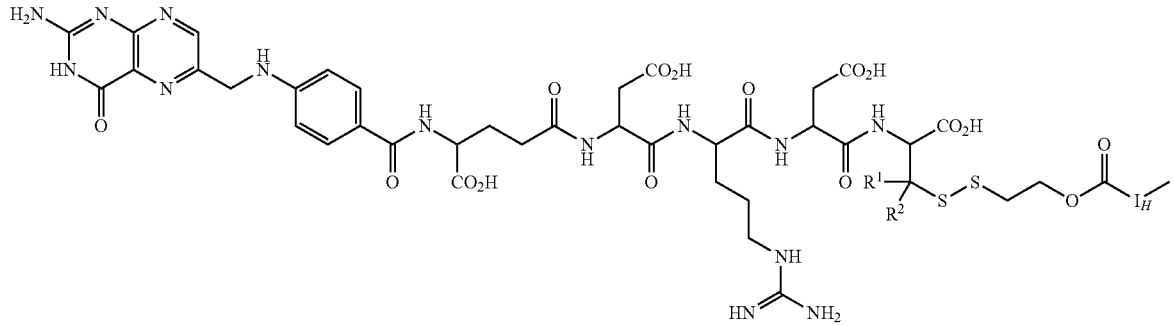

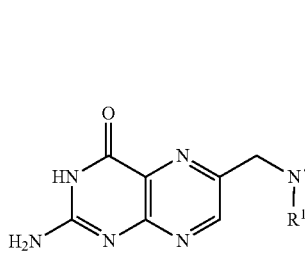

wherein m, n, q, and p are integers that are independently selected from the range of 0 to about 8; AA is an amino acid, $R^1$ is hydrogen, alkyl, or a nitrogen protecting group, and drugs are optionally attached at the (*) atoms. In one aspect, AA is as a naturally occurring amino acid of either the natural or unnatural configuration. In another aspect, one or more of AA in the fragment (—NH-AA-C(O)—)$_n$ is a hydrophilic amino acid. In another aspect, one or more of AA in the fragment (—NH-AA-C(O)—)$_n$ is Asp and/or Arg. In another aspect, the integers o and p are 1 or greater. In another aspect, the integer m is 2 or greater. The drugs, or analogs or derivatives thereof, and optionally additional linkers and additional receptor-binding ligands may be connected to the above formula at the free NH side chains of the 2,ω-diaminoalkanoic acid fragments, at the cyteinyl thiol groups, or at the terminal carboxylate, as indicated by the free valences therein.

In another embodiment, a folate ligand intermediate is described having the following formula

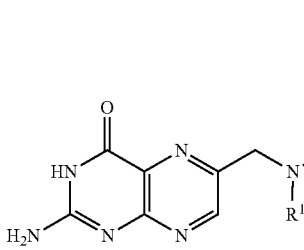

wherein m, n, q, p, and r are integers that are independently selected from the range of 0 to about 8; AA is an amino acid, $R^1$ is hydrogen, alkyl, or a nitrogen protecting group, and drugs are optionally attached at the (*) atoms. In one aspect, AA is as a naturally occurring amino acid of either the natural or unnatural configuration. In another aspect, one or more of AA in the fragment (—NH-AA-C(O)—)$_n$ is a hydrophilic amino acid. In another aspect, one or more of AA in the fragment (—NH-AA-C(O)—)$_n$ is Asp and/or Arg. In another aspect, the integers o, p, and r are 1 or greater. In another aspect, the integer m is 2 or greater. The drugs, or analogs or derivatives thereof, and optionally additional linkers and additional receptor-binding ligands may be connected to the above formula at the free NH side chains of the 2,ω-diaminoalkanoic acid fragments, at the cyteinyl thiol groups, at the serinyl hydroxy groups, or at the terminal carboxylate, as indicated by the free valences therein.

In another embodiment, a folate ligand intermediate that includes mitomycin as one of the drugs is described and having the following formula

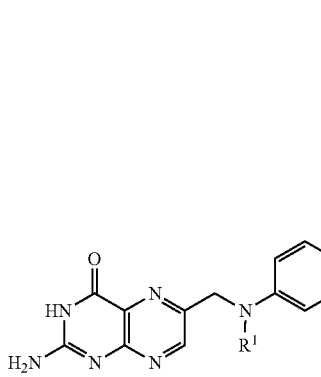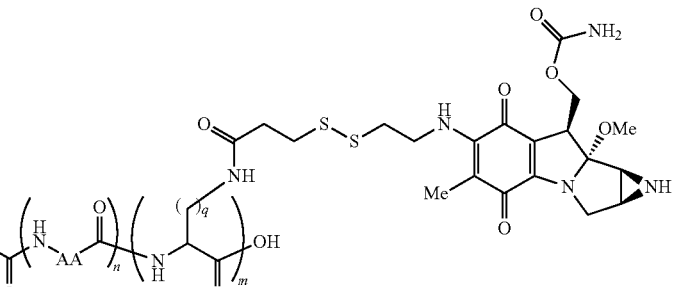

wherein m, n, and q are integers that are independently selected from the range of 0 to about 8; and AA is an amino acid. In one aspect, AA is as a naturally occurring amino acid of either the natural or unnatural configuration. In another aspect, one or more of AA in the fragment (—NH-AA-C(O)—)$_n$ is a hydrophilic amino acid. In another aspect, one or more of AA in the fragment (—NH-AA-C(O)—)$_n$ is Asp and/or Arg. In another aspect, the integer o is 1 or greater. In another aspect, the integer m is 2 or greater. The drugs, or analogs or derivatives thereof, and optionally additional linkers and additional receptor-binding ligands may be connected to the above formula at the additional free NH side chains of the 2,ω-diaminoalkanoic acid fragments, or at the terminal carboxylate, as indicated by the free valences therein.

In another embodiment, a folate ligand multidrug conjugate that includes a mitomycin and a vinca alkaloid is described and having the following formula

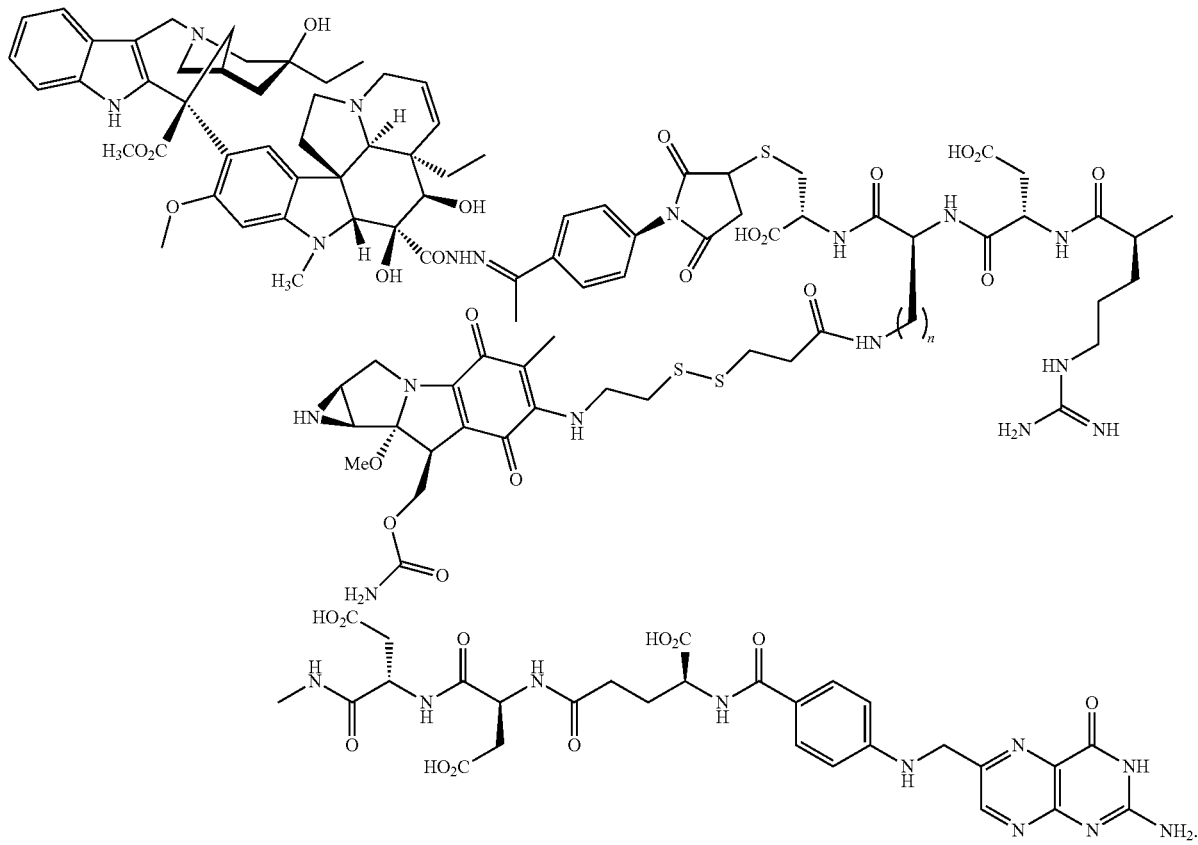

In another embodiment, a folate ligand multidrug conjugate that includes a mitomycin, an aclamycin, and a vinca alkaloid is described and having the following formula

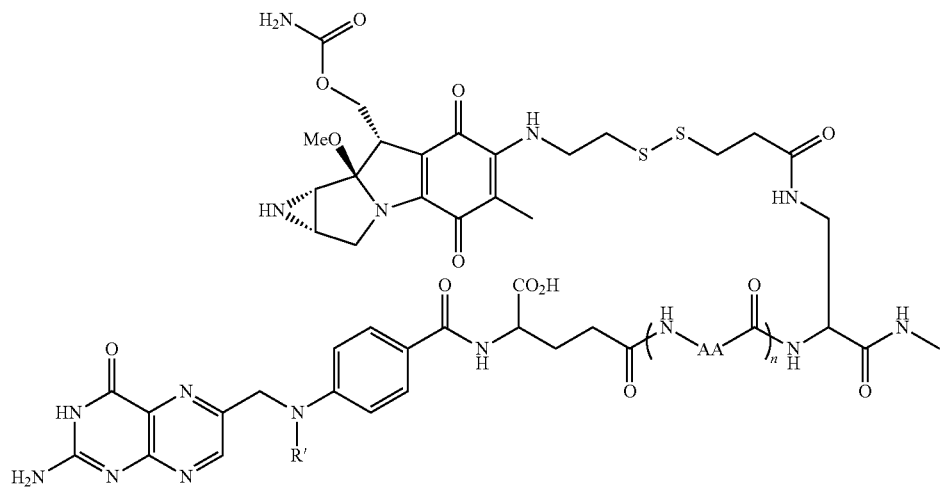

-continued

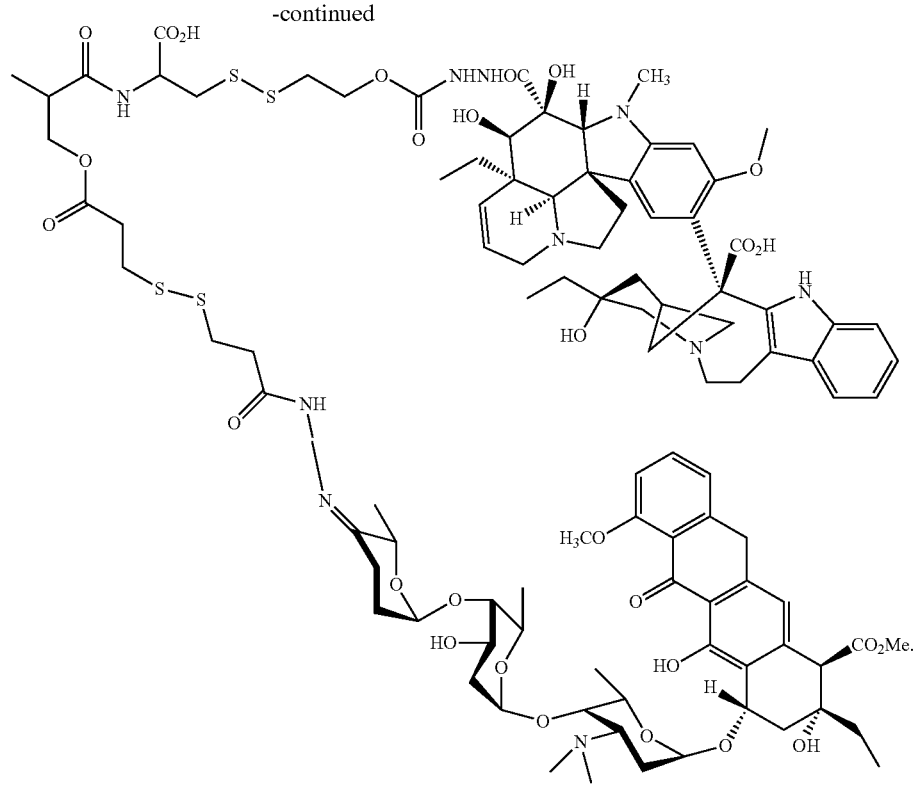

In another embodiment, a pharmaceutical composition is described. The pharmaceutical composition comprises a drug delivery conjugate described herein in combination with a pharmaceutically acceptable carrier, excipient, and/or diluent therefor.

In another embodiment, a method for eliminating a population of pathogenic cells in a host animal harboring the population of pathogenic cells is described. In one illustrative aspect, the members of the pathogenic cell population have an accessible binding site for a receptor binding moiety, or the analog or derivative thereof, and that binding site is uniquely expressed, overexpressed, or preferentially expressed by the pathogenic cells. The method includes the step of administering to the host a drug delivery conjugate described herein, or a pharmaceutical composition thereof, as described herein.

Populations of pathogenic cells that may be treated using the methods described herein include, but at not limited to cancers, such as epithelial cancers of the ovary, mammary gland, colon, lung, nose, throat, brain, and other tumor cell types, infectious agents, activated macrophages, activated monocytes, and the like.

The drug delivery conjugates described herein can be used for both human clinical medicine and veterinary applications. Thus, the host animal harboring the population of pathogenic cells and treated with the drug delivery conjugates can be human or, in the case of veterinary applications, can be a laboratory, agricultural, domestic, or wild animal. The drug delivery conjugates described herein can be administered to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The drug delivery conjugates described herein can be used to treat a variety of pathologies and pathogenic cells in host animals. As used herein, "pathogenic cells" means cancer cells, infectious agents such as bacteria and viruses, bacteria- or virus-infected cells, activated macrophages capable of causing a disease state, and any other type of pathogenic cells that uniquely express, preferentially express, or overexpress ligand receptors, such as vitamin receptors or receptors that bind analogs or derivatives of vitamins. Pathogenic cells can also include any cells causing a disease state for which treatment with the drug delivery conjugates results in reduction of the symptoms of the disease. The pathogenic cells can also be host cells that are pathogenic under some circumstances, such as cells of the immune system that are responsible for graft versus host disease, but not pathogenic under other circumstances.

Thus, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The invention can be utilized to treat such cancers as carcinomas, sarcomas, lymphomas, Hodgekin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

In embodiments where the pathogenic cell population is a cancer cell population, the effect of drug delivery conjugate administration is a therapeutic response measured by reduction or elimination of tumor mass or of inhibition of tumor cell proliferation. In the case of a tumor, the elimination can be an elimination of cells of the primary tumor or of cells that have metastasized or are in the process of dissociating from the primary tumor. A prophylactic treatment with the drug delivery conjugate to prevent return of a tumor after its removal by any therapeutic approach including surgical removal of the tumor, radiation therapy, chemotherapy, or biological therapy is also contemplated. The prophylactic treatment can be an initial treatment with the drug delivery conjugate, such as treatment in a multiple dose daily regimen, and/or can be an additional treatment or series of treatments after an interval of days or months following the initial treatment(s). Accordingly, elimination of any of the pathogenic cell populations described above includes reduction in the number of pathogenic cells, inhibition of proliferation of pathogenic cells, a prophylactic treatment that prevents return of pathogenic cells, or a treatment of pathogenic cells that results in reduction of the symptoms of disease.

In cases where cancer cells are being eliminated, the method described herein can be used in combination with surgical removal of a tumor, radiation therapy, chemotherapy, or biological therapies such as other immunotherapies including, but not limited to, monoclonal antibody therapy, treatment with immunomodulatory agents, adoptive transfer of immune effector cells, treatment with hematopoietic growth factors, cytokines and vaccination.

The method described herein is also applicable to populations of pathogenic cells that cause a variety of infectious diseases. For example, the present invention is applicable to such populations of pathogenic cells as bacteria, fingi, including yeasts, viruses, virus-infected cells, mycoplasma, and parasites. Infectious organisms that can be treated with the drug delivery conjugates described herein are any art-recognized infectious organisms that cause pathogenesis in an animal, including such organisms as bacteria that are gram-negative or gram-positive cocci or bacilli. For example, *Proteus* species, *Klebsiella* species, *Providencia* species, *Yersinia* species, *Erwinia* species, *Enterobacter* species, *Salmonella* species, *Serratia* species, *Aerobacter* species, *Escherichia* species, *Pseudomonas* species, *Shigella* species, *Vibrio* species, *Aeromonas* species, *Campylobacter* species, *Streptococcus* species, *Staphylococcus* species, *Lactobacillus* species, *Micrococcus* species, *Moraxella* species, *Bacillus* species, *Clostridium* species, *Corynebacterium* species, *Eberthella* species, *Micrococcus* species, *Mycobacterium* species, *Neisseria* species, *Haemophilus* species, *Bacteroides* species, *Listeria* species, *Erysipelothrix* species, *Acinetobacter* species, *Brucella* species, *Pasteurella* species, *Vibrio* species, *Flavobacterium* species, *Fusobacterium* species, *Streptobacillus* species, *Calymmatobacterium* species, *Legionella* species, *Treponema* species, *Borrelia* species, *Leptospira* species, *Actinomyces* species, *Nocardia* species, *Rickettsia* species, and any other bacterial species that causes disease in a host animal can be treated with the drug delivery conjugates described herein.

Of particular interest are bacteria that are resistant to antibiotics such as antibiotic-resistant *Streptococcus* species and *Staphylococcus* species, or bacteria that are susceptible to antibiotics, but cause recurrent infections treated with antibiotics so that resistant organisms eventually develop. Bacteria that are susceptible to antibiotics, but cause recurrent infections treated with antibiotics so that resistant organisms eventually develop, can be treated with the drug delivery conjugates described herein in the absence of antibiotics, or in combination with lower doses of antibiotics than would normally be administered to a host animal, to avoid the development of these antibiotic-resistant bacterial strains.

Diseases caused by viruses, such as DNA and RNA viruses, can also be treated with the drug delivery conjugates described herein. Such viruses include, but are not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picornaviruses, paramyxoviruses, reoviruses, retroviruses, lentiviruses, and rhabdoviruses.

The drug delivery conjugates described herein can also be used to treat diseases caused by any fungi, including yeasts, mycoplasma species, parasites, or other infectious organisms that cause disease in animals. Examples of fungi that can be treated with the method and drug delivery conjugates described herein include fungi that grow as molds or are yeastlike, including, for example, fungi that cause diseases such as ringworm, histoplasmosis, blastomycosis, aspergillosis, cryptococcosis, sporotrichosis, coccidioidomycosis, paracoccidio-idomycosis, muconnycosis, chromoblastomycosis, dermatophytosis, protothecosis, fusariosis, pityriasis, mycetoma, paracoccidioidomycosis, phaeohyphomycosis, pseudallescheriasis, sporotrichosis, trichosporosis, pneumocystis infection, and candidiasis.

The drug delivery conjugates described herein can also be used to treat parasitic infections including, but not limited to, infections caused by tapeworms, such as Taenia, Hymenolepsis, Diphyllobothrium, and *Echinococcus* species, flukes, such as Fasciolopsis, Heterophyes, Metagonimus, Clonorchis, Fasciola, Paragonimus, and *Schitosoma* species, roundworms, such as Enterobius, Trichuris, Ascaris, Ancylostoma, Necator, Strongyloides, Trichinella, Wuchereria, Brugia, Loa Onchocerca, and *Dracunculus* species, ameba, such as Naegleria and *Acanthamoeba* species, and protozoans, such as Plasmodium, Trypanosoma, Leislmuania, Toxoplasma, Entamoeba, Giardia, Isospora, Cryptosporidium, and *Enterocytozoon* species.

The pathogenic cells to which the drug delivery conjugates are directed can also be cells harboring endogenous pathogens, such as virus-, mycoplasma-, parasite- or bacteria-infected cells, if these cells preferentially express ligand receptors, such as receptors for vitamins, or analogs or derivatives thereof.

In one embodiment, the drug delivery conjugates can be internalized into the targeted pathogenic cells upon binding of the ligand to a receptor, transporter, or other surface-presented protein that specifically binds the ligand and which is preferentially expressed on the pathogenic cells. Such internalization can occur, for example, through receptor-mediated endocytosis. If the drug delivery conjugate contains a releasable linker, the ligand and the vinca compound can dissociate intracellularly and the vinca can act on its intracellular target.

In another illustrative embodiment, the ligand of the drug delivery conjugate can bind to the pathogenic cell placing the vinca compound in close association with the surface of the pathogenic cell. The vinca compound can then be released by cleavage of the releasable linker. For example, the vinca compound can be released by a protein disulfide isomerase if the releasable linker is a disulfide group. The vinca compound can then be taken up by the pathogenic cell to which the receptor binding drug delivery conjugate is bound, or the vinca compound can be taken up by another pathogenic cell in close proximity thereto. Alternatively, the vinca compound could be released by a protein disulfide isomerase inside the cell where the releasable linker is a disulfide group. The vinca compound may also be released by a hydrolytic mechanism, such as acid-catalyzed hydrolysis, as described above for certain beta elimination mechanisms, or by an anchimerically assisted cleavage through an oxonium ion or lactonium ion producing mechanism. The selection of the releasable linker or linkers will dictate the mechanism by which the vinca compound is released from the conjugate. It is appreciated that such a selection can be pre-defined by the conditions under which the drug delivery conjugate will be used.

In another illustrative embodiment, where the linker does not comprise a releasable linker, the ligand moiety of the drug delivery conjugate can bind to the pathogenic cell placing the vinca compound on the surface of the pathogenic cell to target the pathogenic cell for attack by other molecules capable of binding to the vinca compound. Alternatively, in this embodiment, the drug delivery conjugates can be internalized into the targeted cells upon binding, and the ligand moiety and the vinca compound can remain associated intracellularly with the vinca compound exhibiting its effects without dissociation from the ligand moiety.

In still another embodiment, or in combination with the above-described embodiments, where the drug delivery conjugate binds a vitamin receptor or another ligand receptor, the conjugate can bind to soluble vitamin receptors present in the serum or to serum proteins, such as albumin, resulting in prolonged circulation of the conjugates relative to the unconjugated vinca compound, and in increased activity of the conjugates towards the pathogenic cell population relative to the unconjugated vinca compound.

The binding site for the ligand, such as a vitamin, can include receptors for the ligand capable of specifically binding to the ligand wherein the receptor or other protein is uniquely expressed, overexpressed, or preferentially expressed by a population of pathogenic cells. A surface-presented protein uniquely expressed, overexpressed, or preferentially expressed by the pathogenic cells is typically a receptor that is either not present or present at lower concentrations on non-pathogenic cells providing a means for selective elimination of the pathogenic cells. The drug delivery conjugates may be capable of high affinity binding to receptors on cancer cells or other types of pathogenic cells. The high affinity binding can be inherent to the ligand or the binding affinity can be enhanced by the use of a chemically modified ligand.

The drug delivery conjugates described herein can be administered in a combination therapy with any other known drug whether or not the additional drug is targeted. Illustrative additional drugs include, but are not limited to, peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins, antigens and antibodies thereto, haptens and antibodies thereto, hormones, lipids, phospholipids, liposomes, toxins, antibiotics, analgesics, bronchodilators, beta-blockers, antimicrobial agents, antihypertensive agents, cardiovascular agents including antiarrhythmics, cardiac glycosides, antianginals, vasodilators, central nervous system agents including stimulants, psychotropics, antimanics, and depressants, antiviral agents, antihistamines, cancer drugs including chemotherapeutic agents, tranquilizers, anti-depressants, H-2 antagonists, anticonvulsants, antinauseants, prostaglandins and prostaglandin analogs, muscle relaxants, anti-inflammatory substances, stimulants, decongestants, antiemetics, diuretics, antispasmodics, antiasthmatics, anti-Parkinson agents, expectorants, cough suppressants, mucolytics, and mineral and nutritional additives.

In another illustrative aspect, the additional drug can be selected from a compound capable of stimulating an endogenous immune response. Suitable compounds include, but are not limited to, cytokines or immune cell growth factors such as interleukins 1-18, stem cell factor, basic FGF, EGF, G-CSF, GM-CSF, FLK-2 ligand, HILDA, MIP-1α, TGF-α, TGF-β, M-CSF, IFN-α, IFN-β, IFN-γ, soluble CD23, LIF, and combinations thereof.

Therapeutically effective combinations of these immunostimulatory factors can be used. In one embodiment, for example, therapeutically effective amounts of IL-2, for example, in amounts ranging from about 0.1 MIU/m$^2$/dose/day to about 15 MIU/m$^2$/dose/day in a multiple dose daily regimen, and IFN-α, for example, in amounts ranging from about 0.1 MIU/m$^2$/dose/day to about 7.5 MIU/m$^2$/dose/day in a multiple dose daily regimen, can be used along with the drug delivery conjugates to eliminate, reduce, or neutralize pathogenic cells in a host animal harboring the pathogenic cells (MIU=million international units; m$^2$=approximate body surface area of an average human). In another embodiment IL-12 and IFN-α can be used in the above-described therapeutically effective amounts for interleukins and interferons, and in yet another embodiment IL-15 and IFN-α can be used in the above described therapeutically effective amounts for interleukins and interferons. In an alternate embodiment IL-2, IFN-α or IFN-γ, and GM-CSF can be used in combination in the above described therapeutically effective amounts. Any other effective combination of cytokines including combinations of other interleukins and interferons and colony stimulating factors can also be used.

Further, the additional drug can be any drug known in the art which is cytotoxic or cytostatic, enhances tumor permeability, inhibits tumor cell proliferation, promotes apoptosis, decreases anti-apoptotic activity in target cells, is used to treat diseases caused by infectious agents, enhances an endogenous immune response directed to the pathogenic cells, or is useful for treating a disease state caused by any type of pathogenic cell. Exemplary suitable additional drugs include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, rhizoxin, T2 toxin, plant alkaloids, prednisone, hydroxyurea, teniposide, mitomycins, discodermolides, non-vinca microtubule inhibitors, epothilones, tubulysin, cyclopropyl benz[e]indolone, seco-cyclopropyl benz[e]indolone, O-Ac-seco-cyclopropyl benz[e]indolone, bleomycin and any other antibiotic, nitrogen mustards, nitrosureas, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, vindesine, vinblastine, vincristine, catharanthine, vindoline, leurosine, vinorelbine, imidocarb, sibutramine, toltrazuril, vinblastinoic acid, maytansines and analogs and derivatives thereof, gemcitabine, inflammatory and proinflammatory agents, peptide and peptidomimetic signal transduction inhibitors, and any other art-recognized drug or toxin. Other drugs that can be used in combination therapies include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other art-recognized antimicrobial compound. Analogs or derivatives of any of the above-described additional drugs can also be used in combination therapies.

In another illustrative embodiment, pharmaceutical compositions are provided. The pharmaceutical compositions comprise an amount of a drug delivery conjugate effective to eliminate a population of pathogenic cells in a host animal when administered in one or more doses. The drug delivery conjugate is preferably administered to the host animal parenterally, e.g., intradermally, subcutaneously, intramuscularly, intraperitoneally, intravenously, or intrathecally. Alternatively, the drug delivery conjugate can be administered to the host animal by other medically useful processes, such as orally, and any effective dose and suitable therapeutic dosage form, including prolonged release dosage forms, can be used. Exemplary excipients useful for oral dosage forms include, but are not limited to, corn starch, gelatin, lactose, magnesium stearate, sodium bicarbonate, cellulose derivatives, and sodium starch glycolate.

Examples of parenteral dosage forms include aqueous solutions of the active agent, in an isotonic saline, 5% glucose or other well-known pharmaceutically acceptable liquid carriers such as liquid alcohols, glycols, esters, and amides. The parenteral dosage form in accordance with this invention can be in the form of a reconstitutable lyophilizate comprising the dose of the drug delivery conjugate. In one aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference, or, alternatively, a slow pump (e.g., an osmotic pump) can be used.

The additional drug in the combination therapy can be administered to the host animal prior to, after, or at the same time as the drug delivery conjugates and the additional drug can be administered as part of the same composition containing the drug delivery conjugate or as part of a different composition than the drug delivery conjugate. Any such combination therapy at an effective dose of the additional drug can be used.

In another illustrative aspect, more than one type of drug delivery conjugate can be used. For example, the host animal can be treated in a co-dosing protocol with conjugates with different ligands such as, for example, folate-vinca and vitamin $B_{12}$-vinca conjugates in combination, and the like. In another illustrative embodiment, the host animal can be treated with conjugates comprising more than one ligand such as, for example, multiple folates or multiple vitamin $B_{12}$ molecules in one conjugate, or combinations of ligands in the same conjugate such as a vinca compound conjugated to both folate and vitamin $B_{12}$ ligands. Furthermore, drug delivery conjugates with different types of vinca compounds in separate drug delivery conjugates can be used.

The unitary daily dosage of the drug delivery conjugate can vary significantly depending on the host condition, the disease state being treated, the molecular weight of the conjugate, its route of administration and tissue distribution, and the possibility of co-usage of other therapeutic treatments such as radiation therapy or additional drugs in combination therapies. The effective amount to be administered to a host animal is based on body surface area, weight, and physician assessment of patient condition. Effective doses can range, for example, from about 1 ng/kg to about 1 mg/kg, from about 1 µg/kg to about 500 µg/kg, and from about 1 µg/kg to about 100 µg/kg.

Any effective regimen for administering the drug delivery conjugates can be used. For example, the drug delivery conjugates can be administered as single doses, or can be divided and administered as a multiple-dose daily regimen. Further, a staggered regimen, for example, one to three days per week can be used as an alternative to daily treatment, and for the purpose of defining this invention such intermittent or staggered daily regimen is considered to be equivalent to every day treatment and is comtemplated. In one illustrative embodiment the host animal is treated with multiple injections of the drug delivery conjugate to eliminate the population of pathogenic cells. In one embodiment, the host is injected multiple times (preferably about 2 up to about 50 times) with the drug delivery conjugate, for example, at 12-72 hour intervals or at 48-72 hour intervals. Additional injections of the drug delivery conjugate can be administered to the host animal at an interval of days or months after the initial injections(s) and the additional injections can prevent recurrence of the disease state caused by the pathogenic cells.

In one illustrative aspect, vitamins, or analogs or derivatives thereof, that can be used in the drug delivery conjugates include those that bind to receptors expressed specifically on activated macrophages, such as the folate receptor which binds folate, or an analog or derivative thereof. The folate-linked conjugates, for example, can be used to kill or suppress the activity of activated macrophages that cause disease states in the host. Such macrophage targeting conjugates, when administered to a host animal suffering from an activated macrophage-mediated disease state, work to concentrate and associate the conjugated vinca compounds in the population of activated macrophages to kill the activated macrophages or suppress macrophage function. Elimination, reduction, or deactivation of the activated macrophage population works to stop or reduce the activated macrophage-mediated pathogenesis characteristic of the disease state being treated. Exemplary of diseases known to be mediated by activated macrophages include rheumatoid arthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD) and chronic inflammations. Administration of the drug delivery conjugate is typically continued until symptoms of the disease state are reduced or eliminated.

The drug delivery conjugates administered to kill activated macrophages or suppress the function of activated macrophages can be administered parenterally to the host animal, for example, intradermally, subcutaneously, intramuscularly, intraperitoneally, or intravenously in combination with a pharmaceutically acceptable carrier. Alternatively, the drug delivery conjugates can be administered to the host animal by other medically useful procedures and effective doses can be administered in standard or prolonged release dosage forms. The therapeutic method can be used alone or in combination with other therapeutic methods recognized for treatment of disease states mediated by activated macrophages.

The following illustrative exemplified embodiments are not intended and should not be construed as limiting. For example, in each compound presented herein, the stereochemistry of amino acids used in forming the linker may b optionally selected from the natural L configuration, or the unnatural D configuration. Each Example was characterized by NMR, MS, and/or UV spectroscopy, and/or HPLC as indicated; selected characteristic signals are noted as appropriate.

METHOD EXAMPLES

Method Example 1

Inhibition of Tumor Growth in Mice

The anti-tumor activity of the compounds described herein, when administered intravenously (i.v.) to tumor-bearing animals, was evaluated in Balb/c mice bearing subcutaneous M109 tumors. Approximately 11 days post tumor inoculation in the subcutis of the right axilla with $1\times10^6$ M109 cells (average tumor volume at $t_o=60$ mm$^3$), mice (5/group) were injected i.v. three times a week (TIW), for 3 weeks with 1500 nmol/kg of the drug delivery conjugate or with an equivalent dose volume of PBS (control). Tumor growth was measured using calipers at 2-day or 3-day intervals in each treatment group. Tumor volumes were calculated using the equation $V=a\times b^2/2$, where "a" is the length of the tumor and "b" is the width expressed in millimeters.

Method Example 2

Inhibition of Tumor Growth in Mice

The anti-tumor activity of the compounds described herein, when administered intravenously (i.v.) to tumor-bearing animals, was evaluated in nu/nu mice bearing subcutaneous KB tumors. Approximately 8 days post tumor inoculation in the subcutis of the right axilla with $1\times10^6$ KB cells (average tumor volume at to =50-100 mm$^3$), mice (5/group) were injected i.v. three times a week (TIW), for 3 weeks with 5 µmol/kg of the drug delivery conjugate or with an equivalent dose volume of PBS (control). Tumor growth was measured using calipers at 2-day or 3-day intervals in each treatment group. Tumor volumes were calculated using the equation $V=a\times b^2/2$, where "a" is the length of the tumor and "b" is the width expressed in millimeters.

Method Example 3

Inhibition of Cellular DNA Synthesis

The compounds described herein were evaluated using an in vitro cytotoxicity assay that predicts the ability of the drug to inhibit the growth of folate receptor-positive KB cells. The compounds were comprised of folate linked to a respective chemotherapeutic drug, as prepared according to the protocols described herein. The KB cells were exposed for up to 7 h at 37° C. to the indicated concentrations of folate-drug conjugate in the absence or presence of at least a 100-fold excess of folic acid. The cells were then rinsed once with fresh culture medium and incubated in fresh culture medium for 72 hours at 37° C. Cell viability was assessed using a $^3$H-thymidine incorporation assay.

As shown in the figures herein, dose-dependent cytotoxicity was measurable, and in most cases, the $IC_{50}$ values (concentration of drug conjugate required to reduce $^3$H-thymidine incorporation into newly synthesized DNA by 50%) were in the low nanomolar range. Furthermore, the cytotoxicities of these conjugates were reduced in the presence of excess free folic acid, indicating that the observed cell killing was mediated by binding to the folate receptor.

Method Example 4

Relative Affinity Assay

The affinity for folate receptors (FRs) relative to folate was determined according to a previously described method (Westerhof, G. R., J. H. Schomagel, et al. (1995) Mol. Pharm. 48: 459-471) with slight modification. Briefly, FR-positive KB cells were heavily seeded into 24-well cell culture plates and allowed to adhere to the plastic for 18 h. Spent incubation media was replaced in designated wells with folate-free RPMI (FFRPMI) supplemented with 100 nM $^3$H-folic acid in the absence and presence of increasing concentrations of test article or folic acid. Cells were incubated for 60 min at 37° C. and then rinsed 3 times with PBS, pH 7.4. Five hundred microliters of 1% SDS in PBS, pH 7.4, were added per well. Cell lysates were then collected and added to individual vials containing 5 mL of scintillation cocktail, and then counted for radioactivity. Negative control tubes contained only the $^3$H-folic acid in FFRPMI (no competitor). Positive control tubes contained a final concentration of 1 mM folic acid, and CPMs measured in these samples (representing non-specific binding of label) were subtracted from all samples. Notably, relative affinities were defined as the inverse molar ratio of compound required to displace 50% of $^3$H-folic acid bound to the FR on KB cells, and the relative affinity of folic acid for the FR was set to 1.

Method Example 5

4T-1 tumor Volume Assay

Six to seven week-old mice (female Balb/c strain) were obtained from Harlan, Inc., Indianapolis, Ind. The mice were maintained on Harlan's folate-free chow for a total of three weeks prior to the onset of and during this experiment. Folate receptor-negative 4T-1 tumor cells ($1\times10^6$ cells per animal) were inoculated in the subcutis of the right axilla. Approximately 5 days post tumor inoculation when the 4T-1 tumor average volume was ~100 mm$^3$, mice (5/group) were injected i.v. three times a week (TIW), for 3 weeks with 3 µmol/kg of drug delivery conjugate or with an equivalent dose volume of PBS (control). Tumor growth was measured using calipers at 2-day or 3-day intervals in each treatment group. Tumor volumes were calculated using the equation $V=a\times b^2/2$, where "a" is the length of the tumor and "b" is the width expressed in millimeters.

Method Example 6

Weight Determination

The percentage weight change of the mice was determined in mice (5 mice/group) on the indicated days post-tumor inoculation (PTI) as shown in the graph for the samples described in the related tumor volume assay.

Method Example 7

General Preparation of Folate-Peptides

Linkers described herein that include a peptide are prepared by polymer-supported sequential approach using standard methods, such as the Fmoc-strategy on an acid-sensitive Fmoc-AA-Wang resin. Illustratively, the folate-containing peptidyl fragment Pte-Glu-(AA)$_n$-NH(CHR$_2$)CO$_2$H (3) is prepared by the method shown in Scheme 1 from Wang resin supported amino acids and Fmoc protected amino acid synthesis.

Scheme 1

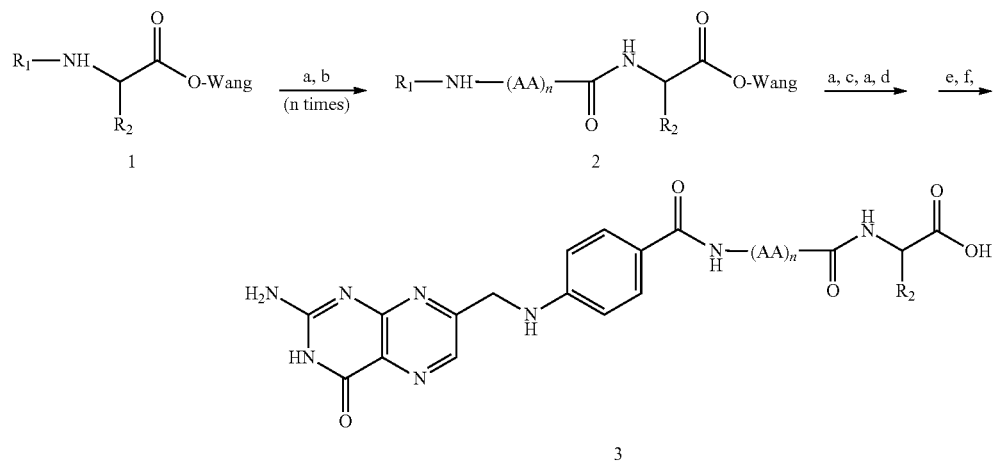

(a) 20% piperidine/DMP; (b) Fmoc-AA-OH, PyBop, DIPEA, DMF; (c) Fmoc-Glu-O-t-Bu or Fmoc-Glu(γ-O-t-Bu)-OH, PyBop, DIPEA, DMF; (d) $N^{10}$(TFA)-Pte-OH; PyBop, DIPEA, DMSO; (e) TFAA, $(CH_2SH)_2$, i-$Pr_3$SiH; (f) $NH_4OH$, pH 9-10.

In this illustrative embodiment of the processes described herein, $R_1$ is Fmoc, $R_2$ is the desired appropriately-protected amino acid side chain, Wang is a 2-chlorotrityl-Resin, and DIPEA is diisopropylethylamine. Standard coupling procedures, such as PyBOP and others described herein or known in the art are used, where the coupling agent is illustratively applied as the activating reagent to ensure efficient coupling. Fmoc protecting groups are removed after each coupling step under standard conditions, such as upon treatment with piperidine, tetrabutylammonium fluoride (TBAF), and the like. Appropriately protected amino acid building blocks, such as Fmoc-Glu-OtBu, $N^{10}$-TFA-Pte-OH, and the like, are used, as described in Scheme 1, and represented in step (b) by Fmoc-AA-OH. Thus, AA refers to any amino acid starting material, that is appropriately protected. It is to be understood that the term amino acid as used herein is intended to refer to any reagent having both an amine and a carboxylic acid functional group separated by one or more carbons, and includes the naturally occurring alpha and beta amino acids, as well as amino acid derivatives and analogs of these amino acids. In particular, amino acids having side chains that are protected, such as protected serine, threonine, cysteine, aspartate, and the like may also be used in the folate-peptide synthesis described herein. Further, gamma, delta, or longer homologous amino acids may also be included as starting materials in the folate-peptide synthesis described herein. Further, amino acid analogs having homologous side chains, or alternate branching structures, such as norleucine, isovaline, β-methyl threonine, β-methyl cysteine, β,β-dimethyl cysteine, and the like, may also be included as starting materials in the folate-peptide synthesis described herein.

The coupling sequence (steps (a) & (b)) involving Fmoc-protected amino acids (AA) of the formula Fmoc-AA-OH is performed "n" times to prepare solid-support peptide (2), where n is an integer and may equal 0 to about 100. Following the last coupling step, the remaining Fmoc group is removed (step (a)), and the peptide is sequentially coupled to a glutamate derivative (step (c)), deprotected, and coupled to TFA-protected pteroic acid (step (d)). Subsequently, the peptide is cleaved from the polymeric support upon treatment with trifluoroacetic acid, ethanedithiol, and triisopropylsilane (step (e)). These reaction conditions result in the simultaneous removal of the t-Bu, t-Boc, and Trt protecting groups that may form part of the appropriately-protected amino acid side chain. The TFA protecting group is removed upon treatment with base (step (f)) to provide the folate-containing peptidyl fragment (3).

COMPOUND EXAMPLES

Example 1

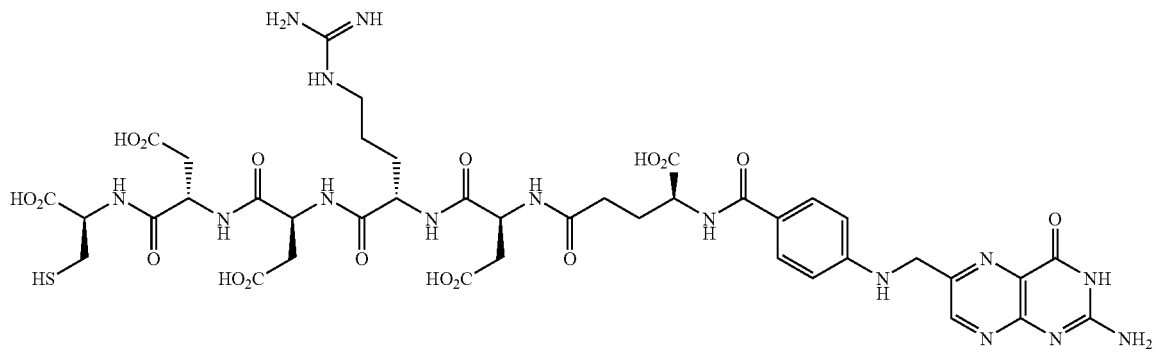 [SMILES: N=C(N)NCCC[C@H](NC(=O)[C@H](CC(=O)O)NC(=O)CC[C@H](NC(=O)c1ccc(NCc2cnc3nc(N)[nH]c(=O)c3n2)cc1)C(=O)O)C(=O)N[C@@H](CC(=O)O)C(=O)N[C@@H](CC(=O)O)C(=O)N[C@@H](CS)C(=O)O]

According to the general procedure of Method Example 7 (Scheme 1), Wang resin bound 4-methoxytrityl (MTT)-protected Cys-NH$_2$ was reacted according to the following sequence: 1) a. Fmoc-Asp(OtBu)-OH, PyBOP, DIPEA; b. 20% Piperidine/DMF; 2) a. Fmoc-Asp(OtBu)-OH, PyBOP, DIPEA; b. 20% Piperidine/DMF; 3) a. Fmoc-Arg(Pbf)-OH, PyBOP, DIPEA; b. 20% Piperidine/DMF; 4) a. Fmoc-Asp(OtBu)-OH, PyBOP, DIPEA; b. 20% Piperidine/DMF; 5) a. Fmoc-Glu-OtBu, PyBOP, DIPEA; b. 20% Piperidine/DMF; 6) N$^{10}$-TFA-pteroic acid, PyBOP, DIPEA. The MTT, tBu, and Pbf protecting groups were removed with TFA/H$_2$O/TIPS/EDT (92.5:2.5:2.5:2.5), and the TFA protecting group was removed with aqueous NH$_4$OH at pH=9.3. Selected $^1$H NMR (D$_2$O) δ (ppm) 8.68 (s, 1H, FA H-7), 7.57 (d, 2H, J=8.4 Hz, FA H-12 & 16), 6.67 (d, 2H, J=9 Hz, FA H-13 & 15), 4.40-4.75 (m, 5H), 4.35 (m, 2H), 4.16 (m, 1H), 3.02 (m, 2H), 2.55-2.95 (m, 8H), 2.42 (m, 2H), 2.00-2.30 (m, 2H), 1.55-1.90 (m, 2H), 1.48 (m, 2H); MS (ESI, m+H$^+$) 1046.

Example 2

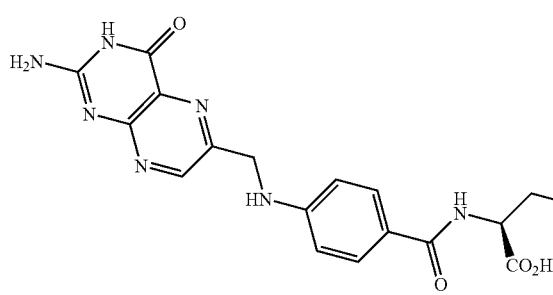
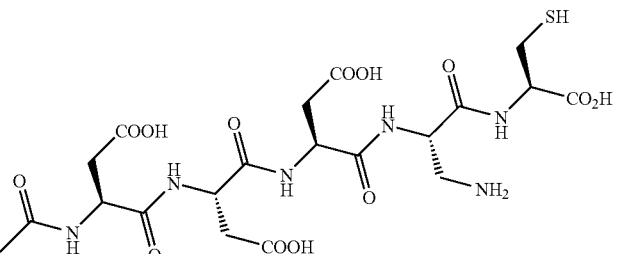

According to the general procedure of Method Example 7 (Scheme 1), Wang resin bound 4-methoxytrityl (MTT)-protected Cys-NH$_2$ was reacted according to the following sequence: 1) a. Fmoc-3-aminoalanine(NH-MTT)-OH, PyBOP, DIPEA; b. 20% Piperidine/DMF; 2) a. Fmoc-Asp(OtBu)-OH, PyBOP, DIPEA; b. 20% Piperidine/DMF; 3) a. Fmoc-Asp(OtBu)-OH, PyBOP, DIPEA; b. 20% Piperidine/DMF; 4) a. Fmoc-Asp(OtBu)-OH, PyBOP, DIPEA; b. 20% Piperidine/DMF; 5) a. Fmoc-Glu-OtBu, PyBOP, DIPEA; b. 20% Piperidine/DMF; 6) N$^{10}$-TFA-pteroic acid, PyBOP, DIPEA. The MTT, tBu, and TFA protecting groups were removed with a. 2% hydrazine/DMF; b. TFA/H$_2$O/TIPS/EDT (92.5:2.5:2.5:2.5).

The reagents shown in the following table were used in the preparation:

| Reagent | (mmol) | equivalents | Amount |
|---|---|---|---|
| H-Cys(4-methoxytrityl)-2-chlorotrityl-Resin (loading 0.56 mmol/g) | 0.56 | 1 | 1.0 g |
| Fmoc-β-aminoalanine(NH-MTT)-OH | 1.12 | 2 | 0.653 g |
| Fmoc-Asp(OtBu)-OH | 1.12 | 2 | 0.461 g |
| Fmoc-Asp(OtBu)-OH | 1.12 | 2 | 0.461 g |
| Fmoc-Asp(OtBu)-OH | 1.12 | 2 | 0.461 g |
| Fmoc-Glu-OtBu | 1.12 | 2 | 0.477 g |
| N$^{10}$TFA-Pteroic Acid (dissolve in 10 ml DMSO) | 0.70 | 1.25 | 0.286 g |
| DIPEA | 2.24 | 4 | 0.390 mL |
| PyBOP | 1.12 | 2 | 0.583 g |

The coupling step was performed as follows: In a peptide synthesis vessel add the resin, add the amino acid solution, DIPEA, and PyBOP. Bubble argon for 1 hr. and wash 3× with DMF and EPA. Use 20% piperidine in DMF for Fmoc deprotection, 3× (10 min), before each amino acid coupling. Continue to complete all 6 coupling steps. At the end wash the resin with 2% hydrazine in DMF 3× (5 min) to cleave TFA protecting group on Pteroic acid.

Cleave the peptide analog from the resin using the following reagent, 92.5% (50 ml) TFA, 2.5% (1.34 ml) H₂O, 2.5% (1.34 ml) Triisopropylsilane, 2.5% (1.34 ml) ethanedithiol, the cleavage step was performed as follows: Add 25 ml cleavage reagent and bubble for 1.5 hr, drain, and wash 3× with remaining reagent. Evaporate to about 5 mL and precipitate in ethyl ether. Centrifuge and dry. Purification was performed as follows: Column-Waters NovaPak C$_{18}$ 300×19 mm; Buffer A=10 mM Ammonium Acetate, pH 5; B=CAN; 1% B to 20% B in 40 minutes at 15 ml/min, to 350 mg (64%); HPLC-RT 10.307 min., 100% pure, $^1$H HMR spectrum consistent with the assigned structure, and MS (ES-): 1624.8, 1463.2, 1462.3, 977.1, 976.2, 975.1, 974.1, 486.8, 477.8.

Example 3

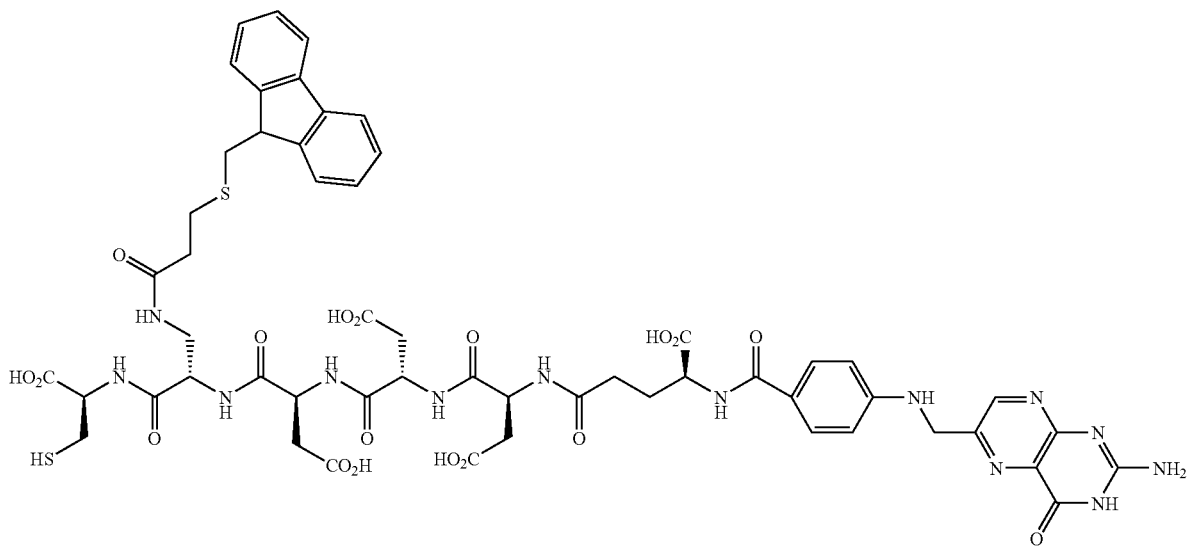 [SMILES: Nc1nc2ncc(CNc3ccc(C(=O)N[C@@H](CCC(=O)N[C@@H](CC(=O)O)C(=O)N[C@@H](CC(=O)O)C(=O)N[C@@H](CC(=O)O)C(=O)N[C@@H](CNC(=O)CCSCC4c5ccccc5-c5ccccc54)C(=O)N[C@@H](CS)C(=O)O)C(=O)O)cc3)nc2c(=O)[nH]1]

According to the general procedure of Method Example 7 (Scheme 1), Wang resin bound 4-methoxytrityl (MTT)-protected Cys-NH₂ was reacted according to the following sequence: 1) a. Fmoc-β-aminoalanine(NH-IvDde)-OH, PyBOP, DIPEA; b. 20% Piperidine/DMF; 2) a. Fmoc-Asp(OtBu)-OH, PyBOP, DIPEA; b. 20% Piperidine/DMF; 3) a. Fmoc-Asp(OtBu)-OH, PyBOP, DIPEA; b. 20% Piperidine/DMF; 4) a. Fmoc-Asp(OtBu)-OH, PyBOP, DIPEA; b. 20% Piperidine/DMF; 5) a. Fmoc-Glu-OtBu, PyBOP, DIPEA; b. 20% Piperidine/DMF; 6) N$^{10}$-TFA-pteroic acid, PyBOP, DIPEA. The MTT, tBu, and TFA protecting groups were removed with a. 2% hydrazine/DMF; b. TFA/H₂O/TIPS/EDT (92.5:2.5:2.5:2.5).

The reagents shown in the following table were used in the preparation:

| Reagent | (mmol) | Equivalents | Amount |
| --- | --- | --- | --- |
| H-Cys(4-methoxytrityl)-2-chlorotrityl-Resin (loading 0.56 mmol/g) | 0.56 | 1 | 1.0 g |
| Fmoc-β-aminoalanine(NH-IvDde)-OH | 1.12 | 2 | 0.596 g |
| Fmoc-Asp(OtBu)-OH | 1.12 | 2 | 0.461 g |
| Fmoc-Asp(OtBu)-OH | 1.12 | 2 | 0.461 g |
| Fmoc-Asp(OtBu)-OH | 1.12 | 2 | 0.461 g |
| Fmoc-Glu-OtBu | 1.12 | 2 | 0.477 g |
| N$^{10}$TFA-Pteroic Acid (dissolve in 10 ml DMSO) | 0.70 | 1.25 | 0.286 g |
| Fm-Thiopropionic acid | 0.70 | 1.25 | 199.08 |
| DIPEA | 2.24 | 4 | 0.390 mL |
| PyBOP | 1.12 | 2 | 0.583 g |

The coupling step was performed as follows: In a peptide synthesis vessel add the resin, add the amino acid solution in DMF, DIPEA, and PyBOP. Bubble argon for 1 hr. and wash 3×10 mL with DMF and IPA. Use 20% piperidine in DMF for Fmoc deprotection, 3×10 mL (10 min), before each amino acid coupling. Continue to complete 6 coupling steps. At the end wash the resin with 2% hydrazine in DMF 3×10 mL (5 min) to cleave TFA protecting group on Pteroic acid and IvDde protecting group on β-aminoalanine. Finally, couple the free amine of the β-aminoalanine with the Fmoc-thiopropionic acid in DMF using DIPEA and PyBop. Bubble argon for 1 hr. and wash 3×10 mL with DMF and IPA. Dry the resin under argon for 30 min.

Cleave the peptide analog from the resin using the following reagent, 92.5% (50 ml) TFA, 2.5% (1.34 ml) H₂O, 2.5% (1.34 ml) Triisopropylsilane, 2.5% (1.34 ml) ethanedithiol, the cleavage step was performed as follows: Add 25 ml cleavage reagent and bubble for 1.5 hr, drain, and wash 3× with remaining reagent. Evaporate to about 5 mL and precipitate in ethyl ether. Centrifuge and dry. Purification was performed as follows: Column-Waters NovaPak C$_{18}$ 300×19 mm; Buffer A=10 mM Ammonium Acetate, pH 5; B=CAN; 1% B to 20% B in 40 minutes at 15 ml/min, to 450 mg (65%); $^1$H HMR spectrum consistent with the assigned structure.

Example 4

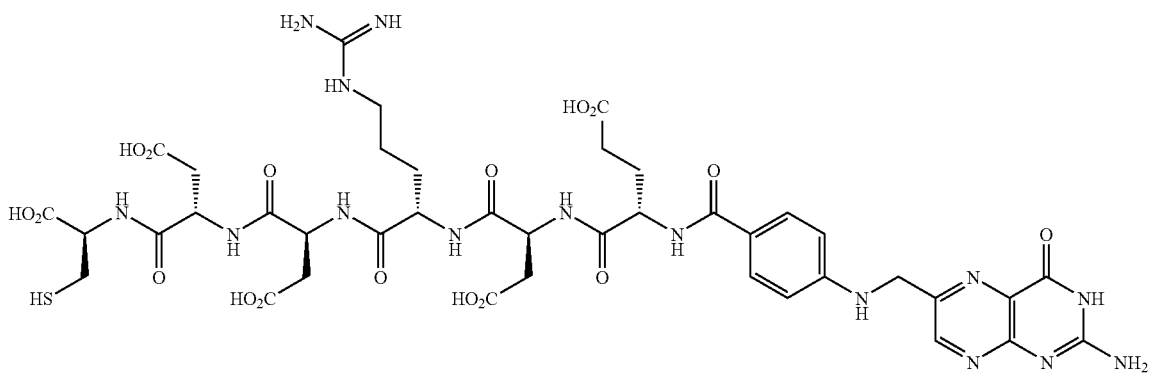 [SMILES: N=C(N)NCCC[C@H](NC(=O)[C@H](CC(=O)O)NC(=O)[C@H](CCC(=O)O)NC(=O)c1ccc(NCc2cnc3nc(N)[nH]c(=O)c3n2)cc1)C(=O)N[C@@H](CC(=O)O)C(=O)N[C@@H](CC(=O)O)C(=O)N[C@@H](CS)C(=O)O]

According to the general procedure of Method Example 7 (Scheme 1), Wang resin bound MTT-protected Cys-NH$_2$ was reacted according to the following sequence: 1) a. Fmoc-Asp(OtBu)-OH, PyBOP, DIPEA; b. 20% Piperidine/DMF; 2) a. Fmoc-Asp(OtBu)-OH, PyBOP, DIPEA; b. 20% Piperidine/DMF; 3) a. Fmoc-Arg(Pbf)-OH, PyBOP, DIPEA; b. 20% Piperidine/DMF; 4) a. Fmoc-Asp(OtBu)-OH, PyBOP, DIPEA; b. 20% Piperidine/DMF; 5) a. Fmoc-Glu(γ-OtBu)-OH, PyBOP, DIPEA; b. 20% Piperidine/DMF; 6) N$^{10}$-TFA-pteroic acid, PyBOP, DIPEA. The MTT, tBu, and Pbf protecting groups were removed with TFA/H$_2$O/TIPS/EDT (92.5:2.5:2.5:2.5), and the TFA protecting group was removed with aqueous NH$_4$OH at pH=9.3. The $^1$H NMR spectrum was consistent with the assigned structure.

Example 5

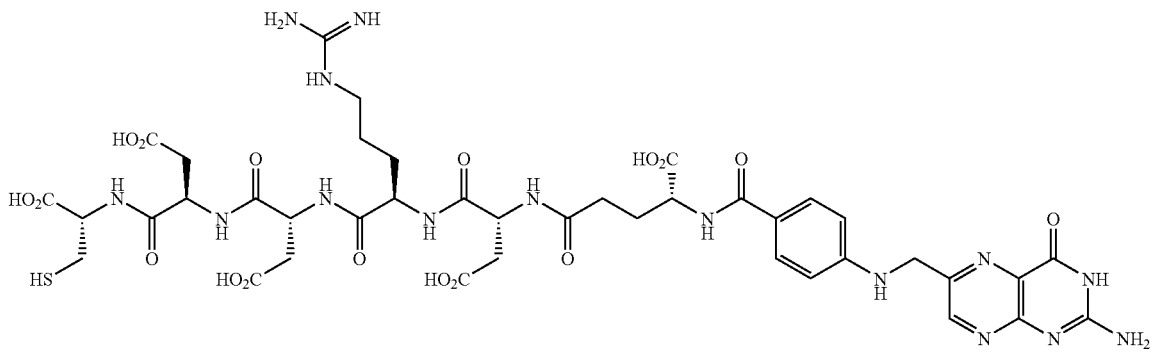 [SMILES: N=C(N)NCCC[C@@H](NC(=O)[C@@H](CC(=O)O)NC(=O)CC[C@@H](NC(=O)c1ccc(NCc2cnc3nc(N)[nH]c(=O)c3n2)cc1)C(=O)O)C(=O)N[C@H](CC(=O)O)C(=O)N[C@H](CC(=O)O)C(=O)N[C@H](CS)C(=O)O]

According to the general procedure of Method Example 7 (Scheme 1), Wang resin bound MTT-protected D-Cys-NH$_2$ was reacted according to the following sequence: 1) a. Fmoc-D-Asp(OtBu)-OH, PyBOP, DIPEA; b. 20% Piperidine/DMF; 2) a. Fmoc-D-Asp(OtBu)-OH, PyBOP, DIPEA; b. 20% Piperidine/DMF; 3) a. Fmoc-D-Arg(Pbf)-OH, PyBOP, DIPEA; b. 20% Piperidine/DMF; 4) a. Fmoc-D-Asp(OtBu)-OH, PyBOP, DIPEA; b. 20% Piperidine/DMF; 5) a. Fmoc-D-Glu-OtBu, PyBOP, DIPEA; b. 20% Piperidine/DMF; 6) N$^{10}$-TFA-pteroic acid, PyBOP, DIPEA. The MTT, tBu, and Pbf protecting groups were removed with TFA/H$_2$O/TIPS/EDT (92.5:2.5:2.5:2.5), and the TFA protecting group was removed with aqueous NH$_4$OH at pH=9.3. The $^1$H NMR spectrum was consistent with the assigned structure.

Example 6

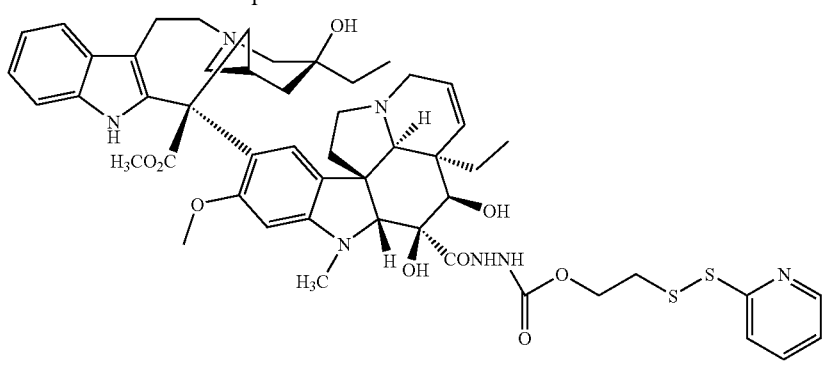

2-[(Benzotriazole-1-yl-(oxycarbonyloxy)-ethyldisulfanyl]-pyridine HCl (601 mg) and 378 μL of DIPEA were sequentially added to a solution of desacetyl vinblastine hydrazide (668 mg) in 5 ml of DCM at 0° C. The reaction was allowed to warm to room temperature and stirred for 3 hours. TLC (15% MeOH in DCM) showed complete conversion. The mixture was purified by silica gel chromatography (1:9 MeOH/DCM). The combined fractions were evaporated, redissolved in DCM and washed with 10% $Na_2CO_3$, brine, dried ($MgSO_4$), and evaporated to 550 mg (80%); HPLC-RT 12.651 min., 91% pure, $^1$H HMR spectrum consistent with the assigned structure, and MS (ESI+): 984.3, 983.3, 982.4, 492.4, 491.9, 141.8. Additional details of this procedure are described in U.S. patent application publication no. US 2005/0002942 A1, incorporated herein in its entirety by reference.

Example 7

Mitomycin C-Ethyl Disulfide Propionic Acid was Prepared According to the Following Scheme

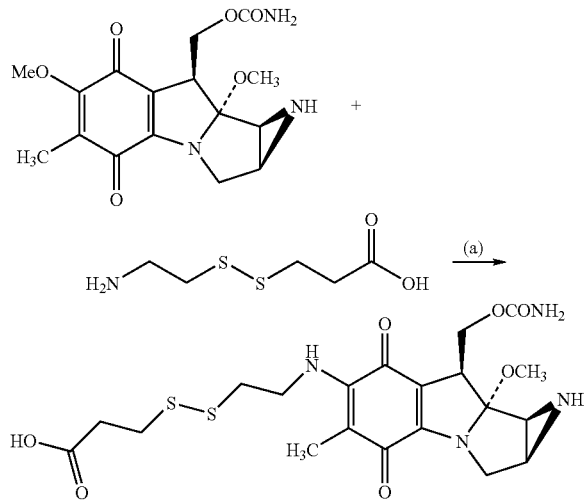

(a) diisopropylethylamine (DIPEA), MeOH.

To a solution of the aminoethyldisulfide propionic acid (81 mg, 0.372 mmol) in 2 mL of methanol (MeOH) was added the DIPEA (0.13 mL, 0.746 mmol). To this solution was slowly added the mitomycin-A (100 mg, 0.286 mmol) in MeOH (3.0 mL). The resulting solution was allowed to stir for 3 h. TLC analysis (20% MeOH in $CHCl_3$) indicated that the reaction was complete. The solvent was removed under reduced pressure and the residue was purified using a silica column. Gradient elution (10% to 20% MeOH in $CHCl_3$/0.5% TEA gave pure fractions of the product (110 mg, 77%). Selected $^1$H NMR signals ($CDCl_3$) δ (ppm) 3.50 (d, 1H), 3.56 (dd, 1H), 3.90 (t, 2H), 4.15 (d, 1H), 4.25 (t, 1H), 4.68 (dd, 1H).

Example 8

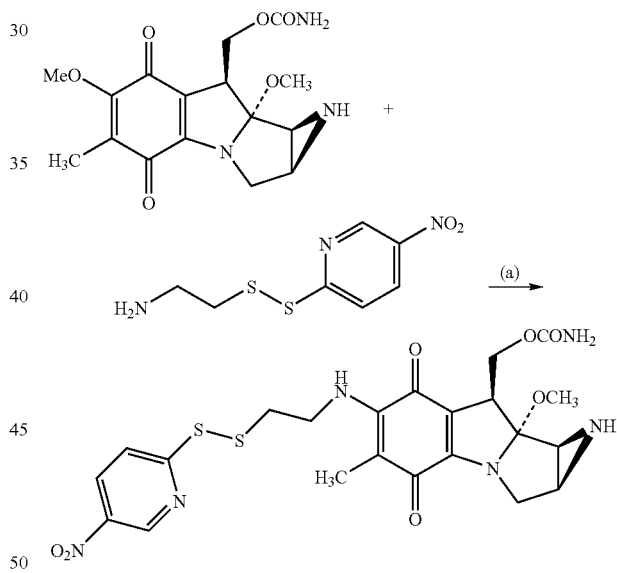

Prepared according to the process of Example 7.

Example 9

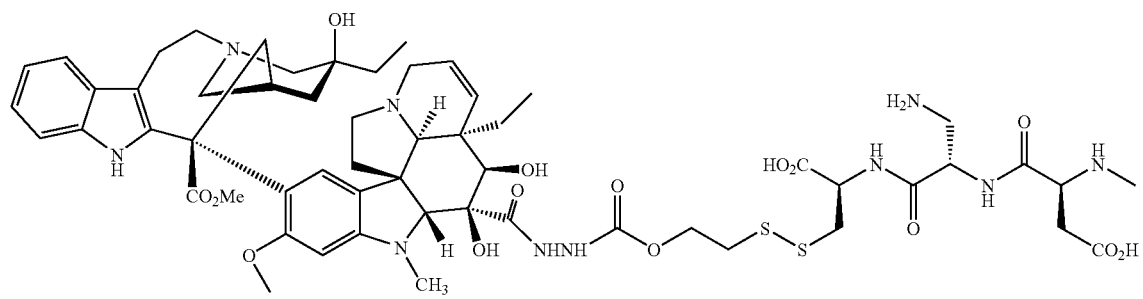

-continued

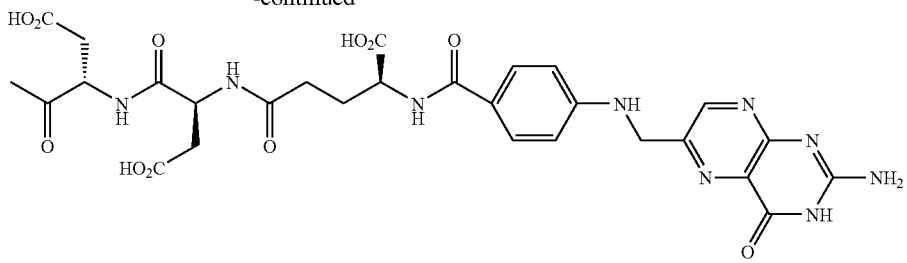

In a polypropylene centrifuge bottle, Example 2 (82 mg, 0.084 mmol) was dissolved in 5 mL of water and bubbled with argon for 10 min. In another flask, a 0.1N NaHCO$_3$ solution was argon bubbled for 10 min. pH of the linker solution was adjusted to about 6.9 using the 0.1N NaHCO$_3$ solution. The vinblastine hydrazide derivative (Example 6, 91 mg, 0.092 mM) in 5 mL of tetrahydrofuran (THF) was added slowly to the above solution. The resulting clear solution was stirred under argon for 15 min to 1 h. Progress of the reaction was monitored by analytical HPLC (10 mM ammonium acetate, pH=7.0 and acetonitrile). THF was evaporated, and the aqueous solution was filtered and injected on a prep-HPLC column (XTerra Column, 19×300 mM). Elution with 1 nm sodium phosphate pH=7.0 and acetonitrile resulted in pure fractions containing the product, which was isolated after freeze-drying for 48 h (78 mg, 50%); C$_{83}$H$_{103}$N$_{19}$O$_{26}$S$_2$; exact mass: 1845.68; MW: 1846.95; HPLC-RT 15.113 min., 100% pure, $^1$H HMR spectrum consistent with the assigned structure, and MS (ES−): 1846.6, 1845.5, 933.3, 924.2, 923.3, 922.5, 615.6, 614.7, 525.0.

FIGS. 21A and 21B show the relative binding affinity for folate versus Example 9, and the effects of Example 9 on $^3$H-thymidine incorporation, the IC$_{50}$ of the conjugate (58 nM), and that folate competes with the conjugate for binding to the folate receptor demonstrating the specificity of binding of the conjugate. The assays were conducted according to Method Examples 4 and 3, respectively.

Figure 1B:
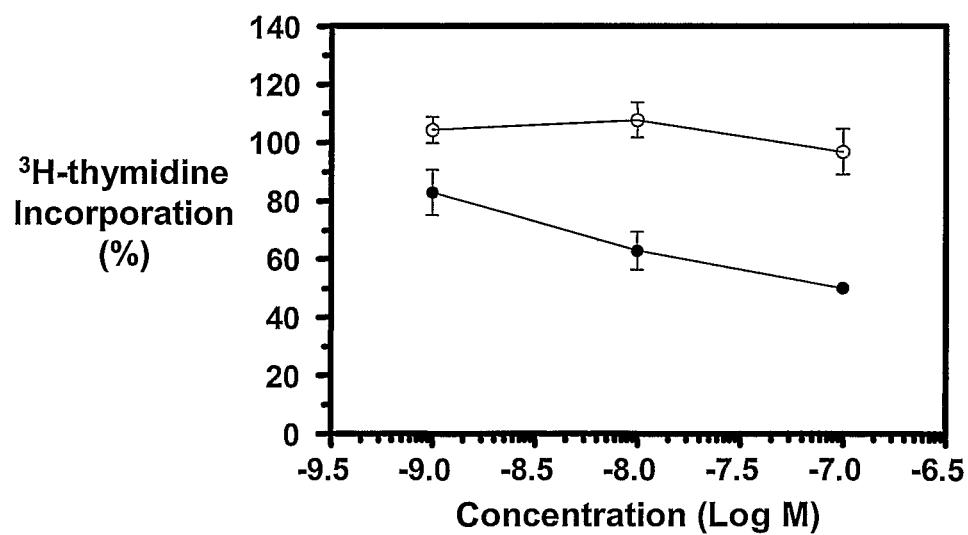
FIG. 1B shows the activity of Example 9 on $^3$H-thymidine incorporation in KB cells with (○) and without (●) excess folic acid; $IC_{50}$ of Example 9 is about 58 nM.

FIG. 1B shows the activity of Example 9 on $^3$H-thymidine incorporation in KB cells with (○) and without (●) excess folic acid; IC$_{50}$ of Example 9 is about 58 nM.

Example 10

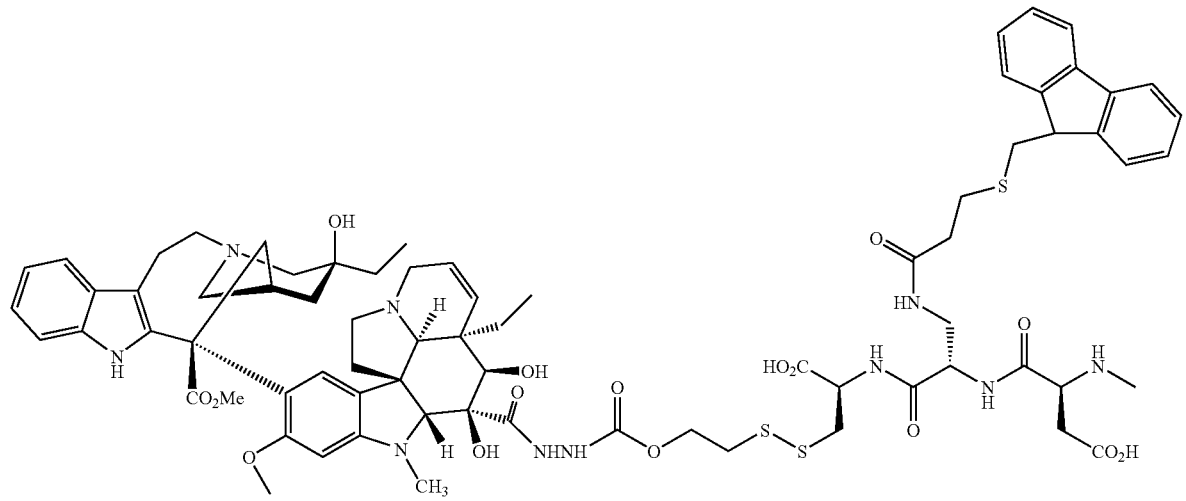

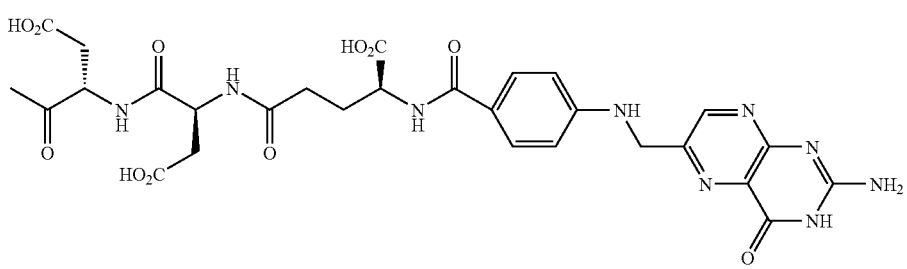

In a polypropylene centrifuge bottle, Example 3 (56 mg) was dissolved in 7.5 mL of water and bubbled with argon for 10 min. In another flask, a 0.1 N NaHCO$_3$ solution was bubbled with argon for 10 min. The pH of the Example 3 solution was adjusted to 6.9 using the 0.1 N NaHCO$_3$ solution. Example 6 (44 mg) in 7.5 mL of tetrahydrofuran (THF) was added slowly to the Example 3 solution. The resulting clear solution was stirred under argon for 15 min to 1 h. Progress of the reaction was monitored by analytical HPLC (10 mM ammonium acetate, pH=7.0 and acetonitrile). THF was evaporated and the aqueous solution was filtered and purified by prep-HPLC. Elution with 1 mM sodium phosphate pH=7.0 and acetonitrile resulted in pure fractions, which were pooled, evaporated at ambient temperature, and the resulting aqueous solution was adjusted to pH 4.0 using 0.1 N HCl. Example 10 was isolated after freeze-drying for 48 h (61 mg, 64%). $^1$H HMR spectrum and LCMS data consistent with the assigned structure.

Example 11

Method A. Example 11 was prepared according to the following process:

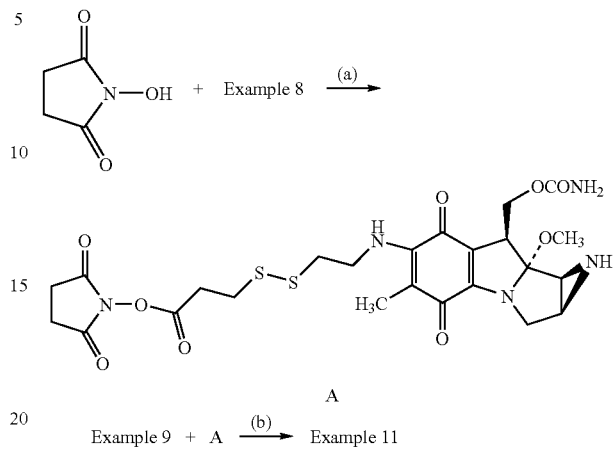

(a) is DCC, DIPEA, THF; and (b) is water/THF at pH 8.5.
Mitomycin C-ethyl disulfide propionic acid (34.4 mg, 0.069

Figure 9:
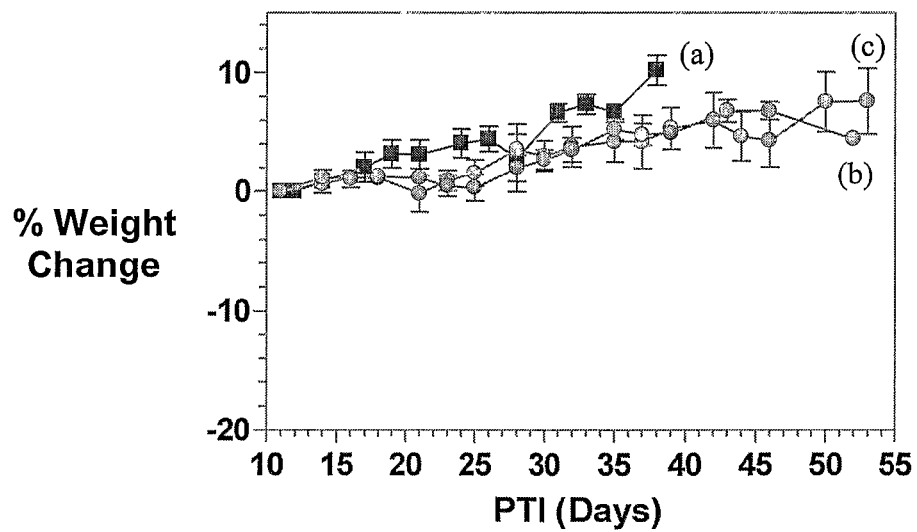
FIG. 9 shows the absence of an effect by Example 11 at 1 μmol/kg TIW for 2 weeks (6 doses) on the weight of nude mice with (b) and without (c) 40 μmol/kg EC20 (rhenium complex) versus untreated controls (a).
Figure 10:
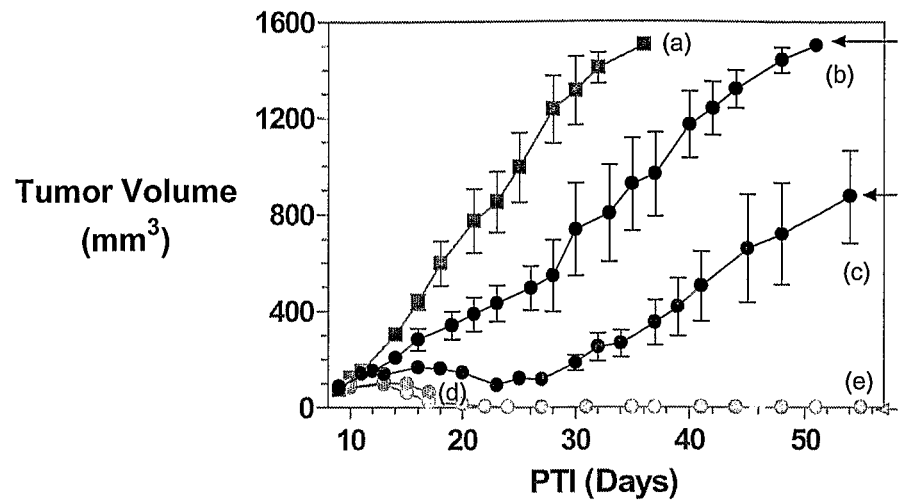
FIG. 10 shows the activity of Example 11 at 2 μmol/kg TIW (e) on folate receptor positive human tumors in nude mice as compared to a mixture of the unconjugated base drugs, mitomycin C and desacetylvinblastine monohydrazine, at 0.5 μmol/kg TIW (b), 1 μmol/kg TIW (c), and 2 μmol/kg TIW (d), and compared to untreated controls (a).

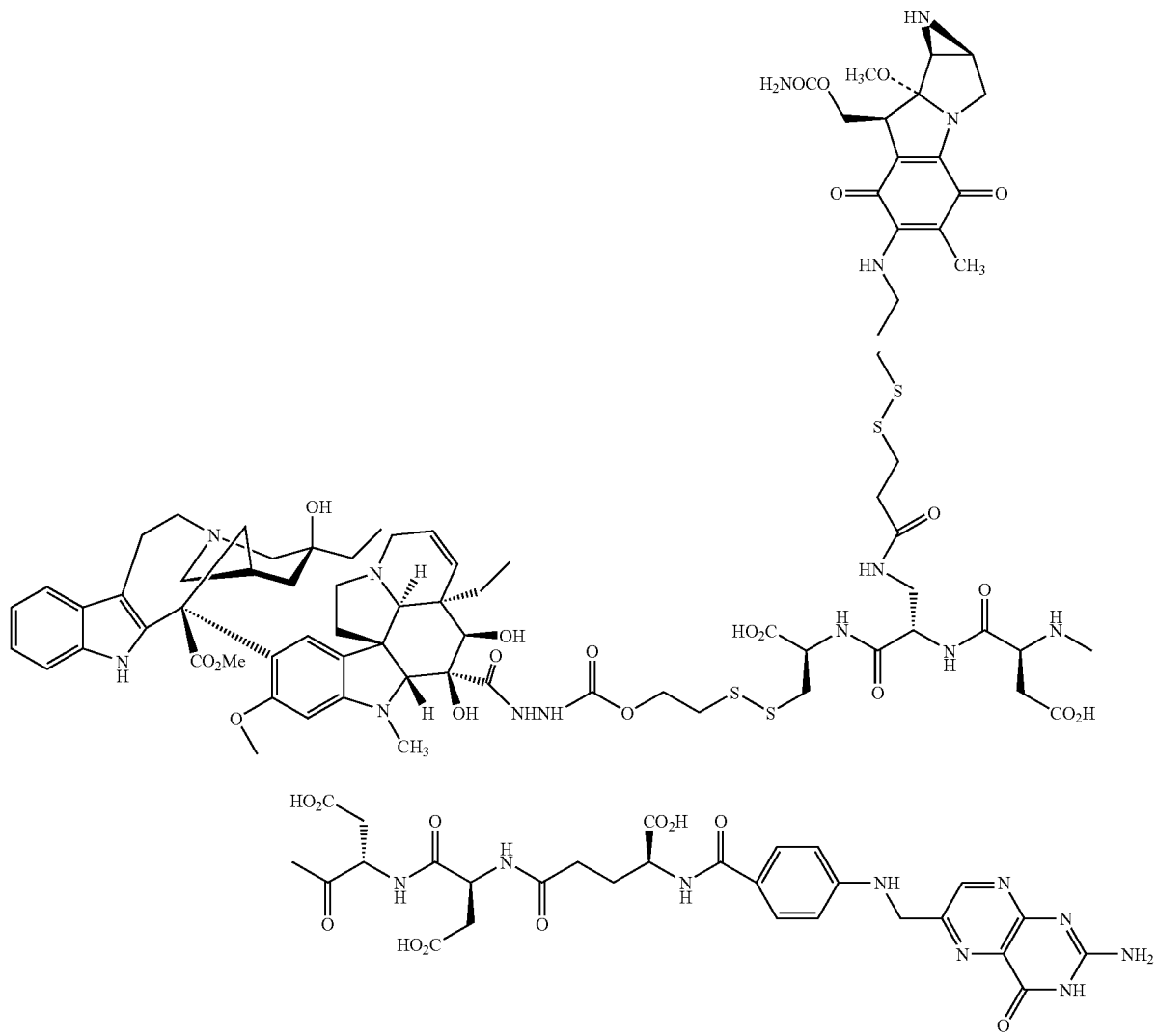

mmol) was dissolved in dry THF (1 mL) under argon. N-hydroxy succinamide (7.9 mg, 0.069 mmol) followed by dicyclohexyl carbodiimide (14.2 mg, 0.069 mmol) was added. Di-isopropylethylamine (0.024 mL, 0.138 mmol) was added and the resulting mixture was stirred for 3 h. In a polypropylene centrifuge bottle, vinblastine folate (Example 9, 26 mg, 0.014 mmol) was dissolved in 3 mL of water. The pH of the solution was slowly adjusted to 8.5 using 0.1 N NaHCO$_3$. The activated mitomycin C derivative prepared as described herein was added to the folate solution as a 3 mL THF solution. The resulting solution was stirred under argon for 15 min to 1 h, where the progress of the reaction was monitored by analytical HPLC (10 mM ammonium acetate and acetonitrile, pH=7.0). The THF was removed under reduced pressure and the aqueous solution was filtered and injected onto a prep-HPLC column (X-terra Column, 19×300 mm). Elution with 1 mM sodium phosphate (pH=7.0) and acetonitrile resulted in pure fractions, which were evaporated and freeze-dried for 48 h to 12 mg (50%, based on recovered starting material). $^1$H NMR and mass spectral data supported that assigned structure as shown in FIGS. 9 and 10 respectively. $C_{103}H_{127}N_{23}O_{32}S_4$; Exact Mass 2325.79; MW 2327.51. HPLC-RT 20.054 min., 99% pure, $^1$H HMR spectrum consistent with the assigned structure, and MS (ES+): 1552.5, 116.0, 1165.3, 1164.3, 1148.4, 744.9, 746.4, 745.6.

Method B.: Anhydrous DMF (4.5 mL) was syringed into a mixture of Example 10 (103 mg, 48.7 μmol) and Example 8 (NO$_2$-PySSCH$_2$CH$_2$-MMC, 33.4 mg, 1.25 eq) at room temperature under argon. To the resulting solution were syringed in DIPEA (84.9 μL, 10 eq) and DBU (72.9 μL, 10 eq) in tandem. The reaction mixture was stirred at room temperature under argon for 20 minutes, then transferred into a stirring diethyl ether (50 mL). The resulting suspension was centrifuged, the precipitate was washed with diethyl ether (15 mL×2), then dissolved in phosphate buffer (9 mL, 1.25 mM, pH 6.8) and was subject to a preparative HPLC (Column: Waters XTerra RP18, 7 μm, 19×300 mm; Mobile phases: A=1.25 mM phosphate buffer, pH 6.8, B=acetonitrile; Method: 10% B to 40% B over 25 min at 25 mL/min). Fractions from 11.72-13.88 minutes were collected and freeze-dried to afford 105.8 mg material, containing 99.2 mg and 6.6 mg phosphate salts.

Figure 2:
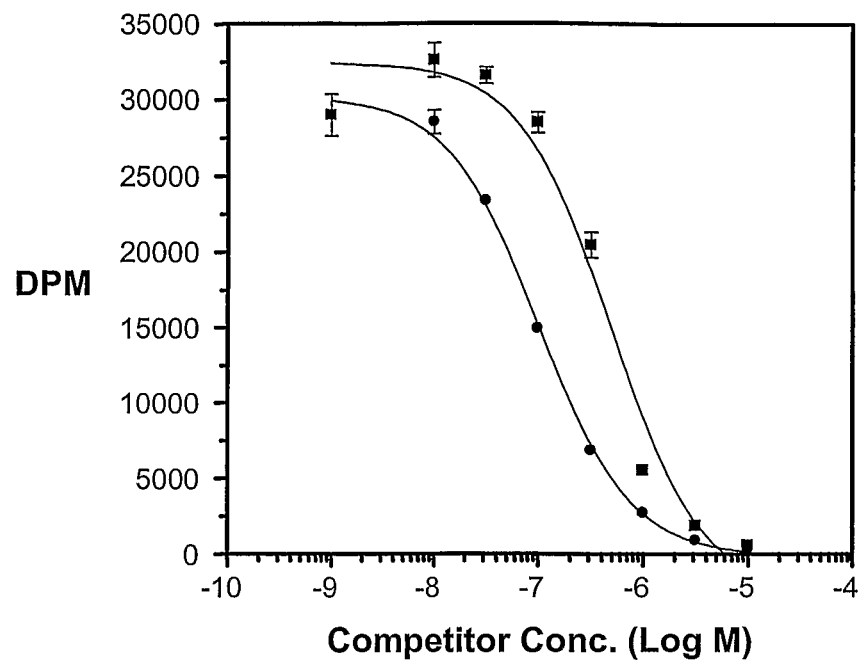
FIG. 2 shows the relative binding affinity of for Example 11 (■, 0.21) versus folic acid (●, 1.0) at folic acid receptors.

Method C. Example 11 was prepared according to the following process in 34% yield:

FIG. 2 shows the relative binding affinity for folic acid (●, 1.0) versus Example 11 (●, 0.21). The data in FIG. 2 shows that the conjugate has high relative binding to the folate receptor. The assay was conducted according to Method Example 4.

Figure 3:
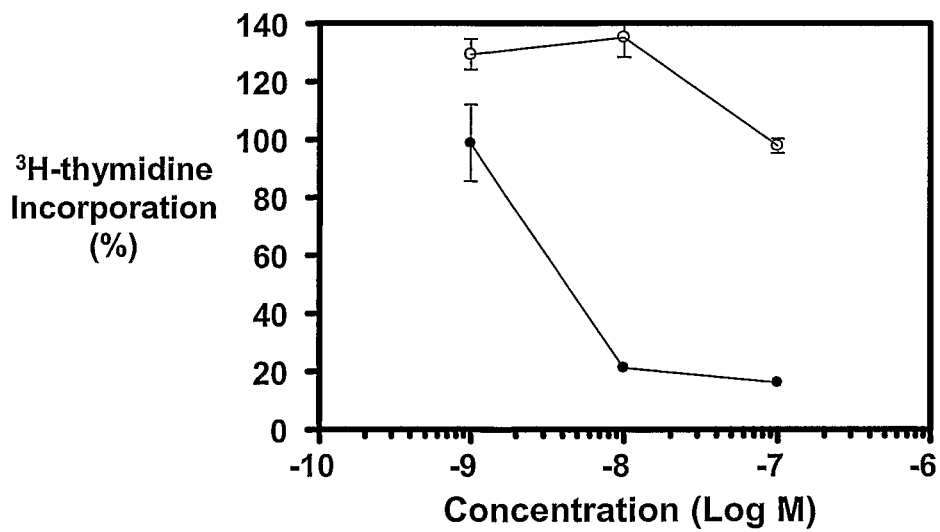
FIG. 3 shows the activity of Example 11 (multi-drug conjugate) on $^3$H-thymidine incorporation with (○) and without (●) excess folic acid; $IC_{50}$ of Example 11=5 nM.

FIGS. 1B and 3 show the effects of Examples 9 (having a single drug) and 11 (having a pair of drugs), respectively, on $^3$H-thymidine incorporation, the IC$_{50}$ of the conjugates of Example 9 (58 nM) and of Example 11 (5 nM). The data in FIGS. 1B and 3 also show that folic acid competes with the conjugates for binding to the folate receptor demonstrating the specificity of binding of the conjugate. The assays were conducted according to Method Example 3. In addition, Example 11 having two drugs showed more than 10-fold more potency at the folate receptor than Example 9 having only a single drug.

Figure 4:
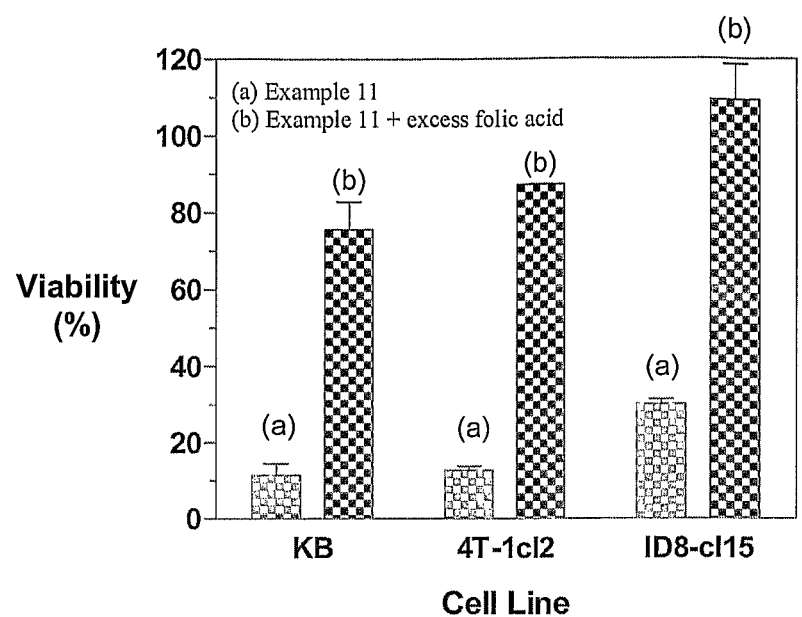
FIG. 4 shows the in vitro cytotoxic activity of Example 11 (a) on three different tumor cell lines (KB, 4T-1c12, and ID8-c115) compared to Example 11+excess folic acid (b).

FIG. 4 shows the in vitro cytotoxic activity of Example 11 (a) on three different tumor cell lines (KB, 4T-1c12, and ID8-c115). In addition, FIG. 4 shows that the cytotoxic activity of Example 11 reduced in the presence of excess folic acid (b), indicating that Example 11 is acting at the folate receptor.

Figure 5A:
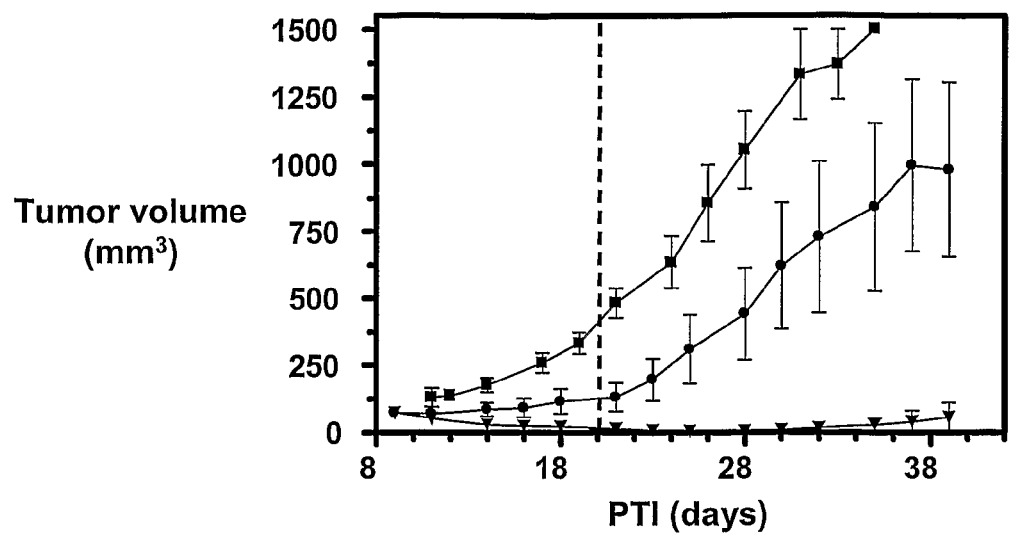
FIG. 5A shows the activity of Example 11 at 1 μmol/kg TIW (6 doses) (●), and 2 μmol/kg TIW (6 doses) (▼) on FR-positive M109 tumors in Balb/c mice versus untreated controls (■).
Figure 5B:
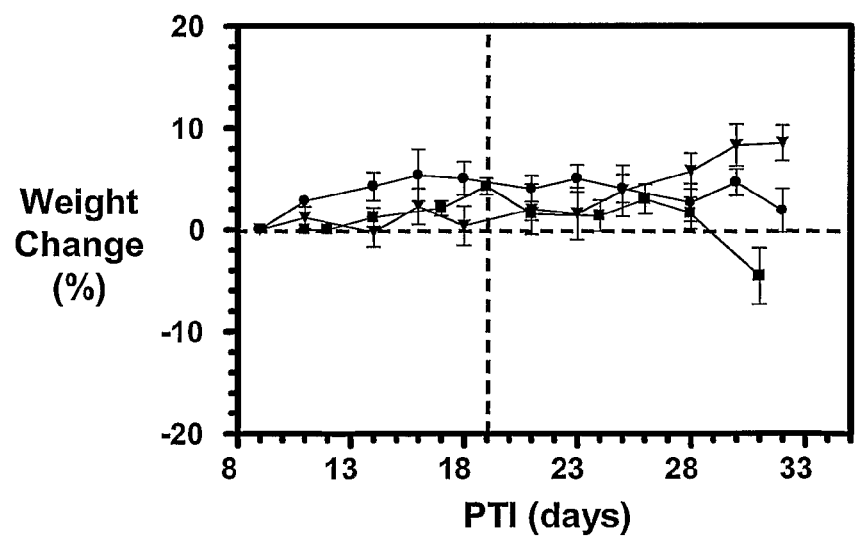
FIG. 5B shows the absence of an effect by Example 11 at 1 μmol/kg TIW (6 doses) (●), and 2 μmol/kg TIW (6 doses) (▼) on the weight of Balb/c mice versus untreated controls (■).

FIGS. 5A and 5B show the activity of Example 11 at two different doses (1 μmol/kg & 2 μmol/kg) against M109 lung cancer tumors in Balb/c mice and on the weight of Balb/c mice (Balb/c mice were used for the M109 tumor volume assay). The assays were performed according to Method Examples 1 and 6, respectively. Example 11 inhibited the growth of solid tumors, but had little effect on the weight of the mice at both doses. In addition, the higher dose (2 μmol/kg) showed strong inhibition of tumor growth, even after the dosing was terminated on day 20. The vertical line corresponds to the last dosing day (Day 20). Five animals were tested, and at the higher dose of 2 μmol/kg, all five animals showed a complete response.

Figure 6:
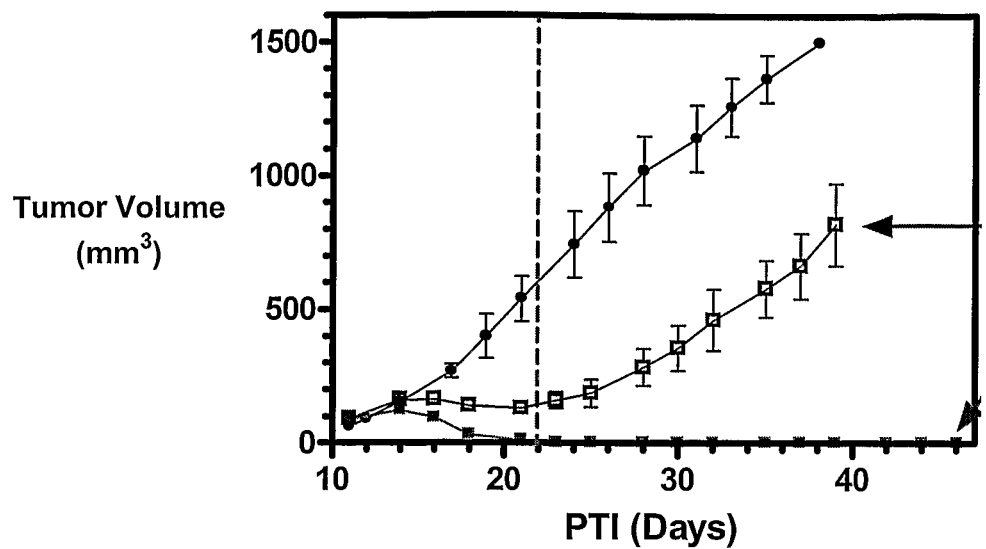
FIG. 6 shows the activity of Example 11 at 1 μmol/kg TIW for 2 weeks (6 doses) on FR-positive KB tumors with (□) and without (■) 40 mmol/kg EC20 (rhenium complex) versus untreated controls (●); Example 11 alone showed 5/5 complete responses; Example 11+EC20 showed 0/5 complete responses.
Figure 7:
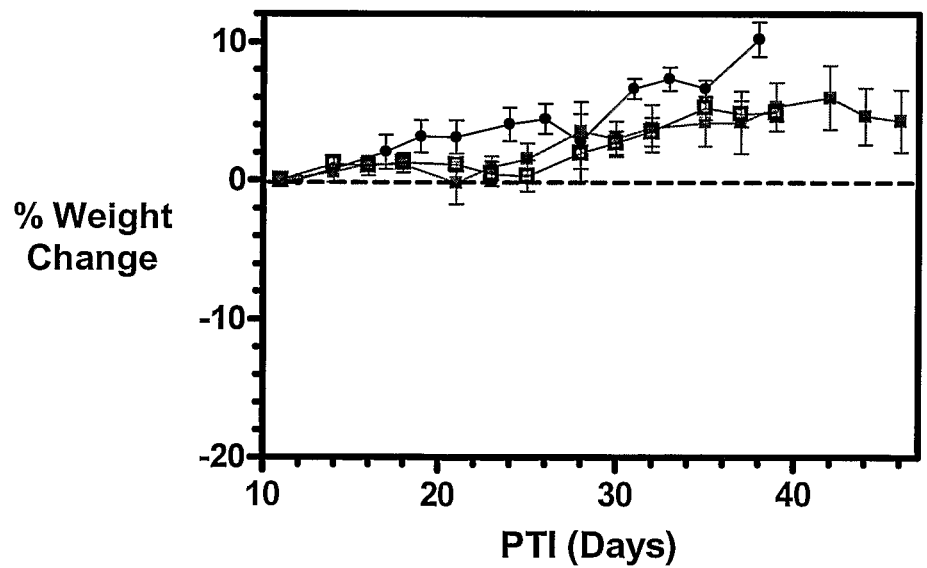
FIG. 7 shows the absence of an effect by Example 11 at 1 μmol/kg TIW for 2 weeks (6 doses) on the weight of nu/nu mice with (□) and without (■) 40 μmol/cg EC20 (rhenium complex) versus untreated controls (●).

FIG. 6 shows the activity of Example 11 at 1 μmol/kg TIW for 2 weeks on FR-positive KB tumors with (b) and without (c) 40 μmol/kg EC20 (rhenium complex), compared to controls (a). The vertical dashed line indicates the last dosing day. The figures show that Example 11 inhibits the growth of solid tumors, and that inhibitory effect is prevented (competed) by

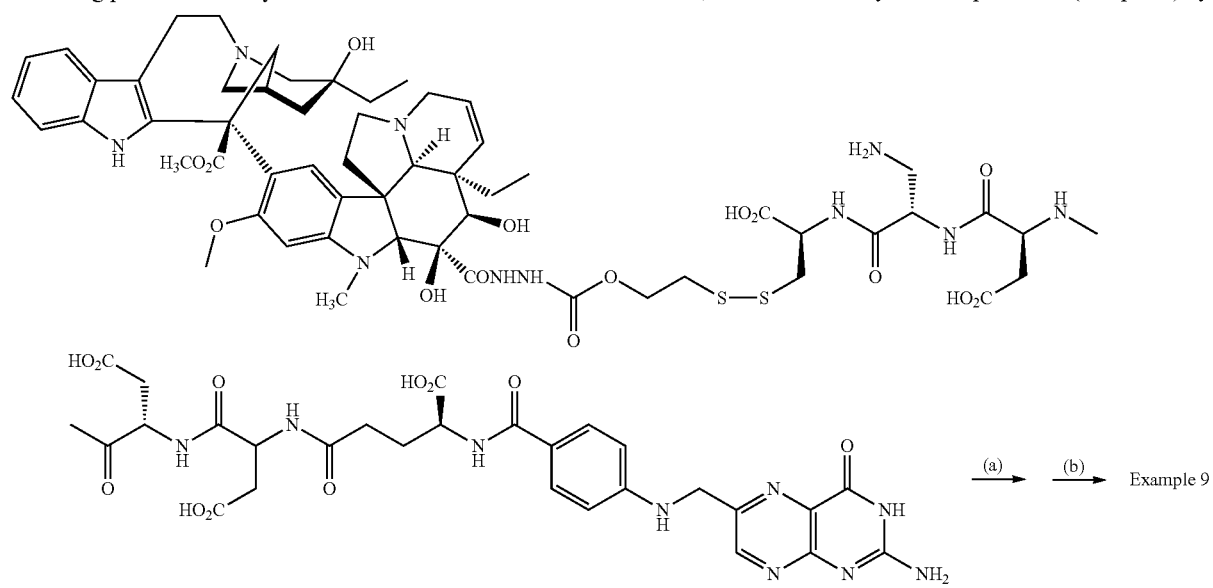

(a) NHS, DCC-Resin, DIPEA, THF; (b) Example 7, DIPEA, DMSO.

the EC20 rhenium complex. In addition, the figures show that treatment with Example 11 did not affect the weight of the test animal significantly from controls. EC20 (rhenium complex) is the compound of the formula

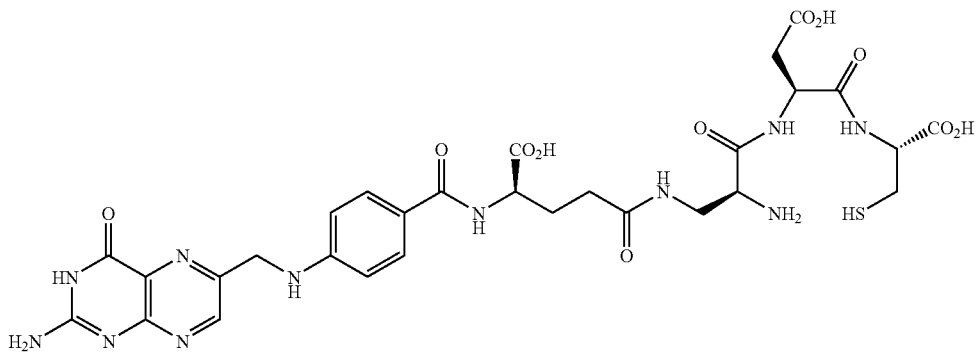 [SMILES: Nc1nc2ncc(CNc3ccc(C(=O)N[C@H](CCC(=O)NC[C@H](N)C(=O)N[C@@H](CC(=O)O)C(=O)N[C@@H](CS)C(=O)O)C(=O)O)cc3)nc2c(=O)[nH]1]

chelated to Rhenium. The preparation of EC20 is described in U.S. patent application publication no. US 2004/0033195 A1, the synthetic procedure description of which is incorporated herein by reference. The assay was performed according the Method Example 2. EC20 acts as a competitor of Example 11 at folate receptors, and the results show the specificity of the effects of Example 11.

Figure 8:
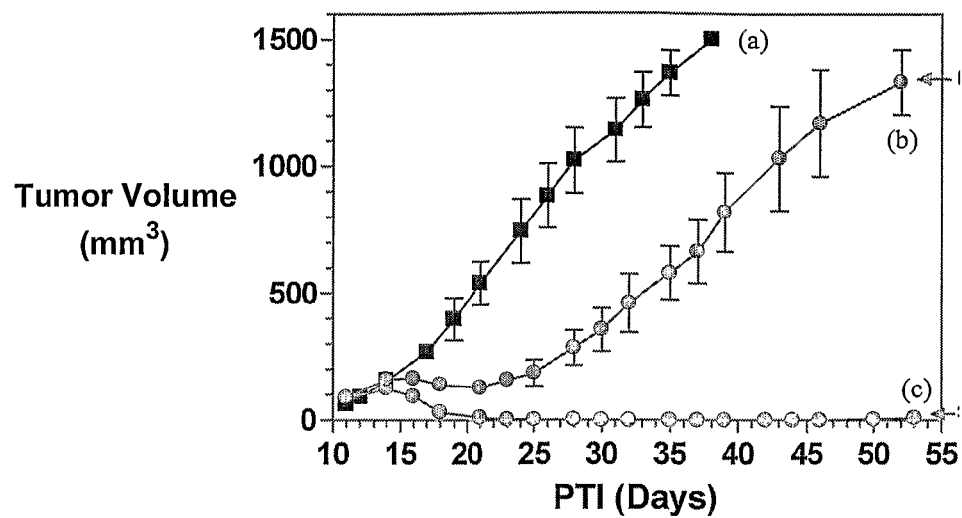
FIG. 8 shows the activity of Example 11 at 1 μmol/kg TIW for 2 weeks (6 doses) on s.c. human xenograft KB tumors implanted in nude mice with (b) and without (c) 40 μmol/kg EC20 (rhenium complex) versus untreated controls (a); Example 11 alone showed 5/5 complete responses; Example 11+EC20 showed 0/5 complete responses.

FIG. 8 shows the activity of Example 11 at 1 μmol/kg TIW on folate receptor positive s.c. implanted human xenograft KB tumors with (b) and without (c) added 40 μmol/kg EC20 (rhenium complex) in nude mice. The data in FIG. 8 show that Example 11 inhibits the growth of solid tumors, and that the inhibitory effect is prevented (competed against) by the EC20 rhenium complex, (b) versus (c). In addition, the data in FIG. 8 show that treatment with Example 11 did not significantly affect the weight of the tested nude mice animal model compared to controls (a).

FIG. 10 shows the activity of Example 11 at 2 μmol/kg TIW (e) on folate receptor positive human tumors in nude mice compared to a mixture of the unconjugated base drugs, mitomycin C and desacetylvinblastine monohydrazide, at 0.5 μmol/kg TIW (b), 1 μmol/kg TIW (c), and 2 μmol/kg TIW (d), compared to untreated controls (a). The data in FIG. 10 show that Example 11 inhibits the growth of solid tumors and gives a complete response in five out of five test animals. In contrast, treatment with the mixture of base drugs at 0.5 μmol/kg TIW (b), or at 1 μmol/kg TIW (c) did not show a complete response in any of the five test animals. The high dose of the mixture of base drugs at 2 μmol/kg TIW (d) was discontinued before day 20 due to observed toxicity, as shown in FIG. 11 showing the effect of the base drugs and Example 11 on test animal weight.

Figure 11:
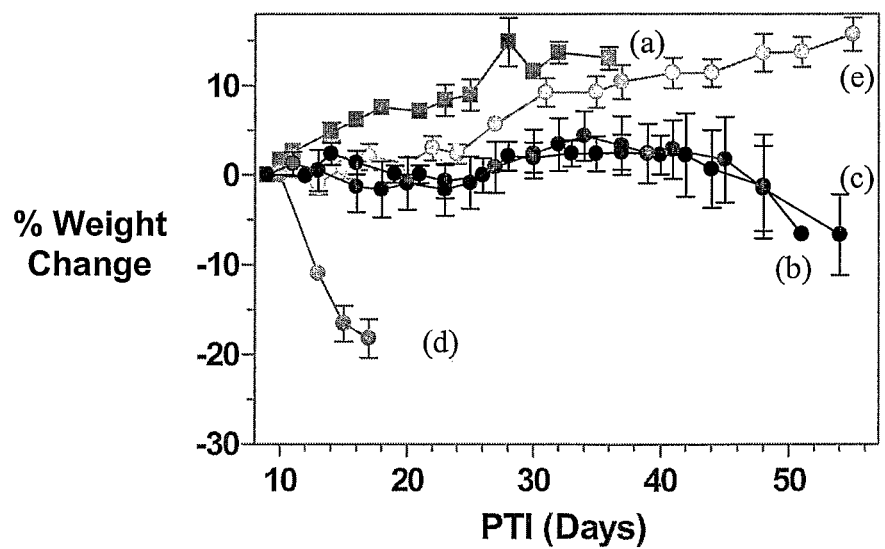
FIG. 11 shows the absence of an effect by Example 11 at 2 μmol/kg TIW for 2 weeks (e) on the weight of nude mice compared to controls (a). Weight loss occurred at the all three doses of the mixture of the unconjugated base drugs, mitomycin C and desacetylvinblastine monohydrazide (0.5 μmol/kg TIW (b), 1 μmol/kg TIW (c), 2 μmol/kg TIW (d)). The high dose (d) was discontinued prior to day 20.

FIG. 11 shows that Example 11 (e) did not significantly affect the weight of the test animals during treatment from controls (a). In contrast to Example 11, the data in FIG. 11 show that prolonged treatment with the lower doses of the mixture of the unconjugated base drugs, mitomycin C and desacetylvinblastine monohydrazide, at (0.5 μmol/kg TIW (b) and 1 μmol/kg TIW (c)) caused weight loss in test animals that was significant compared to controls (a). In addition, the high dose (2 μmol/kg TIW (d)) of the mixture of the unconjugated base drugs caused the greatest weight loss, leading to the termination of that test.

Figure 12:
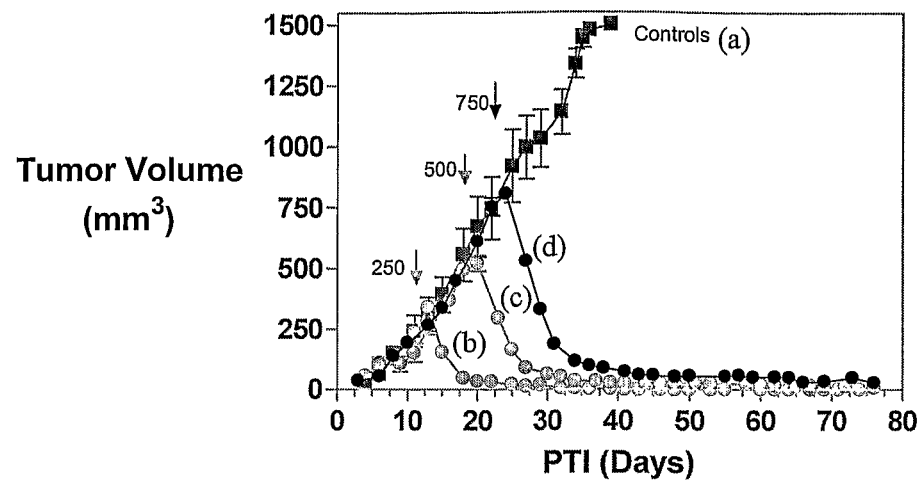
FIG. 12 shows the activity of Example 11 on three sizes of large KB tumors, 250 mm$^3$ (b), 500 mm$^3$ (c), and 750 mm$^3$ (d) in nu/nu mice at 2 μmol/kg TIW for 2 weeks compared to controls (a).

The compounds described herein may be useful in treating large or established tumors. Illustratively, Example 11 is effective on large tumors. FIG. 12 shows the activity of Example 11 at 2 μmol/kg TIW, 2 weeks on large (250 mm$^3$, 500 mm$^3$, and 750 mm$^3$) s.c. KB tumors. Treatment with Example 11 was initiated when the tumors reached one of the three target volumes, as indicated by the vertical arrows corresponding to the tumor volume. The data in FIG. 12 show that Example 11 inhibits the growth of large tumors and gives a complete response in test animals.

Figure 13:
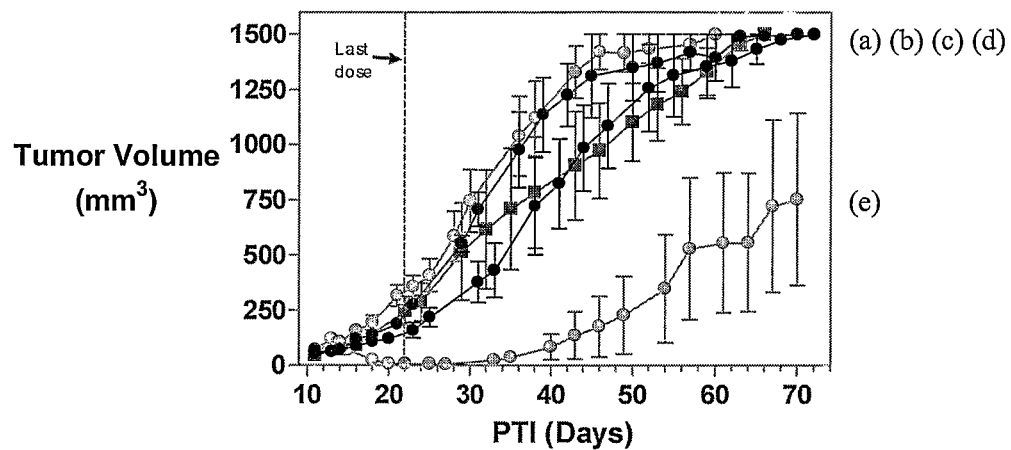
FIG. 13 shows the activity of Example 11 (e) compared to conjugates of only the single drug mitomycin C (b), desacetylvinblastine monohydrazide (c), or a mixture of those two single drug conjugates (d), compared to controls (a).
Figure 14:
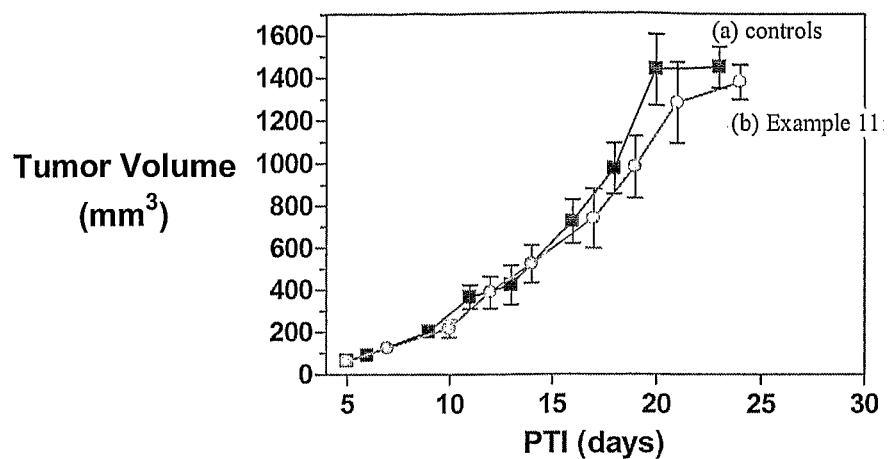
FIG. 14 shows the absence of activity of Example 11 (b) at 2 μmol/kg TIW for two weeks of treatment on folate receptor negative 4T1 tumors in Bablb/c mice, compared to controls (a). The data in FIG. 14 show that Example 11 (b) does not have any effect on the tumors compared to controls (a) due to the absence of folate receptors on those tumors.

FIG. 13 shows the activity of Example 11 (e) at 1 μmol/kg TIW for two weeks of treatment on established s.c. KB tumors, compared to controls (a); the conjugates of each single drug alone, mitomycin C conjugate (b) and desacetylvinblastine monohydrazide conjugate (c), or a mixture of those single drug conjugates (d). Each drug conjugate was dosed at the same level of 1 μmol/kg TIW for two weeks of treatment. The figure shows that Example 11 performs better than either single drug conjugate or a mixture of both single drug conjugates. Surprisingly, the mixture of single drug conjugates did not perform significantly better than the single drug conjugates dosed individually, and none of the single drug conjugate dosing regimens was statistically significant from the controls. Only the compound of Example 11 was superior to controls. In addition, these data suggest a synergistic effect of having both a vinca drug and a mitomycin drug on the single conjugate.

Examples 12 to 14

Prepared according to the processes and conditions described herein, including the processes described hereinabove for Example 11. Additional details for the preparation of the required thiosulfonate or pyridyldithio-activated vinblastine, and maleimide-activated vinblastine derivatives are described in U.S. patent application publication no. US 2005/0002942 A1. Additional details for the preparation of the required mitomycin derivatives are described in U.S. patent application publication no. US 2005/0165227 A1, the disclosure of which is incorporated herein by reference.

Figure 15:
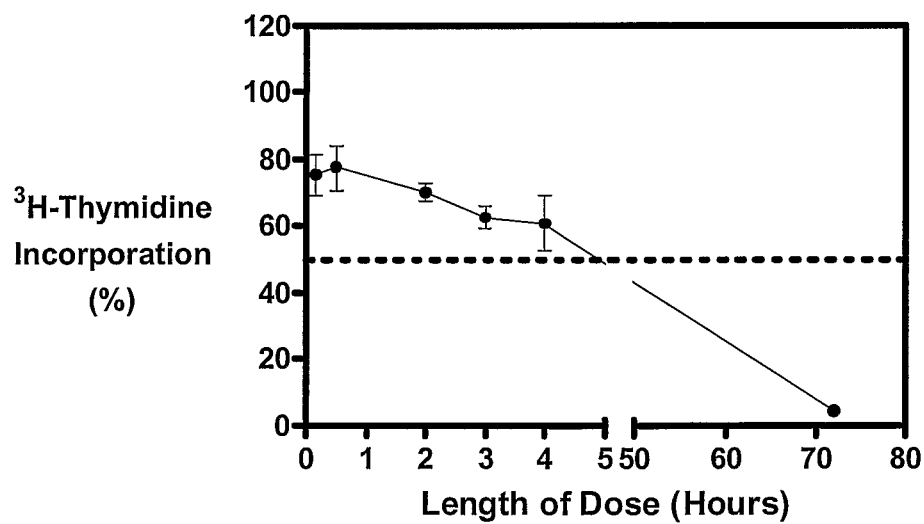
FIG. 15 shows the activity of Example 12 on $^3$H-thymidine incorporation into FR-positive KB cells

Example 12
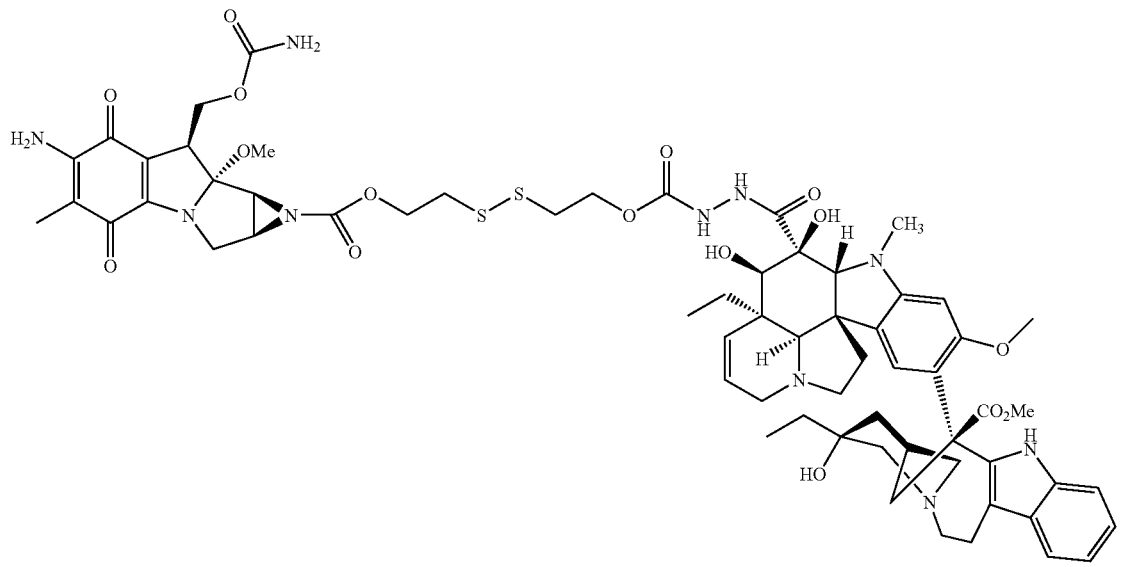
FIG. 15 shows the activity of Example 12 at 100 nM on ³H-thymidine incorporation into FR-positive KB cells versus the pulse time. The assay was performed according to Method Example 3.
Example 13
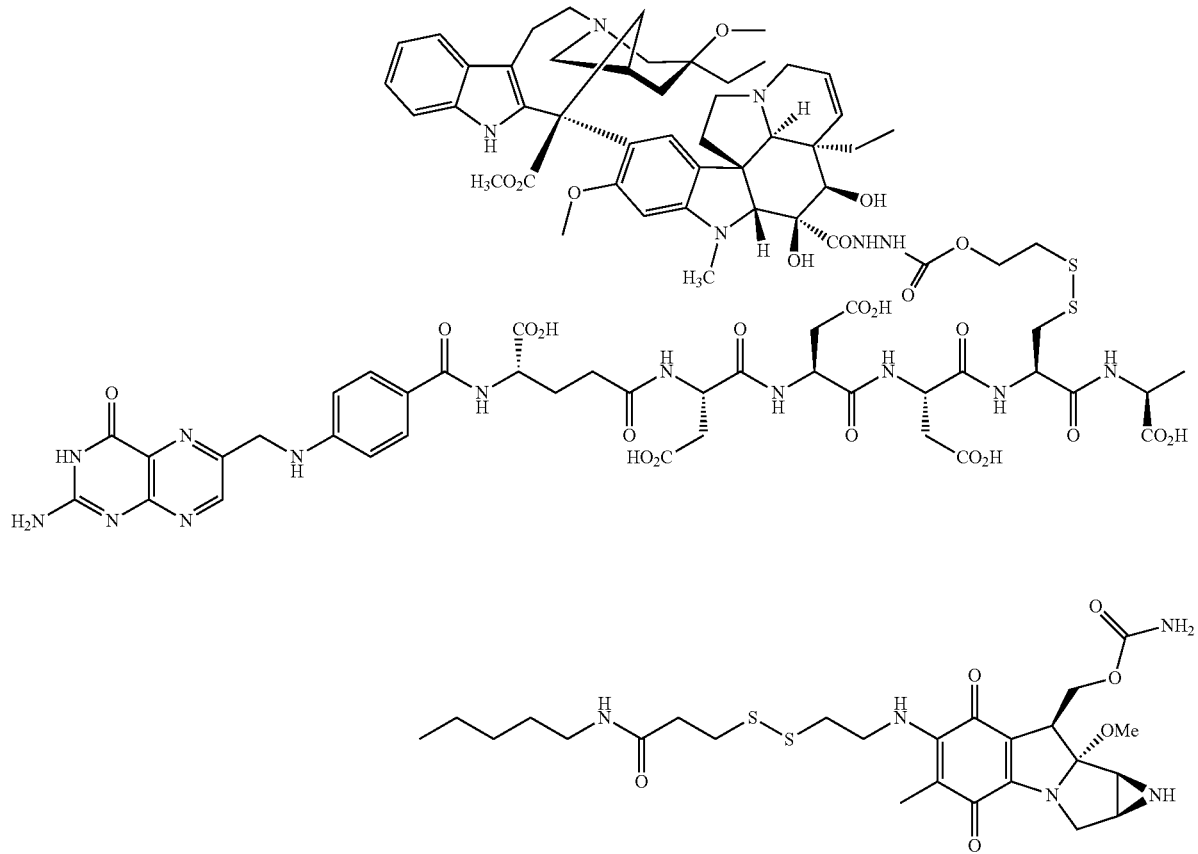

Example 14
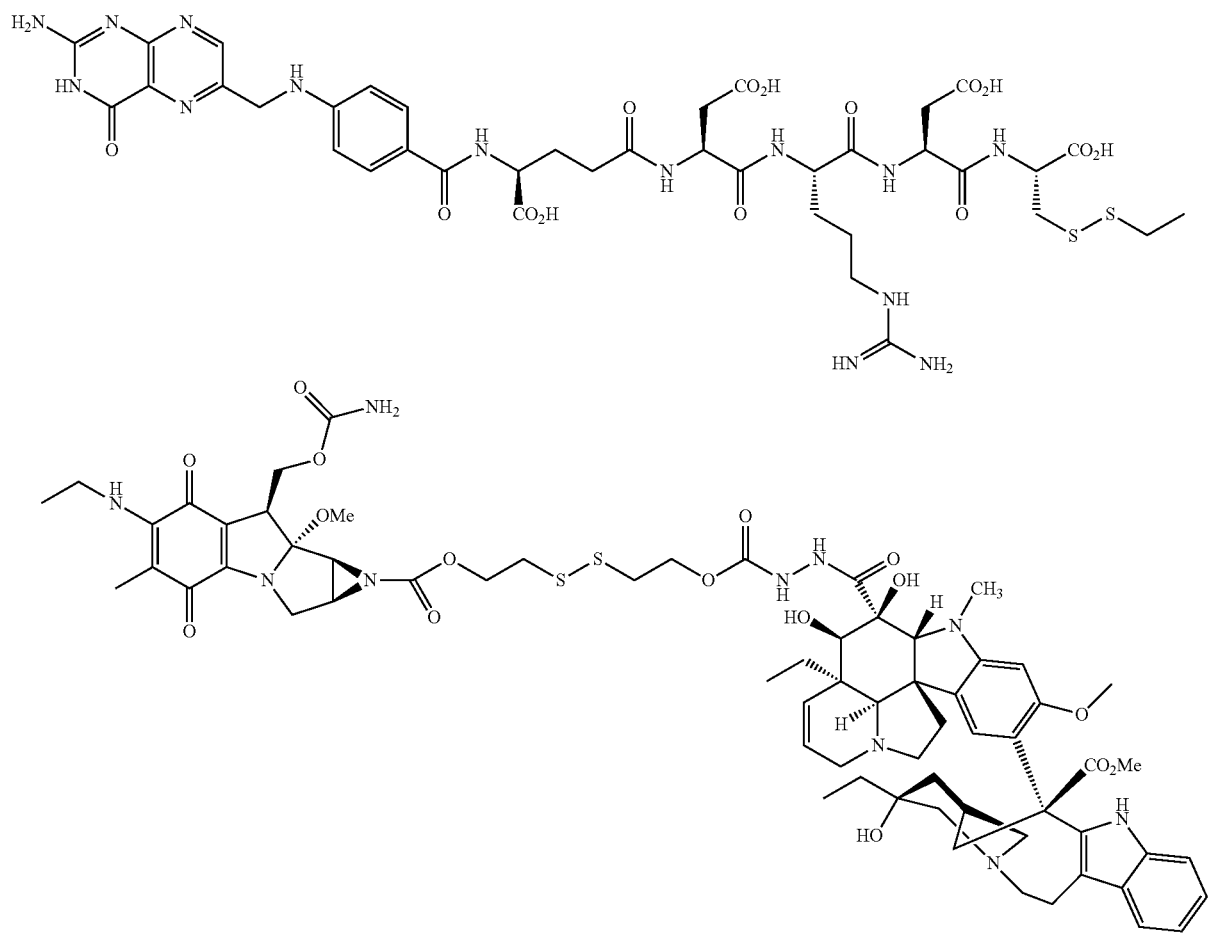
What is claimed is:
1. A compound of the formula

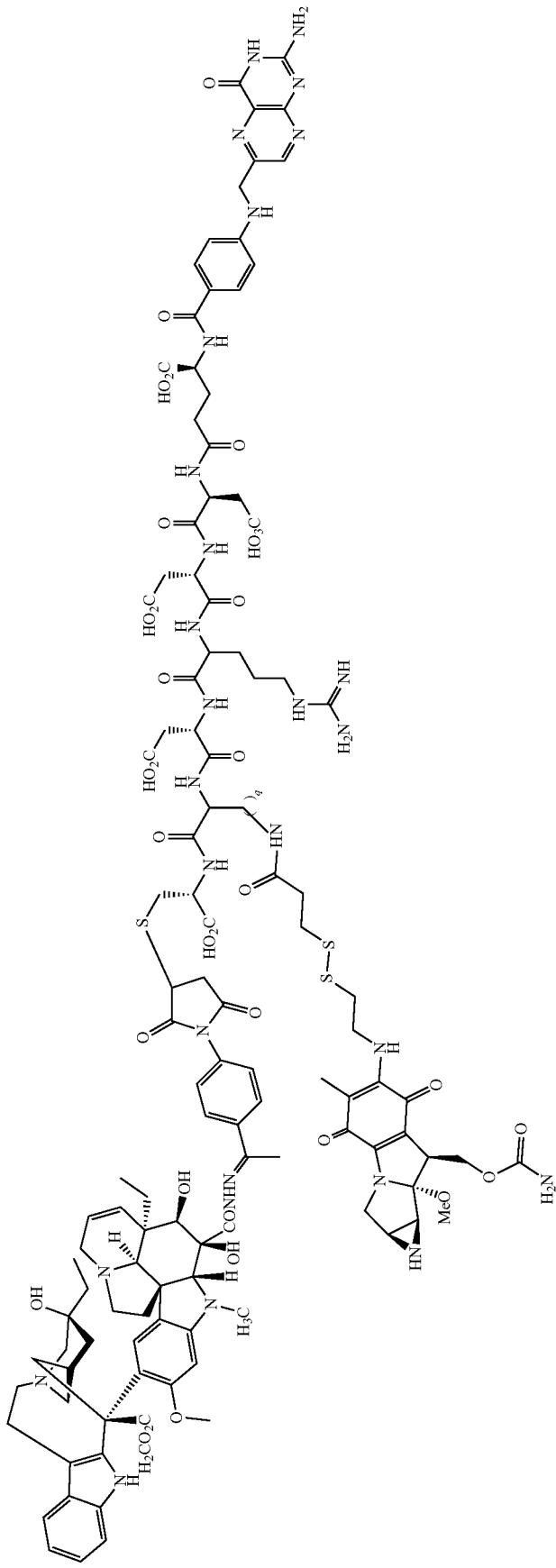

or a pharmaceutically acceptable salt thereof, wherein q is an integer from 0 to 8; or

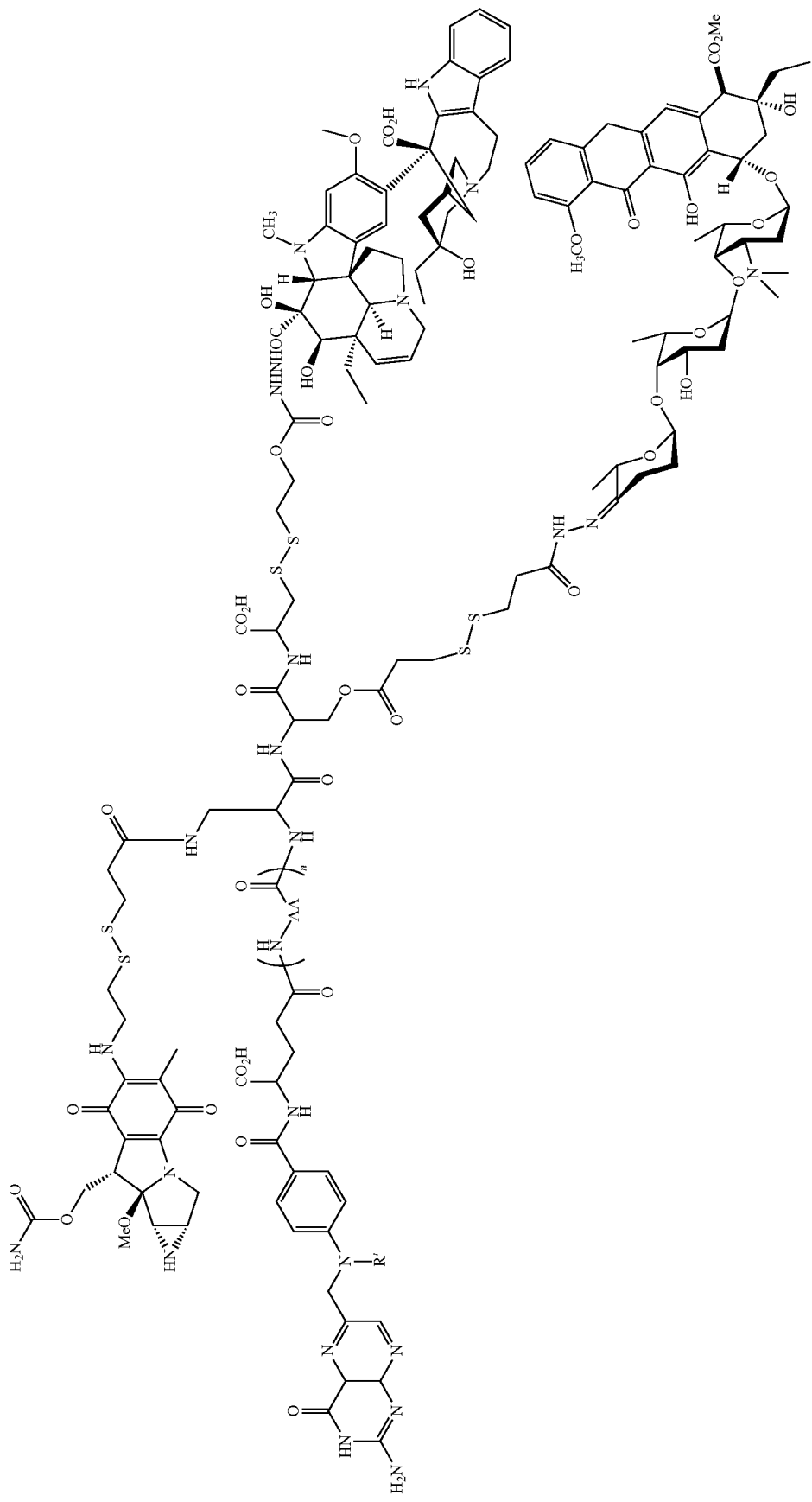

or a pharmaceutically acceptable salt thereof, wherein AA forms an amino acid; and n is an integer from 0 to 8.
2. The compound of claim 1 wherein q is 1 to 8.
3. The compound of claim 1 wherein n is 1 to 8.
4. A compound of the formula
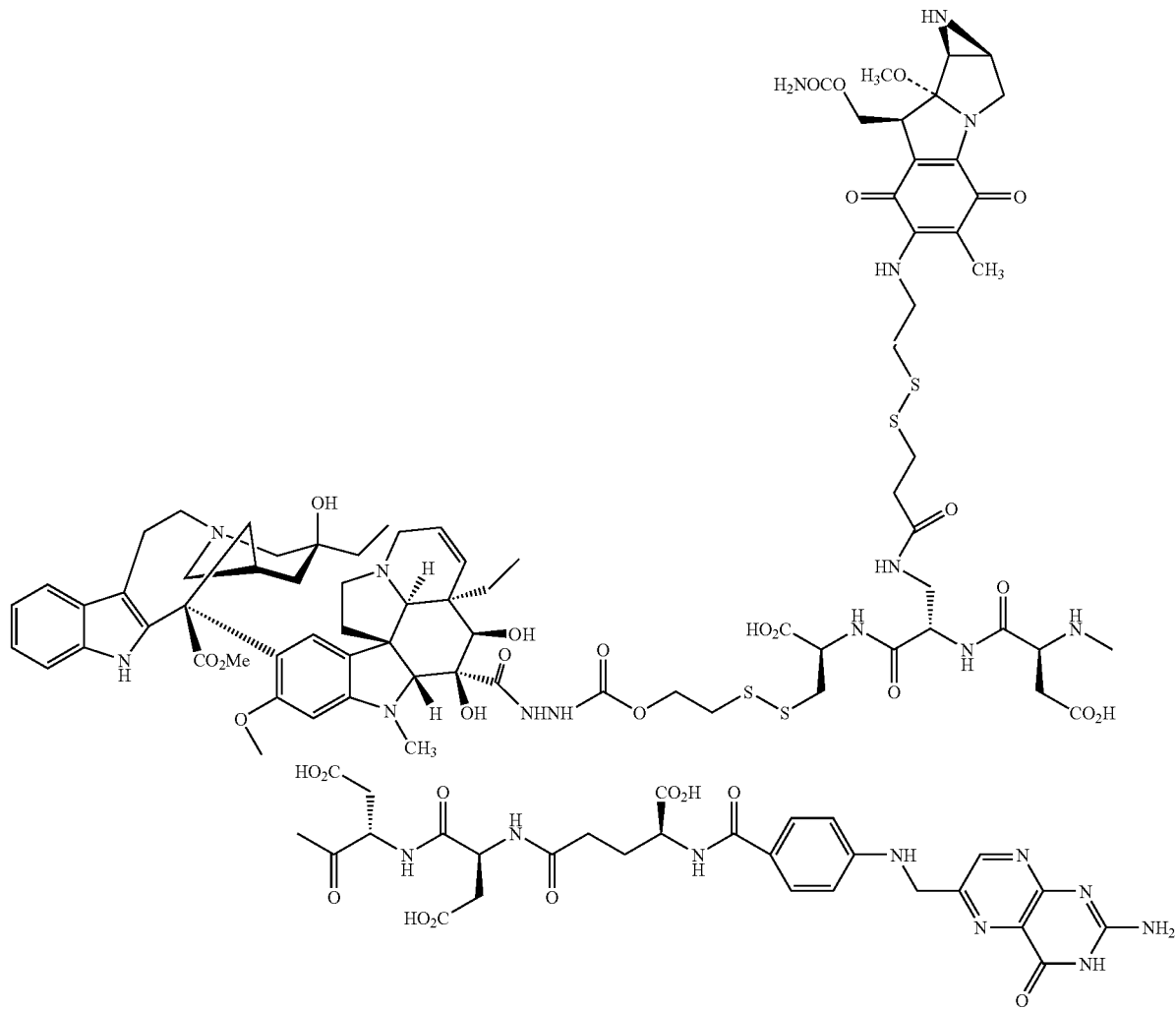
or
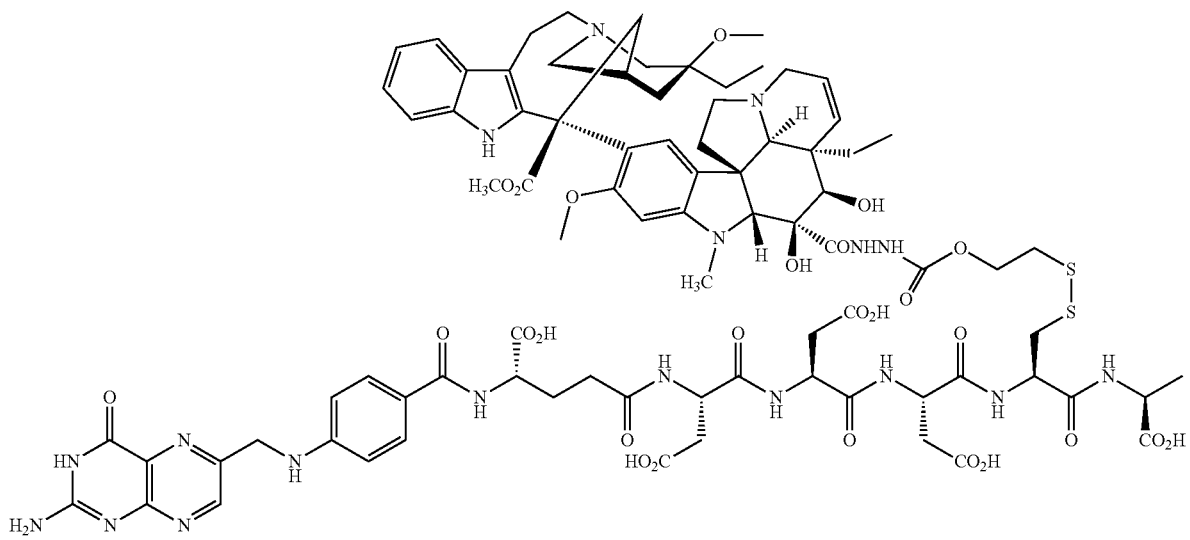

-continued
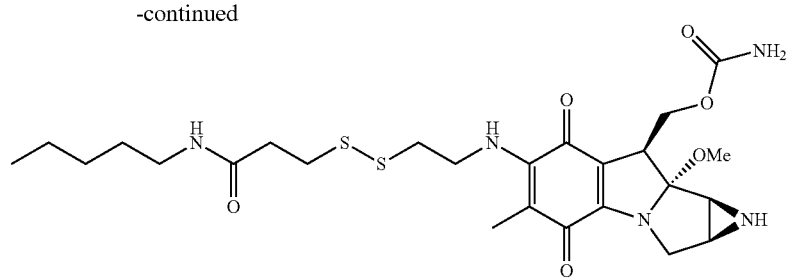
or
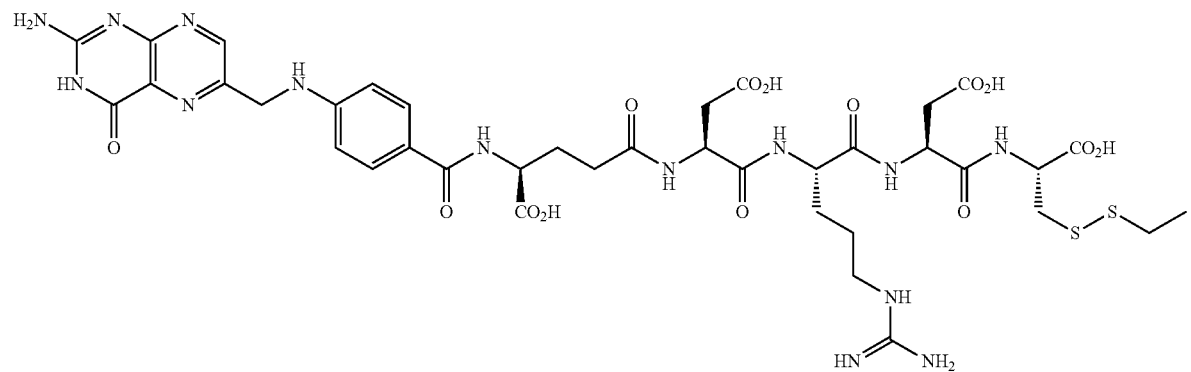
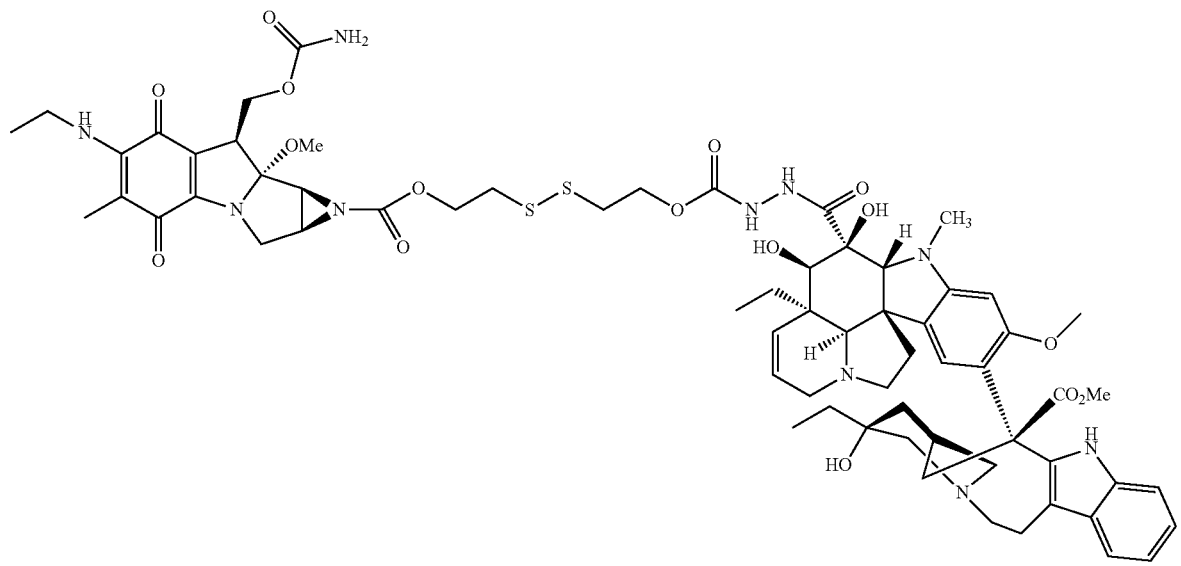
or a pharmaceutically acceptable salt thereof.

5. The compound of claim 4 the formula
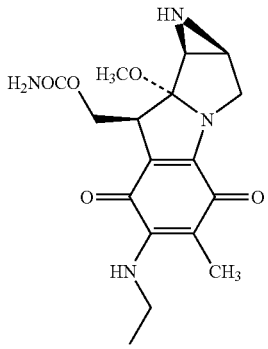
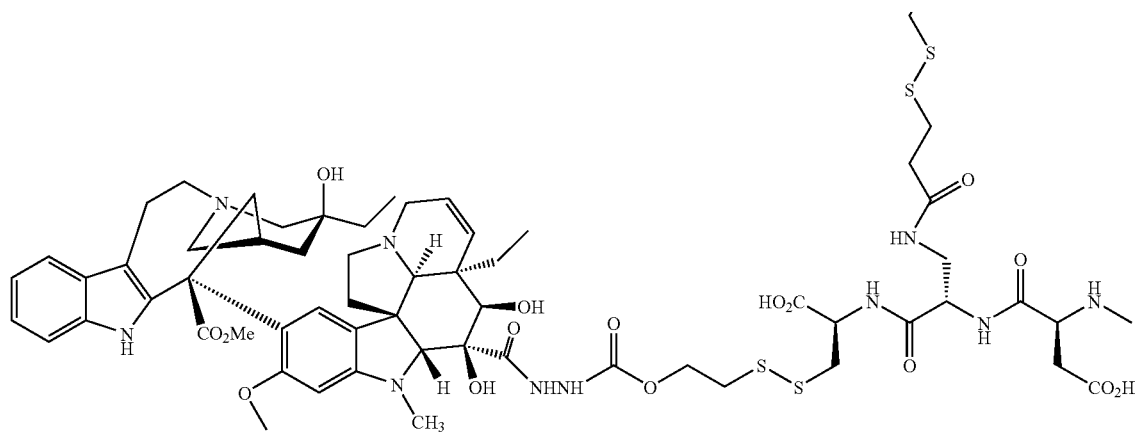
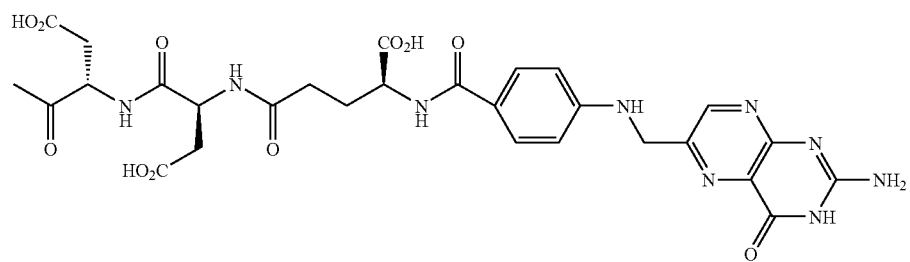
or a pharmaceutically acceptable salt thereof.

6. The compound of claim 4 the formula
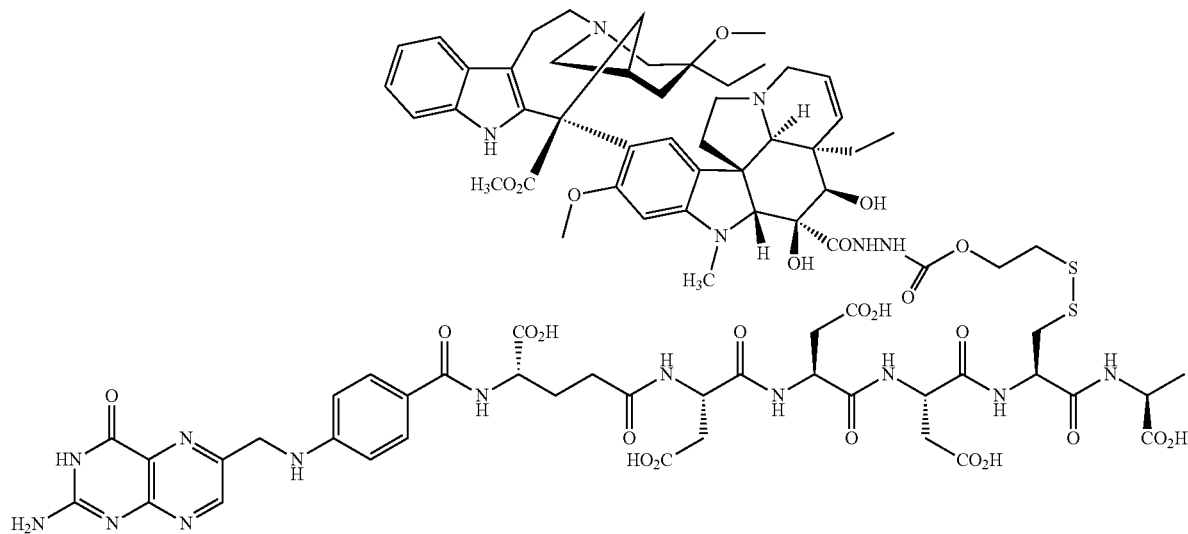
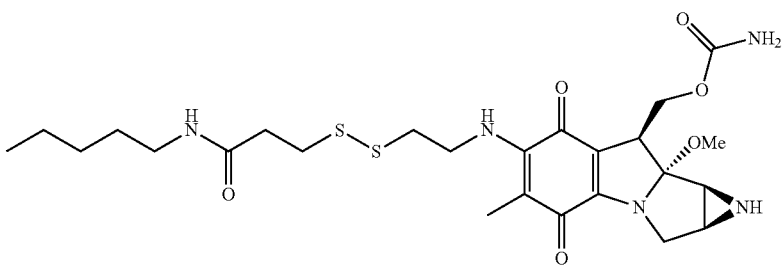
45
or a pharmaceutically acceptable salt thereof.
7. The compound of claim 4 the formula
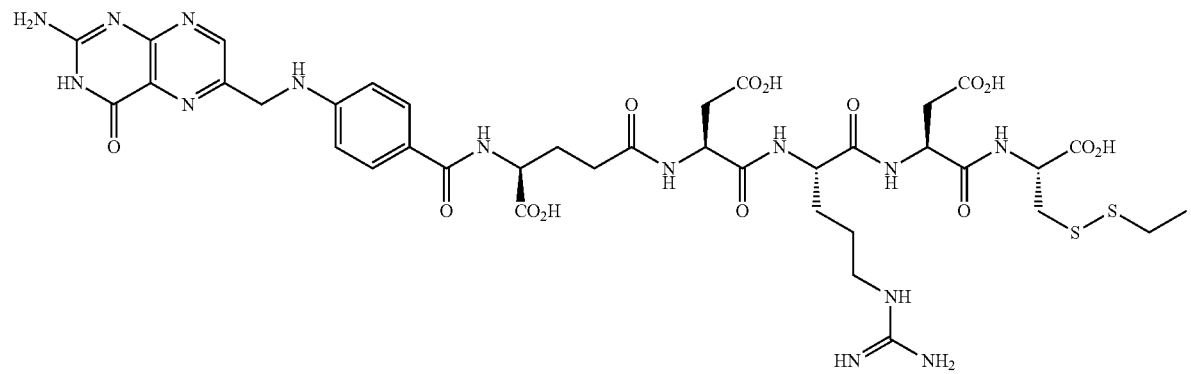

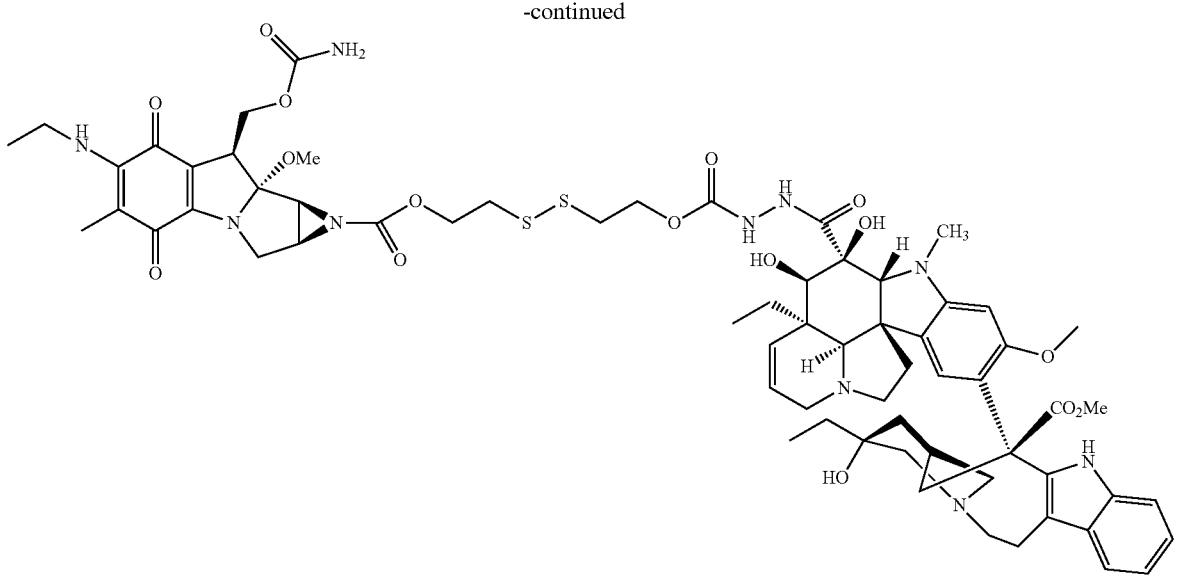
or a pharmaceutically acceptable salt thereof.
8. A pharmaceutical composition comprising a drug delivery conjugate of claim 4, and a pharmaceutically acceptable carrier, diluent, or excipient therefor.
9. A pharmaceutical composition comprising the compound of claim 1, and a pharmaceutically acceptable carrier, diluent, or excipient therefor.
\* \* \* \* \*